United States Patent
Yeshwantpur et al.

(10) Patent No.: US 7,899,650 B2
(45) Date of Patent: Mar. 1, 2011

(54) APPARATUS AND METHOD FOR DETECTING AND IDENTIFYING RAMAN SIGNATURES

(75) Inventors: Abhijit Yeshwantpur, Baltimore, MD (US); Joel M. Morris, Columbia, MD (US)

(73) Assignee: University Of Maryland, Baltimore County, Baltimore, MD (US)

( * ) Notice: Subject to any disclaimer, the term of this patent is extended or adjusted under 35 U.S.C. 154(b) by 278 days.

(21) Appl. No.: 12/133,258

(22) Filed: Jun. 4, 2008

(65) Prior Publication Data

US 2009/0063101 A1 Mar. 5, 2009

Related U.S. Application Data

(60) Provisional application No. 60/933,043, filed on Jun. 4, 2007.

(51) Int. Cl.
*H04B 15/00* (2006.01)
(52) U.S. Cl. .......................... 702/189; 702/57; 702/179; 398/79; 372/3; 359/334; 359/349; 356/301; 356/302; 356/306; 356/307; 356/326
(58) Field of Classification Search .................. 702/57, 702/179, 189; 398/79; 372/3; 359/334, 359/349; 356/301, 302, 306, 307, 326
See application file for complete search history.

(56) References Cited

U.S. PATENT DOCUMENTS

| | | |
|---|---|---|
| 5,498,875 A | 3/1996 | Obremski et al. |
| 5,610,836 A | 3/1997 | Alsmeyer et al. |
| 5,926,773 A | 7/1999 | Wagner |
| 6,584,413 B1 | 6/2003 | Keenan et al. |
| 6,675,106 B1 | 1/2004 | Keenan et al. |
| 6,842,702 B2 | 1/2005 | Haaland et al. |
| 6,900,890 B1 | 5/2005 | Rice |
| 6,947,848 B2 | 9/2005 | Bove et al. |
| 7,023,545 B2 | 4/2006 | Slater |
| 7,145,651 B2 | 12/2006 | Li et al. |
| 7,219,038 B2 * | 5/2007 | Tracy et al. .................. 702/189 |
| 7,254,501 B1 | 8/2007 | Brown et al. |
| 7,337,066 B2 | 2/2008 | Neiss |
| 7,656,523 B2 * | 2/2010 | Sun et al. ..................... 356/301 |

\* cited by examiner

*Primary Examiner*—Eliseo Ramos Feliciano
*Assistant Examiner*—Elias Desta
(74) *Attorney, Agent, or Firm*—Nixon Peabody LLP

(57) ABSTRACT

In one aspect, a signal processing system includes a processor, an I/O device operatively associated with the processor, and a memory device bearing instructions configured to cause the processor to obtain a representation of signal data over a data domain and position a sliding-window over a portion of the signal data, such portion corresponding to a sliding-window domain, to analyze the signal data within the sliding-window domain to detect the presence of a signature multiplet and, based on the analysis of the data, to estimate the pedestal of the signal data within the sliding-window domain. The instructions also cause the processor to iteratively shift the sliding-window over at least a portion of the data domain to correspondingly shift the sliding-window domain, estimate the pedestal of the signal data within each sliding-window domain to determine an estimated pedestal over the portion of the data domain, to subtract the estimated pedestal from the signal data to yield a pedestal-free representation of the signal data for the portion of the data domain, and to output the pedestal-free representation of the signal data for the portion of the data domain to a communication device, display, printing device, or data storage device.

20 Claims, 66 Drawing Sheets

APPARATUS AND METHOD FOR DETECTING AND IDENTIFYING RAMAN SIGNATURES

CROSS-REFERENCE TO APPLICATIONS

This application claims the benefit of U.S. Provisional Application Ser. No. 60/933,043, filed on Jun. 4, 2007, which is hereby incorporated by reference in its entirety.

STATEMENT AS TO RIGHTS TO INVENTIONS MADE UNDER FEDERALLY SPONSORED RESEARCH AND DEVELOPMENT

The U.S. Government may have certain rights in these inventions pursuant to contract number W91ZLK-05-P-1210 awarded by the U.S. Army/ECBC.

FIELD OF THE INVENTION

The present invention relates generally to signal processing techniques used to isolate and enhance signals within data, and more particularly to signal processing techniques used to isolate and enhance signals within Raman spectroscopy data and, still more particularly, to signal processing techniques for detecting and identifying chemical Raman signatures in Raman shift data.

BACKGROUND

Raman spectroscopy has found applications in a wide variety of areas that involve identifying and characterizing chemicals. For example, Raman spectroscopy has been used in microelectronics fabrication, criminal investigations, biochemistry, archaeology, biomedical areas, military applications, and homeland security.

Infrared (IR) spectroscopy is another technique for characterizing chemicals and chemical processes; however, Raman spectroscopy has several advantages over IR spectroscopy. Firstly, not all chemicals are IR active. Due to the complementary nature of these two methods, such IR-inactive chemicals become visible to Raman spectrometers. Secondly, aqueous solutions render IR spectrometers ineffective, whereas they are inconsequential to Raman spectrometers. Other issues such as, for example, sampling or interference from glass backgrounds plague IR spectroscopy. Raman spectroscopy, therefore, is attractive for such IR-unfriendly scenarios.

The advantages of Raman spectroscopy over IR spectroscopy come at a cost of a low signal-to-interference-and-noise ratio (SINR). Signal degradation sources assume greater importance leading to formidable signal processing challenges for achieving adequate interference and noise reduction, and signal detection and discrimination performance. Two major sources contributing to "background" interferences are fluorescence of the environment and/or the target chemical itself, and the light collecting instrument's transfer function (IRC). The effect of these two sources of background are collectively termed the "pedestal," as they non-uniformly raise and reshape the spectral plot of a given ideal background-free chemical spectrum. There is a need for an algorithm that is capable of detecting and identifying chemical Raman signatures in Raman shift data while accounting for the pedestal interferences.

SUMMARY

In at least one aspect of the present concepts, a signal processing system is provided and comprises a processor, at least one I/O device operatively associated with the processor, and a memory device. The memory device bears instructions that are configured for execution by a processor to cause the processor to obtain a representation of signal data over a data domain. The instructions are further configured to cause the processor to position a sliding-window over a portion of the signal data. The portion of the data domain within the sliding-window corresponds to a sliding-window domain. The instructions are still further configured to cause the processor to analyze the signal data within the sliding-window domain to detect the presence of a signature multiplet and, based on the analysis of the data, estimate the pedestal of the signal data within the sliding-window domain. The instructions are additionally configured to cause the processor to iteratively shift the sliding-window over at least a portion of the data domain to correspondingly shift the sliding-window domain and estimate the pedestal of the signal data within each sliding-window domain to determine an estimated pedestal over the at least a portion of the data domain. The instructions are further configured to cause the processor to subtract the estimated pedestal from the signal data to yield a pedestal-free representation of the signal data for the at least a portion of the data domain and output the pedestal-free representation of the signal data for the at least a portion of the data domain to at least one of a communication device, a display, a printing device, or a data storage device.

In another aspect of the present concepts, a computer readable memory is provided with instructions configured for execution by a processor, the instructions being configured, upon execution by a processor, to obtain a representation of signal data over a data domain. The instructions are further configured, upon execution by a processor, to position a sliding-window over a portion of the signal data. The portion of the data domain within the sliding-window corresponds to a sliding-window domain. The instructions are still further configured, upon execution by a processor, to analyze the signal data within the sliding-window domain to detect the presence of a signature multiplet and, based on the analysis of the data, estimate the pedestal of the signal data within the sliding-window domain. The instructions are additionally configured, upon execution by a processor, to iteratively shift the sliding-window over at least a portion of the data domain to correspondingly shift the sliding-window domain and estimate the pedestal of the signal data within each sliding-window domain to determine an estimated pedestal over the at least a portion of the data domain. The instructions are further configured, upon execution by a processor, to subtract the estimated pedestal from the signal data to yield a pedestal-free representation of the signal data for the at least a portion of the data domain and output the pedestal-free representation of the signal data for the at least a portion of the data domain to at least one of a communication device, a display, a printing device, or a data storage device.

In yet another aspect of the present concepts, a signal processing system is provided and comprises a processor, at least one I/O device operatively associated with the processor, and a memory device bearing instructions configured for execution by a processor to cause the processor to identify a plurality of features from signal data by identifying a plurality of local maxima and local minima of the signal data and defining each feature by a local maxima bounded between two local minima. The instructions are also configured to cause the processor to compute a metric for each of the plurality of features and compare each metric with a metric threshold to determine whether a corresponding feature is a signature feature. The instructions are further configured to cause the processor to identify one or more feature-sets by grouping adjacent signature features and estimate the pedestal for each feature-set. The instructions are still further configured to cause the processor to subtract the pedestal for each feature-set from the signal data to yield a pedestal-free representation of the signal data and output the pedestal-free representation of the signal data for the at least a portion of the data domain to at least one of a communication device, a display, a printing device, or a data storage device.

The above summary of the present invention is not intended to represent each embodiment, or every aspect, of the concepts disclosed herein, such as by the appended figures and the following detailed description.

Figure 1:
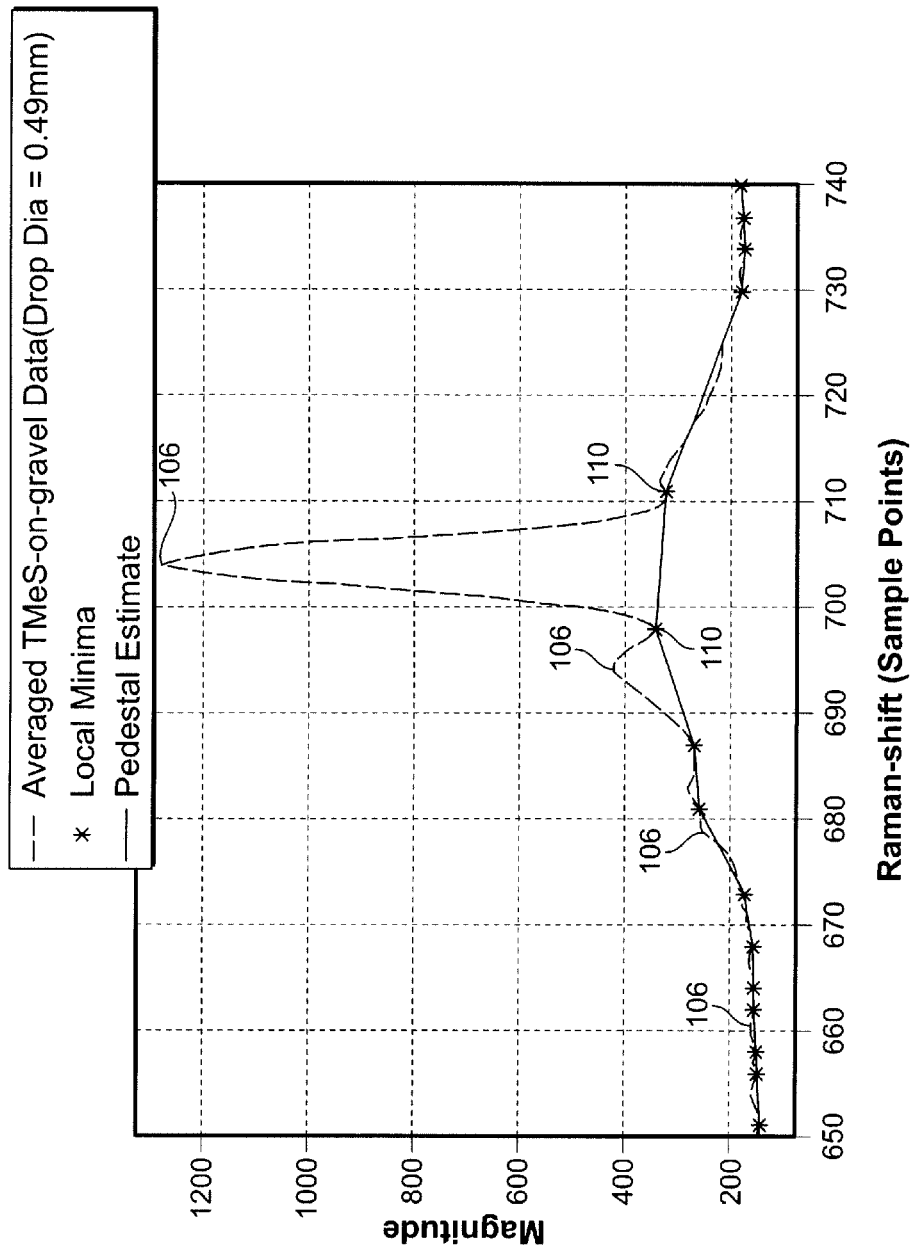
FIG. 1 is a plot of a linear interpolation pedestal estimation (LIPE) pedestal estimate in accord with at least some aspects of the present concepts.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DESCRIPTION OF ILLUSTRATIVE EMBODIMENTS

A high signal-to-interference-and-noise ratio (SINR) is beneficial for the performance of a Raman spectroscopy detector. Besides the chemical concentration, the SINR of a chemical's Raman spectrum is dictated by several factors: primarily, (a) variability in fluorescence of the arbitrary background and/or the target chemical; (b) the instrument-specific impulse response represented by an instrument response curve (IRC); (c) additive noise; and (d) interference from everything other than the target chemical. The first two signal degradation factors collectively raise the spectral data non-uniformly across the spectrum causing it to appear to be placed on a "pedestal." As used herein, the term "pedestal" refers to a rise in the spectrum, whereas the term "background" refers to the physical environment that contains the chemical being irradiated. The pedestal is the most dominant source of signal degradation. Disclosed herein are three exemplary algorithms for detecting and identifying chemical Raman signatures in Raman shift data referred to herein as linear interpolation pedestal estimation (LIPE), sliding-window technique for pedestal estimation (SWTPE), and feature-metric algorithm (FMA).

In order to estimate the pedestal, it is necessary to understand its general behavior. Referring to FIG. 1, the pedestal can be characterized as the lower envelope of the data. Also, it is reasonable to assume that the envelope is slow varying with respect to the wavenumber ($cm^{-1}$) axis because it is known that the fluorescence spectrum is broadband in nature. An approximation to the pedestal (shown as a solid line in FIG. 1), therefore, can be obtained via linear interpolation on a set of local minima points, *, in the data. These local minima points, *, identify the base points of spectral peaks (e.g., 106 in FIG. 1); therefore, two consecutive local minima points, *, define the extent of a spectral peak 106 on the wavenumber axis. For example, a spectral peak located at between 700 and 710 on the Raman-shift axis is defined by two base points 110. Overlapping peaks, called multiplets, are accordingly defined to be made up of several peaks 106, each with two base points.

The guiding principle of this operation stems from the fact that the base of a given spectral peak 106 (not part of a multiplet) is zero for a fairly smooth and pedestal-free Raman signature. In a measured spectrum with pedestal, therefore, any non-zero magnitude at the base points would solely be the result of fluorescence. From the assumption that fluorescence is slow varying, it can be assumed that the derivative of the fluorescence does not vary significantly within the span of the spectral peak 106. A reasonable estimate of the pedestal at all intermediate sample points within the span of the peak 106, therefore, may be obtained by linearly interpolating between the two base points. The assumption that the derivative of the fluorescence does not vary significantly within the span of the spectral peak 106 may not always be true. Spectral data exhibiting fluorescence that significantly increases one end of a peak more than the other do exist. As long as the derivative of the fluorescence is smaller than the derivative of the data, nonetheless, the assumption will be true, thereby, greatly simplifying the solution to the fluorescence problem.

To estimate the pedestal based on the described approach, the two base points of a peak are identified. It is contemplated that any suitable means for identifying the peak locations and base points may be employed. One example of an identification technique to identify both the peak location and base points, involving use of the difference of the spectral data, is described below. The difference of a data curve changes sign (or touches/crosses zero with respect to the sample number axis) from negative to non-negative when the data at the zero-touching/crossing sample point is a local minima, *. On the other hand, the difference of a data curve changes sign from positive to non-positive when the data at the zero-touching/crossing sample point is a local maxima 106. Using this information, both local minima, *, and local maxima 106, collectively referred to as local extrema, can be identified. Accordingly, the local extrema are identified in two steps. First, the difference of the spectral data is computed according to equation 1 and equation 2.

$$d(n)=\text{data}(n+1)-\text{data}(n), 1\leq n<N \quad \text{(Equation 1)}$$

$$d(N)=\text{data}(N) \quad \text{(Equation 2)}$$

where data is an N-point spectral data, d is an N-point difference of data and n is the sample number.

Second, the zero-touchings/crossings of the difference are identified and classified as local minima or local maxima based on the direction of sign change according to equation 3 and equation 4.

$$\text{If } d(n-1)>0 \text{ and } d(n)\leq 0, \text{ then data(n) is a local maximum.} \quad \text{(Equation 3)}$$

$$\text{If } d(n-1)<0 \text{ and } d(n)\geq 0, \text{ then data(n) is a local minimum.} \quad \text{(Equation 4)}$$

Figure 2:
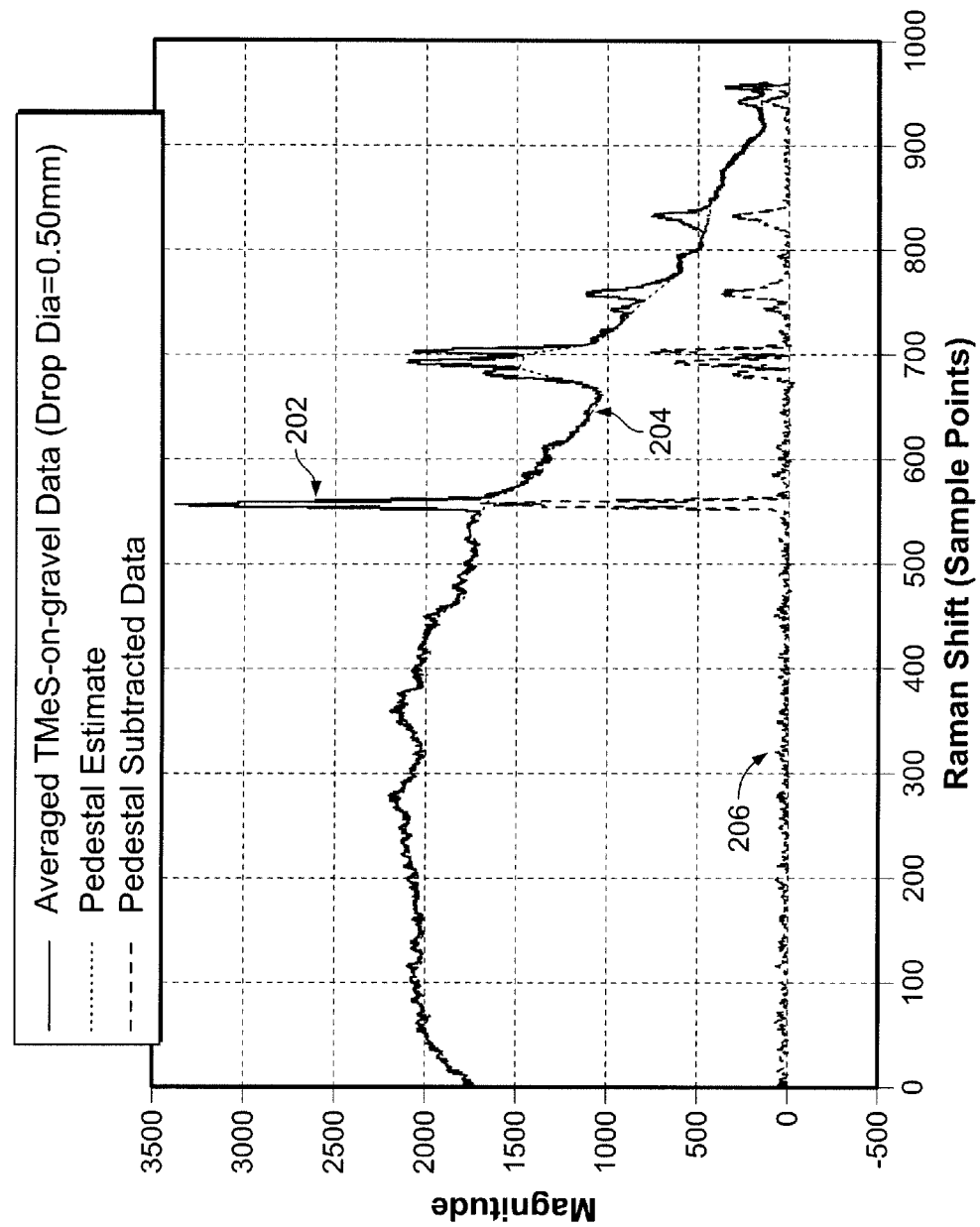
FIG. 2 is a plot of a spectra overlaid with its LIPE pedestal estimate and the pedestal free spectrum in accord with at least some aspects of the present concepts.

If the first local extreme point is not a local minimum, then the first sample point of the data is forced to be a local minimum and if the last local extreme point is not a local minimum, then the last sample point of the data is forced to be a local minimum. This ensures that the spectral peaks at the ends of the spectrum have two base points. The technique of computing the pedestal estimate as an approximation to the lower envelope of a given spectrum by using the above described technique of identifying base points of spectral peaks is called "linear interpolation pedestal estimation" (LIPE). Subtracting the pedestal estimate then yields a pedestal-free spectrum. FIG. 1 shows a region of the spectrum of TMeS-on-glass data (averaged over 100 spectra corresponding to drop diameter of 0.49 mm) as a dashed line, with local minima points, *, and the LIPE pedestal estimate as a solid line. FIG. 2 shows the average of 100 TMeS-on-gravel (drop diameter=0.49 mm) spectra 202, while the LIPE pedestal estimate as a 204. The pedestal-free spectrum 206 is obtained by subtracting the spectrum curve 202 from the LIPE pedestal estimate 204.

In subtracting the pedestal estimate 204 from the spectrum 202 some peaks may be horizontally shifted because the pedestal estimate 204 is not always parallel to the horizontal axis. This shift of peaks is a reverse effect of the pedestal on the peak locations. Therefore, pedestal subtraction approximately restores peak positions.

The presence of additive noise adversely affects the pedestal estimate because it introduces rapid variations in the data, resulting in the introduction of many small-amplitude spectral peaks. A spectral peak in the presence of additive noise, therefore, will appear to be made up of several smaller peaks, which in turn will have their own local minima. Consequently, LIPE will estimate the pedestal at these local minima as their respective magnitudes. These estimates, however, may be incorrect because these local minima are due to additive noise and not to the chemical's Raman signature. The difference spectrum, obtained by subtracting LIPE pedestal estimate of a noisy spectrum from the spectrum, results in the reduction or near truncation of spectral peaks that are representative of the chemical's Raman signature.

Additive noise can be mitigated by the use of averaging or lowpass filtering to yield a smooth spectrum that is more suitable for effective pedestal estimation via LIPE. Averaging several signals, collected by irradiating the same area (matter), is the preferred way of obtaining a smooth spectrum that is representative of that area's Raman signature, though any other suitable means of smoothing is contemplated. For example, the real-time operational requirements on present laser interrogation of surface agent (LISA) instruments allots 2 seconds to the detection algorithm within which it has to process the data and read out its result. Where a laser transmitter operates at a frequency of 25 Hz (i.e., 25 laser pulses are generated/outputted in one second) and fifty spectra are recorded over the period of 2 seconds because each laser pulse causes one return pulse for measurement. The number of spectra used for averaging (N), because of the operational requirements, has to be less than 50 for such an instrument. Several numbers of spectra, (e.g., N=5, 10, 15, 20, and 25) can be averaged and processed by various suitable techniques.

Averaging 25 spectra yields a significantly smoothed spectrum; however, not sufficiently smooth for effective pedestal estimation via LIPE. The inadequacy in smoothing by averaging, due to the constraint on the number of spectra that can be averaged, has to be supplemented by a low-pass (LP) filter. Nonlimiting examples of suitable LP filters include wavelet-defined filters, moving-average (MA) filters, and lowpass filters in the dual-domain.

Averaging N spectra to obtain a smooth spectrum is justified when all N spectra are obtained from the same matter. Among the N spectra, however, if there are more spectra that contain the background's Raman signature than that of the chemical, then averaging all the N spectra will reduce the relative strength of the chemical's signature in the resulting average. LISA instruments are often mounted on vehicles that travel at a certain speed when the instrument is operating. In such a scenario, irradiating the same area until N spectra are collected is not only highly difficult but also undesirable because of the operational issues involved. Each spectrum, therefore, may have to be processed separately without any averaging operation.

Statistically, averaging is a smoothing operation. By considering averaging and LP filtering as a system of two blocks in cascade, an equivalent "single spectrum processing" (SSP) filter may be derived. The following analysis is a general treatment of digital signal processing concepts and, therefore, the terms "frequency" and "signal" are used instead of "dual-domain" and "spectrum", respectively.

Figure 3:
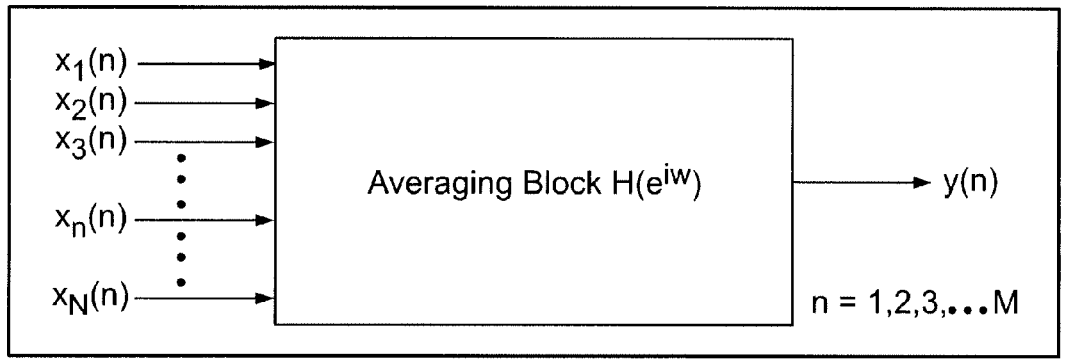
FIG. 3 is a diagram of an averaging block multi-input-single-output (MISO) system in accord with at least some aspects of the present concepts.
Figure 4:
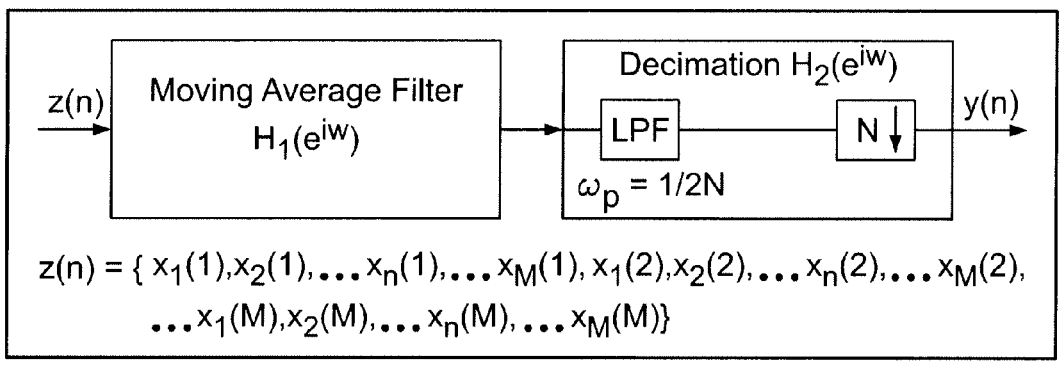
FIG. 4 is a diagram of a single-input-single-output (SISO) system that is equivalent to the MISO system shown in FIG. 3.

FIG. 3 shows an N-spectra-averaging block, where $x_i(n)$ represents the $n^{th}$ sample point, n=1, 2, M, of the $i^{th}$ input signal, where i=1, 2, 3, N, and y(n) represents the output of the averaging block. This is a multi-input-single-output (MISO) system. An equivalent single-input-single-output (SISO) system can be represented by using a MA filter of length N and a decimator of order N. The input to this SISO system needs to be rearranged; all $n^{th}$ samples from the N different signals are grouped together and a new input vector z(n) of length NM is defined. FIG. 4 shows this equivalent SISO system.

The overall frequency response, $H(e^{j\omega})$, of the SISO system is the product of the frequency responses of the two blocks in series. If the frequency response of the SISO MA filter is denoted as $H_1(e^{j\omega})$ and the frequency response of the decimator as $H_2(e^{j\omega})$, then $$H(e^{j\omega})=H_1(e^{j\omega})H_2(e^{j\omega}).$$ (Equation 5)

The response $H_2(e^{j\omega})$ is determined by the anti-aliasing filter, which has a passband width ($\omega$p) of $\pi/2N$ rads/sec. Thus, for ideal decimation by N, $H_2(e^{j\omega})$ is 0 beyond $\pi/2N$ rads/sec. In particular, for N=25, $$H_2(e^{j\omega}) = \begin{cases} 1, & 0 \text{ rads/sec} \leq \omega \leq 0.02\pi \text{ rads/sec} \\ 0, & 0.02\pi \text{ rads/sec} < \omega \leq \pi \text{ rads/sec} \end{cases}$$ (Equation 6)

The equivalent SSP-filter will have a dual-domain response given by the product of the dual-domain responses of the averaging operation and the LP filter. The product, however, will be the response of the averaging operation because it is the one that has a smaller passband width and zero elsewhere. The above mathematical analysis assumes that the anti-aliasing filter is ideal. The effect of such an assumption is the introduction of ripples. The transition band, therefore, is widened to extend to the end of the dual-domain axis (u=1). The final dual-domain response of the SSP-filter, $h_6(u)$, is given in equation (Equation 7):

$$h_6(u) = \begin{cases} 1, & 0 \leq u \leq 0.02 \\ e^{-6.9078(u-0.02)}, & 0.02 < u \leq 1 \end{cases}$$ (Equation 7)

Having addressed the pedestal and additive noise, the effects of the IRC and interference are now described.

The IRC contributes to the pedestal and also causes edge effects, which are deformed spectral features of steep assent and descent at the ends of the spectral range. The pedestal effect of the IRC is addressed by LIPE; however, the edge effects are not addressed. Recovering the spectral features towards the ends of the spectrum, therefore, improves the SINR further. The presence of a relatively strong spectral peak at approximately 2930 $cm^{-1}$ in certain chemicals because of a CH stretch, and the importance it plays in distinguishing chemicals, makes IRC correction all the more necessary.

The IRC, as a measured transfer function, has a multiplicative effect on the incoming spectral data. Correction for instrument effects is achieved, therefore, by dividing the spectral data with the IRC; however, the measured IRC is noisy and the resultant quotient spectrum acquires the noise.

This problem can be addressed by smoothing the measured IRC using, for example, a MA filter (l=31).

Figure 5:
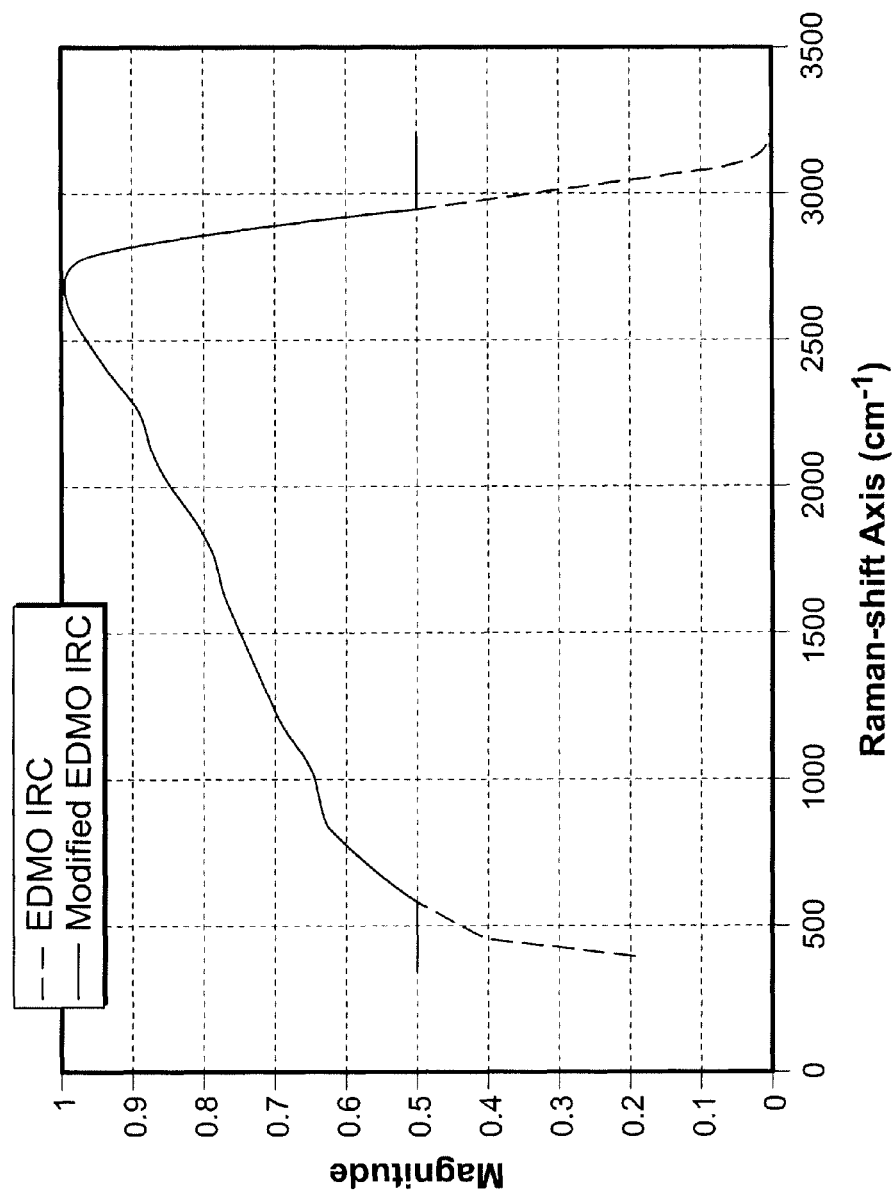
FIG. 5 is a plot of a modified instrument response curve (IRC), which represents an instrument's impulse response in accord with at least some aspects of the present concepts.

Division of a given spectrum by the smoothed IRC, however, is not straightforward because the wavenumber vector (non-linearity information) corresponding to the IRC does not always match with that corresponding to the spectrum. The IRC values at the wavenumbers corresponding to the spectrum, therefore, have to be interpolated. As seen in FIG. 5, a IRC, shown as a dashed line, further has very low values towards the ends of the spectrum causing disproportionate amplification in that region in the quotient spectrum. In order to avoid such amplification, those IRC values that are lower than 0.5 are substituted by a value of 0.5 rendering a modified IRC, shown as a solid line.

According to some aspects, the process for addressing the IRC can be summarized as including the steps of interpolating the IRC to match the wavenumber vector of the spectrum to be corrected, smoothing the IRC via, for example, a MA filter (l=31), and modifying the IRC such that the magnitude of the IRC is held at 0.5 at all sample points that have a magnitude less than 0.5.

Interference from spectral peaks of non-target-chemical matter is also a major cause of poor detection performance. This problem can be addressed by truncating the interfering peaks, as they mask the Raman signature irreversibly. A spectral peak may be truncated by locating its base points and connecting them by linear interpolation. The base points may be located by identifying the two local minima, one on either side of the peak via, for example, the technique described above with respect to equations 1-4. Specifically, the nearest local maximum in the vicinity (within a range of $\pm 10 \text{ cm}^{-1}$) of the wavenumber corresponding to the interfering peak's local maximum (available from Table 1, presented below) is identified, and the base points as the two nearest local minima (in either direction with respect to the wavenumber axis) are identified.

Figure 6:
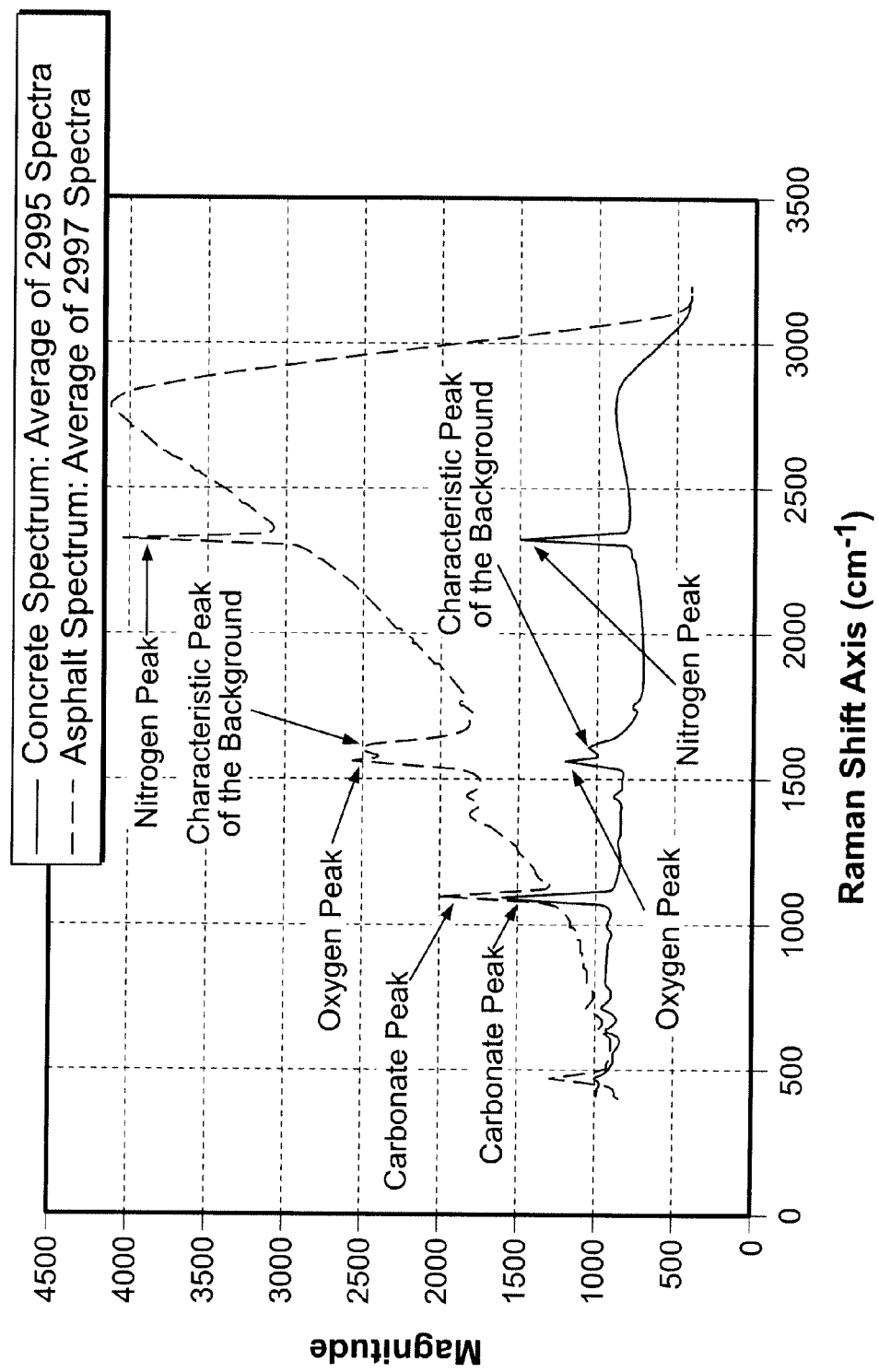
FIG. 6 is a plot of a spectra of concrete and asphalt showing interfering peaks in accord with at least some aspects of the present concepts.

Different backgrounds have several interfering peaks at different wavenumber locations as demonstrated in FIG. 6. If the chemical and the background are known in advance, then only those peaks of the background that do not overlap with the signature of the chemical may be truncated without the worry of truncating the characteristic peaks of the chemical. However, information about the chemical or the background is generally not known in advance, making it difficult to choose which peaks to truncate among the entire set of interfering peaks without losing chemical information.

It was observed by the inventors that certain interfering peaks (e.g., the Nitrogen peak shown in Table 1) do not overlap with Raman signatures of any chemical in the library set. Such peaks may be truncated with the assurance that no chemical information will be lost. On the other hand, interfering peaks that overlap with Raman signatures of one or more chemicals pose a difficult discrimination problem (e.g., the asphalt/concrete peak in FIG. 6 overlaps with the TMeS Raman signature). A solution for this problem is to truncate the interfering peak(s) altogether from both the measured and the library spectra. The correlation coefficient will then provide a quantitative measure of closeness in the remainder of the spectral region.

Truncation of the interfering peaks is performed based on their locations on the wavenumber axis, which are known beforehand from the respective backgrounds library spectra. Table 1 provides information on four interfering peaks. The last column lists the chemicals whose Raman signature overlaps with these interfering peaks. Note, however, that only the chemicals of interest are considered instead of the entire set of chemical library in the table below. The peak locations of Table 1 are obtained from the average spectrum (2995 spectra) of concrete in Dataset 4 and the air library spectrum. Dataset 4 included 1024-point spectral measurements of five chemicals by an EDM0 instrument. The chemicals in Dataset 4 are designated Chemical_A, Chemical_B, Chemical_C, Chemical_D, and Chemical_E and the measurements are rid of any backgrounds such as concrete or asphalt, but are interfered by an air signature. Dataset 4 also comprised spectral signatures of moving concrete and moving asphalt.

TABLE 1

| Interfering peaks | | | | |
|---|---|---|---|---|
| Sl. No. | Peak name | Peak location ($cm^{-1}$) | Source of the peak | Overlaps with |
| 1 | Carbonate | 1090 | Asphalt or Concrete | Chemical_A, Chemical_E, and TEPO |
| 2 | Oxygen | 1555 | Air | Chemical_A |
| 3 | Asphalt/Concrete | 1605 | Asphalt or Concrete | TMeS |
| 4 | Nitrogen | 2330 | Air | None |

Figure 7:
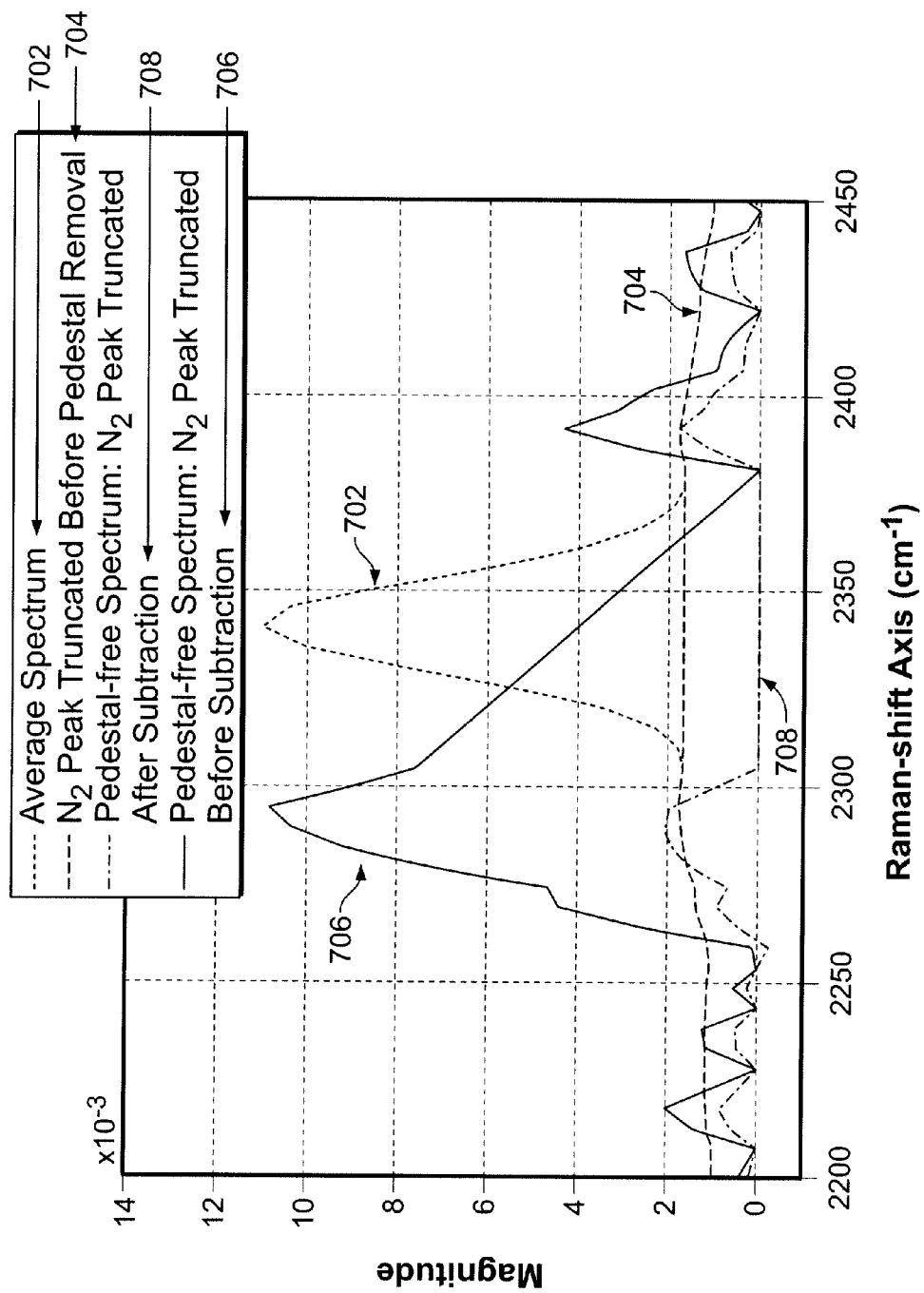
FIG. 7 is a plot illustrating the effect of peak truncation before and after pedestal removal in accord with at least some aspects of the present concepts.

Finally, truncating peaks involves identifying base points of the peaks. It is important, therefore, to truncate peaks after smoothing the spectrum to minimize the effect of additive noise. Further, truncating a peak before pedestal subtraction would require interpolating between the base points. This will cause the introduction of humps on either side of the truncated peak in the peak-truncated spectrum, which in turn will falsely appear as spectral peaks in the pedestal-free spectrum. This problem is illustrated in FIG. 7, which shows the Nitrogen peak in the average of 25 TMeS-on-glass (drop diameter=0.49 mm) spectra 702, the result of truncating the peak without pedestal subtraction 704, and the pedestal-free spectrum 706 obtained by subtracting the result of truncating the peak without pedestal subtraction 704 from its pedestal estimate. All spectra shown were normalized with respect to energy so that spectral peak magnitudes of different spectra can be compared.

Truncating interfering peaks after pedestal subtraction, on the other hand, will be simpler because no interpolation will be required as the base points are known to be zero. A straightforward replacement of all samples in between the bases with zeroes will be sufficient. The pedestal-free spectrum 708 is obtained by truncating the Nitrogen peak after the pedestal estimate has been subtracted from the spectrum 702. It can be seen that the pedestal-free spectrum 706 also has an undesirable effect of introducing false peaks on either ends of the interfering peak; however, these false peaks also are present in the pedestal-free spectrum 708, but they are low in magnitude.

With all factors degrading the SINR of a Raman-shift data being addressed, a quantitative measure of closeness of two spectra has to be chosen. The correlation coefficient between two spectra provides a quantitative measure of closeness between them. The correlation coefficient, $\gamma(x,y)$, between two vectors, x and y, may be computed by any suitable means such as, for example, by a MATLAB© inbuilt function, corrcoeff(x,y). A simplified equation representing the computation by the function is shown in equation 9:

$$\gamma(x, y) = \frac{E\{(x - \mu_x)(y - \mu_y)\}}{E\{(x - \mu_x)^2\}E\{(y - \mu_y)^2\}} \quad \text{(Equation 9)}$$

where E{ } is the expectation function, and $\mu_x$ and $\mu_y$ are E{x} and E{y}, respectively. It is important that differences in energy levels of the two spectra not affect the measure of closeness because it is the shape of the spectrum that is of interest and not their energy levels. The denominator in equation 9, which is the product of the variances of the spectra, normalizes the correlation coefficient, thereby, making the closeness measure independent of the energy.

In order to make fair comparisons between the measured and the library spectrum, both have to be in the same domain; however, some library spectra have pedestals that invalidate a comparison with a pedestal-free spectrum. All library spectra, therefore, must be processed in the same way the data has been processed. This approach of bringing the two spectra in the same domain for comparisons is justified by the fact that the processing techniques described above provide a one-to-one-mapping between their inputs and outputs, i.e., no two different spectra processed using the techniques discussed thus far will yield the same resultant spectra. Conversely, if two processed spectra match, then they must have come from the same source.

The method of measuring closeness can be streamlined by considering only those sample points in the spectra that contain a chemical signature (i.e., a region of interest on the wavenumber axis may be defined for a given spectrum as the only wavenumber region in which chemical Raman signature is present). However, a set of library spectra of several chemicals is available to compare with the measured spectrum. A wavenumber region of interest (WROI), therefore, for each chemical may be defined. The measure of closeness between the processed spectrum and each library spectrum may then be computed only in the library's WROI. The advantage of correlating only in the WROI is the elimination of the effect of noisy regions on the closeness measure. A comparative study of the results of WROI correlation and full wavenumber range (FWR) correlation is described in greater detail below. It is shown that WROI correlation significantly improves detection performance.

Caution should be exercised, however, in cases where two chemicals in the set of libraries are differentiated only by a few spectral features. In such scenarios, the WROIs of the two chemicals have complete overlap except in the spectral region distinguishing the two chemicals. Correlating in WROI, therefore, leads to higher chances of mismatch of the chemical's identity. In the event of such WROI overlap, the advantage of WROI correlation may still be reaped by first using this technique to classify similar chemicals and then performing additional processing to identify the chemical within a given class.

A detection scheme may be designed to identify a chemical among a set of library chemicals that is closest to the measured spectrum based on the closeness measure. The following is an exemplary step-by-step procedure for processing Trimethylethoxysilane (TMeS) drop data of Dataset 2. Dataset 2 included 960-point spectra drop data of TMeS for drop diameters ranging from 0.49 mm to 2.33 mm on two different backgrounds, glass and gravel, as measured by the Gen-I instrument comprising an intensified charge coupled device (ICCD) made up of 960×256 optical detectors.

For the preliminary detection algorithm, the measured spectra is first smoothed by averaging N (e.g., 5, 10, 15, 25, etc.) spectra. Second, the average spectrum is smoothed further via a suitable LP filter. Third, the spectrum is normalized with respect to energy via division by the sum of the magnitudes. Fourth, the pedestal in the spectrum is estimated via LIPE and subtracted to obtain a pedestal-free spectrum. Fifth, the Nitrogen and Oxygen peaks are truncated from the pedestal-free spectrum. Sixth, the spectrum of step 5 is shifted to the left by 2 points via inserting zeros towards the right end of the primal domain. Seventh, the pedestal of a TMeS library spectrum is estimated via LIPE and subtracted to obtain a pedestal-free library spectrum. The Nitrogen and Oxygen peaks need not be truncated from the library pedestal-free spectrum because they are not present in the TMeS library spectrum. Eighth, the pedestal-free spectrum from step 6 is correlated with the pedestal-free spectrum of step 7, both in the FWR and the WROI to obtain two correlation coefficients. To simplify the evaluation, only air peaks are truncated. Dataset 2, nevertheless, is not interfered with by any other peaks because the background is either glass or gravel. Further, step 6 is performed to account for a lateral shift to the right of the measured spectrum with respect to the library spectrum. One of ordinary skill in the art will appreciate that some of these steps may be performed in a different order from that described above.

The performance of this algorithm is discussed in detail below. Although the performance is reasonably good for drop diameters >1 mm, certain disadvantages of LIPE pedestal estimate subtraction from a spectroscopist's perspective are discussed below along with two alternative estimation techniques that are directed to satisfying the requirements of spectroscopists.

From a detection perspective, as long as the library and measured spectra are processed similarly, good detection rates can be achieved as is supported by the reasonably good LIPE results described in detail below. However, Raman signatures of chemicals most often have at least one set of overlapping peaks. The relative magnitudes of these peaks may be important to a spectroscopist. It is a desired characteristic of any pedestal estimation technique from a spectroscopist's perspective, therefore, to retain overlapping peaks (multiplets) after pedestal subtraction. The LIPE considers multiplets as multiple peaks instead of treating them as a single spectral feature. The disadvantage of this approach is that the local minima resulting from multiplets are forced to have zero magnitude in the pedestal-free spectrum. Subtracting the LIPE pedestal estimate from the measured spectrum, consequently, splits multiplets into individual peaks. Further, the amount of horizontal shift of these individual peaks as a result of subtracting the pedestal estimate is not justified because the pedestal occurrence did not shift the position of these peaks by that amount.

A multiplet can be characterized, in general, as having one or more local minima (as a result of two or more overlapping peaks) between the two local minima (boundary points) that define its width. The boundary points of a multiplet correspond to the left local minimum of the left-most overlapping peak and the right local minimum of the right-most overlapping peak. Further, the two boundary points have nearly the same magnitude due to the assumption that the effect of fluorescence does not vary greatly across the wavenumber range spanning chemical spectral features. This characterization may be used to estimate pedestals with due consideration to the presence of multiplets.

Figures 8A, 8B:
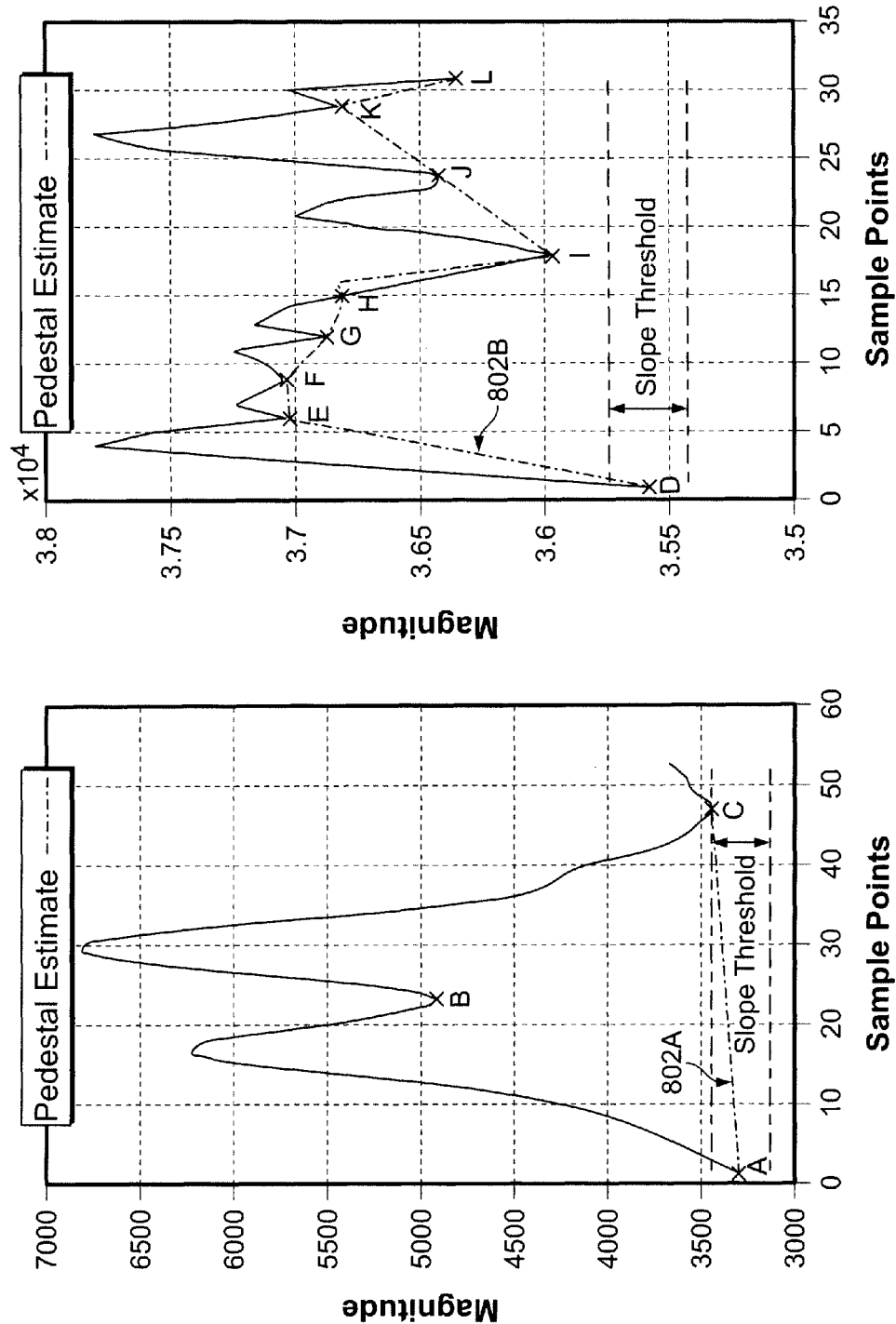
FIGS. 8A and 8B are plots of a criterion-based pedestal estimation technique in accord with at least some aspects of the present concepts.

For example, multiplets may be identified based on a threshold criterion such as the magnitude of the difference between the boundary point values being less than a certain threshold. FIG. 8A shows a spectral region containing a doublet whose boundary points are denoted by A and C, and intermediate local minimum denoted by B. FIG. 8B shows a spectral region that does not contain a multiplet; however, several local minima points are present that are denoted D through L. The dashed lines indicate the maximum difference between the magnitudes of the boundary points allowed in order to consider them as belonging to a multiplet.

If the criterion is met (as in FIG. 8A), then it is indicative that the two boundary points (A and C in FIG. 8A) are indeed that of a multiplet. The pedestal estimate 802A at these points is their respective values, whereas the pedestal estimate 802A between these points is obtained via linear interpolation between the boundary points A and C. On the other hand, if the criterion is not met (as in FIG. 8B), then it is indicative that no multiplets are present within the span of the boundary points (D and L in FIG. 8B). Hence, the pedestal estimate 802B at all local minima (A through I in FIG. 8B), within and including the two boundary points, is their local minima values. The pedestal estimate at all other intermediate sample points is estimated via linear interpolation between the two adjacent local minima similar to LIPE.

Figure 9:
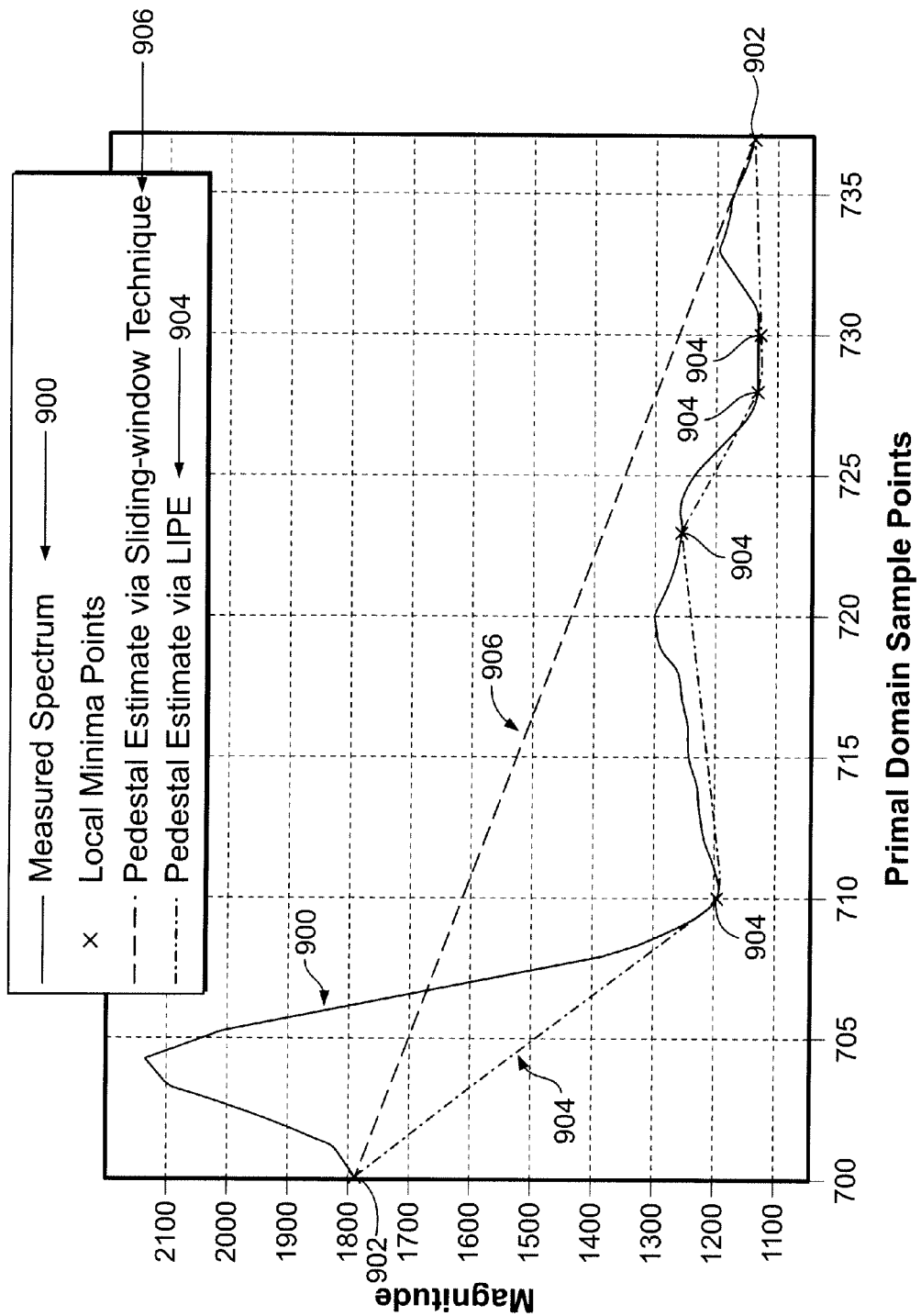
FIG. 9 is a plot of a peak attenuation problem in the criterion-based pedestal estimation technique in accord with at least some aspects of the present concepts.

This method of identifying the presence of a multiplet can sometimes be incorrect. In FIG. 9 for instance, the boundary points 902 of a measured spectrum 900 have a magnitude difference less than the slope threshold; however, all intermediate local minima points 904 have significantly lower values. Using the criterion-based technique to estimate the pedestal will cause the subsequent subtraction of the pedestal estimate to attenuate peaks and yield negative differences. The peak attenuation problem may be addressed by comparing the pedestal estimates obtained via LIPE 904 and the new criterion-based technique 906: if the sum of the magnitudes of the pedestal estimate obtained via LIPE 904 is smaller than that obtained via the criterion-based technique 906, then the criterion-based technique 906 is discarded.

In the criterion-based scheme, the multiplet's width and its wavenumber location should be known beforehand. Chemical library spectra are available beforehand from which such parameters can be known. However, in following such a pedestal estimation technique, the measured spectrum will need to be processed as many times as there are chemical libraries, each time with a different set of parameters obtained from the corresponding chemical library. Such a high cost of processing may be prohibitive.

Figure 10:
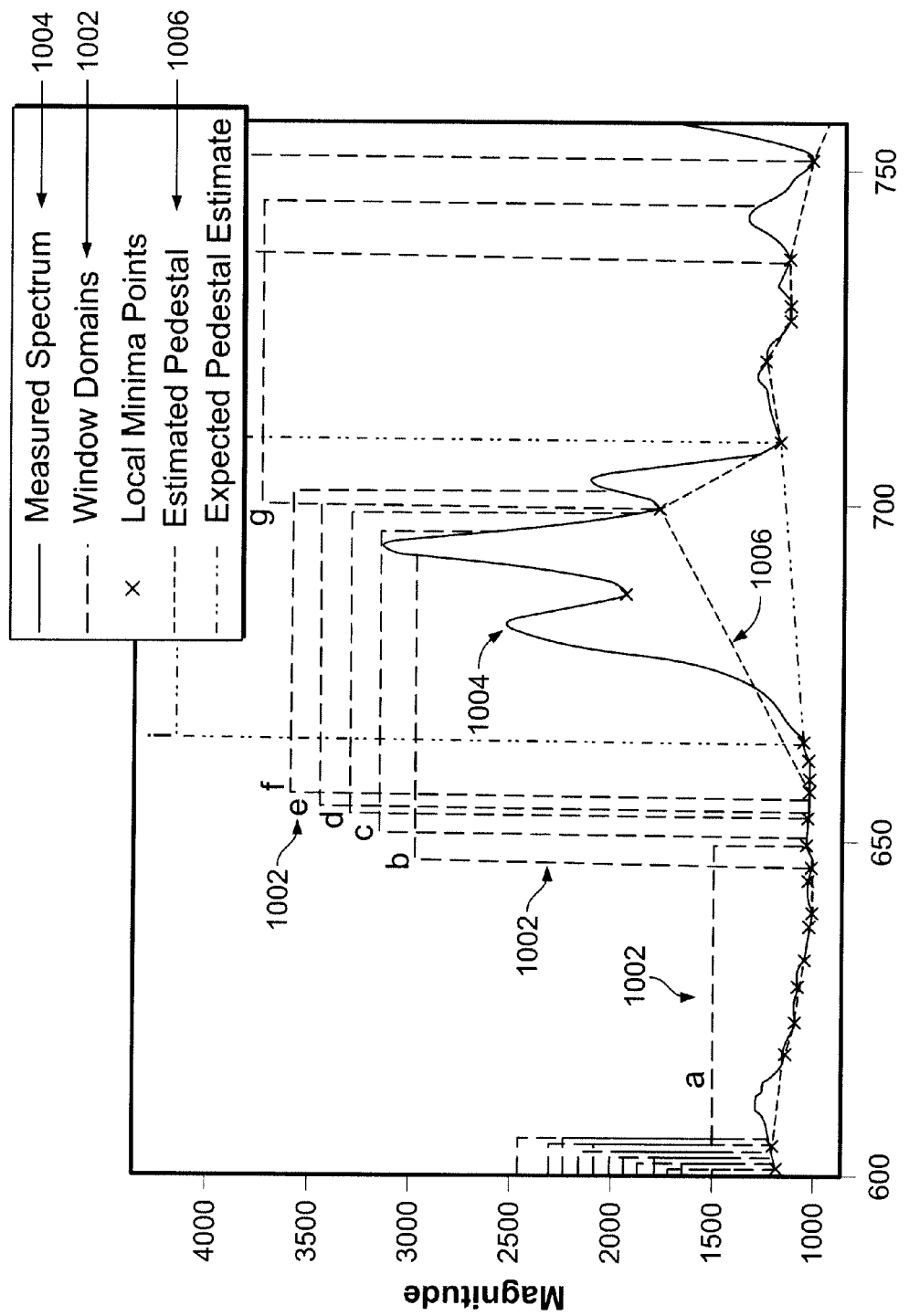
FIG. 10 is a plot of a sliding-window technique of pedestal estimation (SWTPE) in accord with at least some aspects of the present concepts.

A computationally cost effective way of estimating the pedestal is to use a sliding-window technique. FIG. 10 shows several domains of the sliding-window 1002 overlaid on a sample spectrum 1004. The window length is chosen to match the width of the widest multiplet in a given spectrum 1004 (e.g., the window length=46 in FIG. 10). The boundary points are the first and the last local minima within the span of the window 1002. Thresholding and subsequent pedestal estimation are performed within the current window domain as mentioned earlier. If a multiplet is identified, then the next window domain starts from the last local minimum of the current domain (e.g., domain f to domain g in FIG. 10), otherwise it starts from the nearest local minimum to the right (e.g., domain b to domain c in FIG. 10), and so on. The window 1002 is slid until it covers the entire spectrum 1004. It is important to note that the nearest local minimum to the right is one that is nearest to either the left or the right edges of the window 1002. In other words, after moving the window 1002, one of the two edges occupies the local minimum.

This "sliding-window technique of pedestal estimation" (SWTPE) provides pedestal estimates 1006 that are based on the presence of multiplets. In some scenarios, however, multiplets may still be split into individual peaks after pedestal subtraction. This occurs if any window domain 1002 partially overlaps a multiplet and the criterion for the presence of a multiplet is met (e.g., domain f in FIG. 10). Such scenarios can be avoided by starting the first window domain 1002 at an appropriate location such that the window domain 1002 overlapping the multiplet does so completely (e.g., hypothetical domain i in FIG. 10); however, the choice of such a location becomes difficult. Hence, several passes of the window 1002 are performed, with each pass starting at a different location, and as many different pedestal estimates 1006 obtained. The number of passes required is limited by the number of local minima points present within the first window domain 1002 of the first pass, because starting at any other local minima point will yield a duplicate pedestal estimate 1006. Finally, the best pedestal estimate 1006 at each sample point is chosen as the minimum of all pedestal estimates 1006 at that sample point.

The SWTPE needs two data/instrument-dependent parameters—the slope threshold and the sliding-window's length. The choice of these parameters is critical for accurate pedestal estimation. A robust detection algorithm is desired that is also generic enough to work both on different instruments and on a wide variety of input spectral data. Therefore, a technique for dynamically selecting the sliding-window length is pursued so that SWTPE will yield a more accurate pedestal estimate.

Characteristic chemical signature peaks have significantly higher amplitudes than both the pedestal and the additive noise. The derivative or difference of a spectrum, therefore, will have higher magnitudes at sample points corresponding to chemical signature features than at sample points corresponding to other components like the background or additive noise. Likewise, the standard deviation across all sample points of a given energy-normalized spectrum, in general, indicates the strength of the signature: a higher standard deviation indicates a stronger signature. When the noise is large and the chemical signature is small, however, the standard deviation although high might not be representative of the chemical's signature. Most chemical signatures in the dataset, nonetheless, are reasonably high SINR data allowing the use of the standard deviation as a measure of the chemical signature's strength. Some effects of using this measure, however, do exist and will be discussed below in further detail. Using these two metrics—the difference and the standard deviation—an ad hoc method of selecting the sliding-window's length based on the spectral data being processed is presented in the following. First, the difference of the spectrum is computed. Second the local minima points across the given spectrum are identified via identification of zero-crossings of the difference. Third, all sample points at which the magnitude of the difference is greater than a present threshold are identified. Fourth, for every sample identified in step 3, the two adjacent local minima points on either side are identified. The span of the local minima points give the span of the peak to which they correspond. Fifth, all adjacent peaks identified in step 4 are grouped, thereby obtaining a peak-set that is likely to represent a multiplet. The span of each peak-set, defined as the difference between the end and the start sample points of the peak-set, is the span of the window that completely encompasses it. Sixth, the width of the widest peak-set among all peak-sets of step 5 is chosen as the SWTPE's sliding-window length. One of ordinary skill in the art will appreciate that some of these steps may be performed in a different order than is described above.

Figure 11:
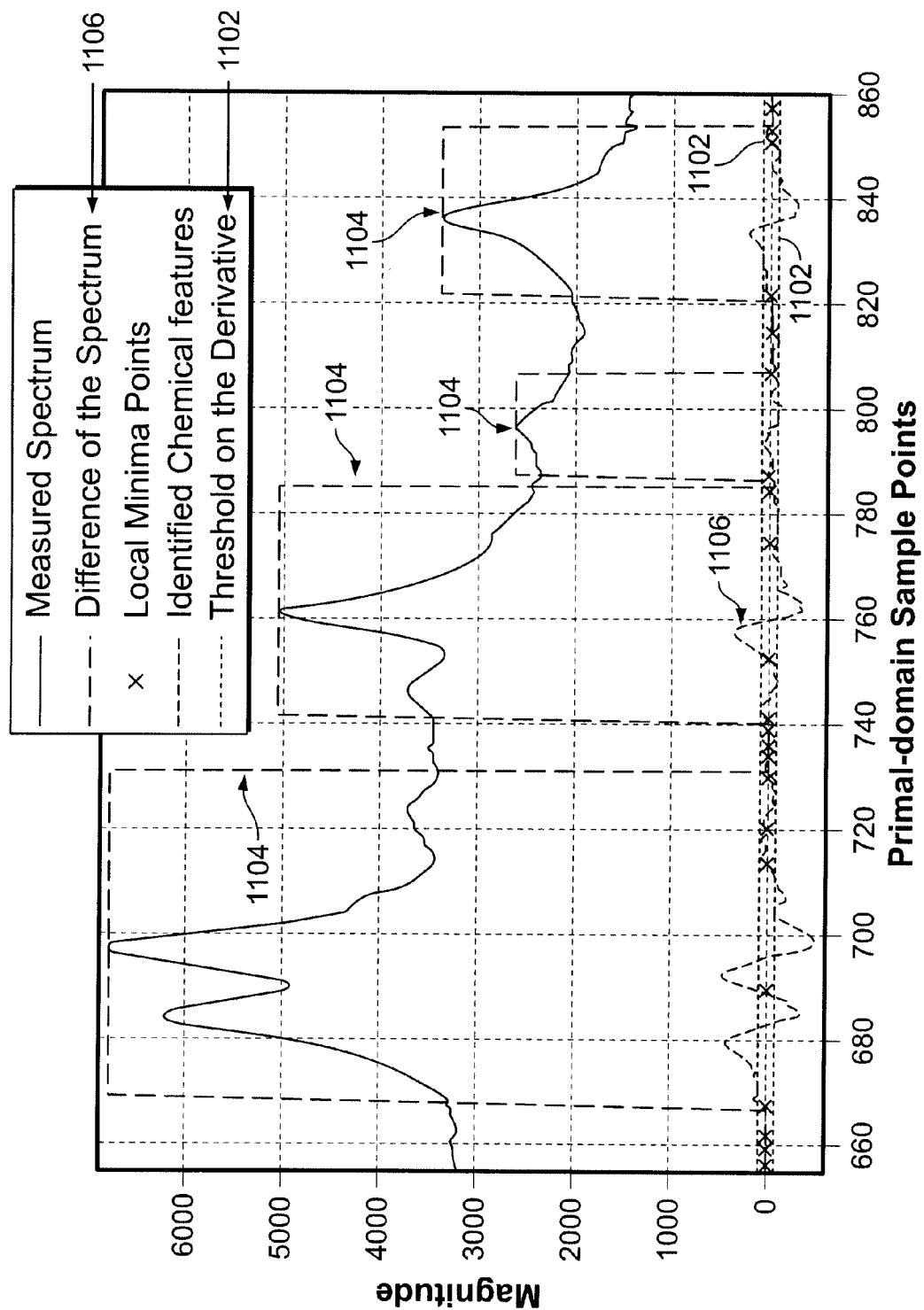
FIG. 11 is a plot of a dynamic window-length-selection technique in accord with at least some aspects of the present concepts.
Figure 12A:
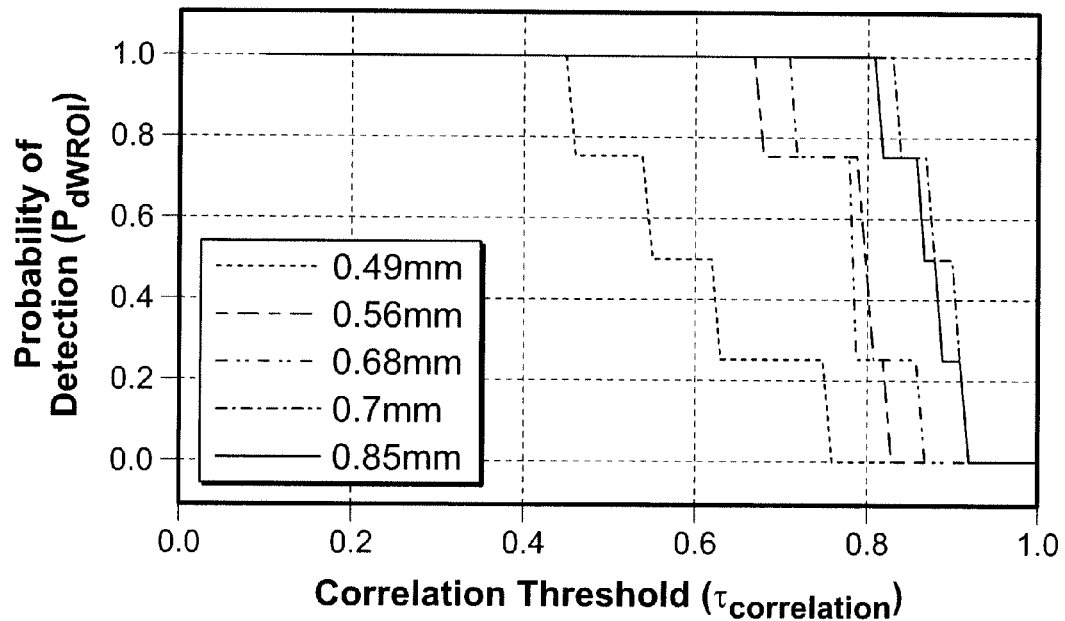
FIGS. 12A-D are plots of LIPE performance on TMeS (trimethylethoxysilane)-on-glass data for N=25 in accord with at least some aspects of the present concepts.
Figure 12B:
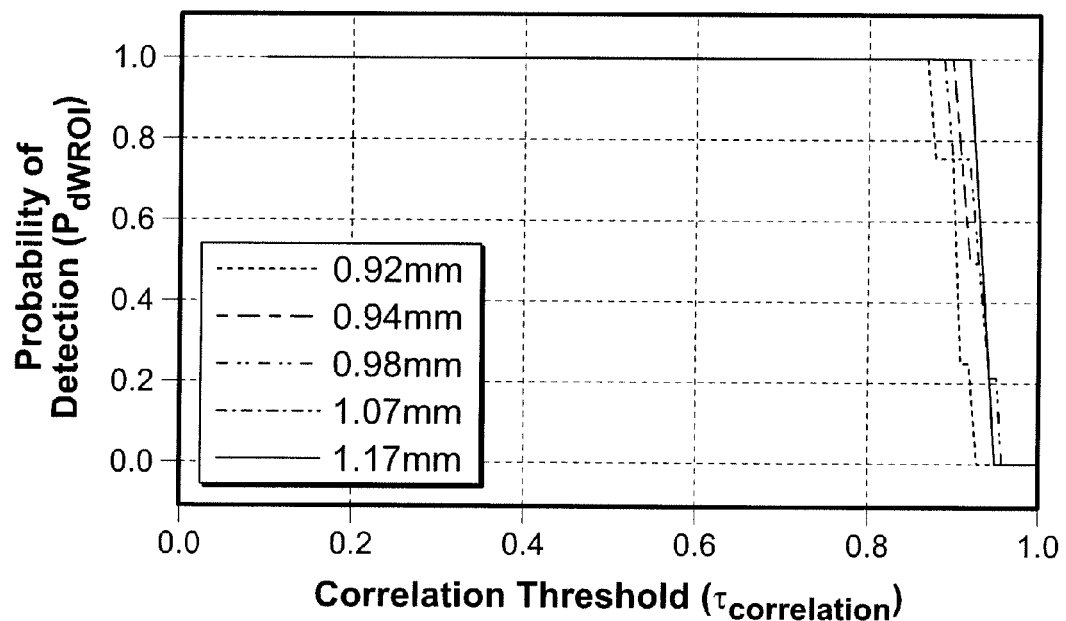
Figure 12C:
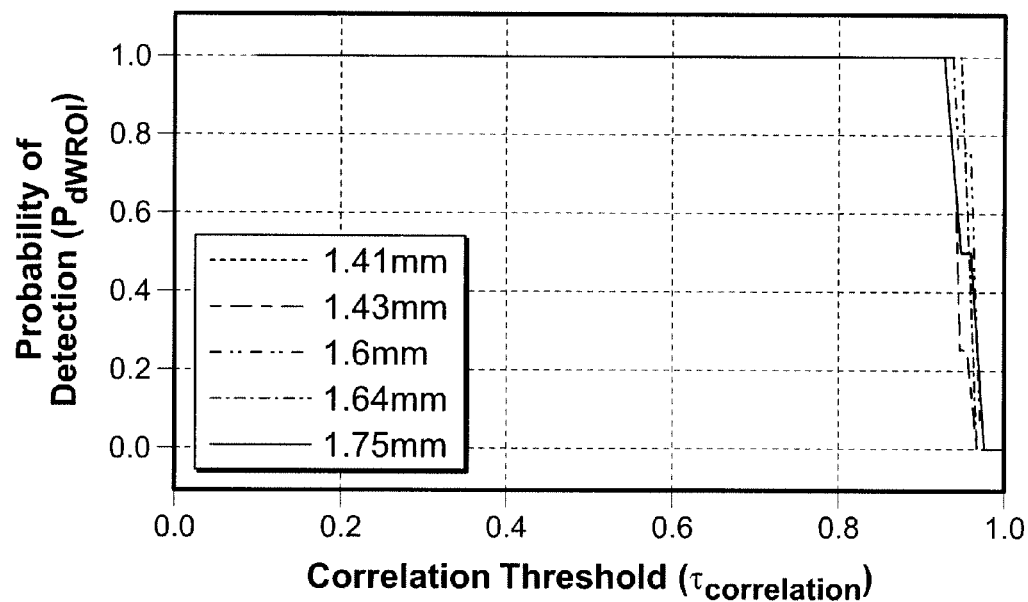
Figure 12D:
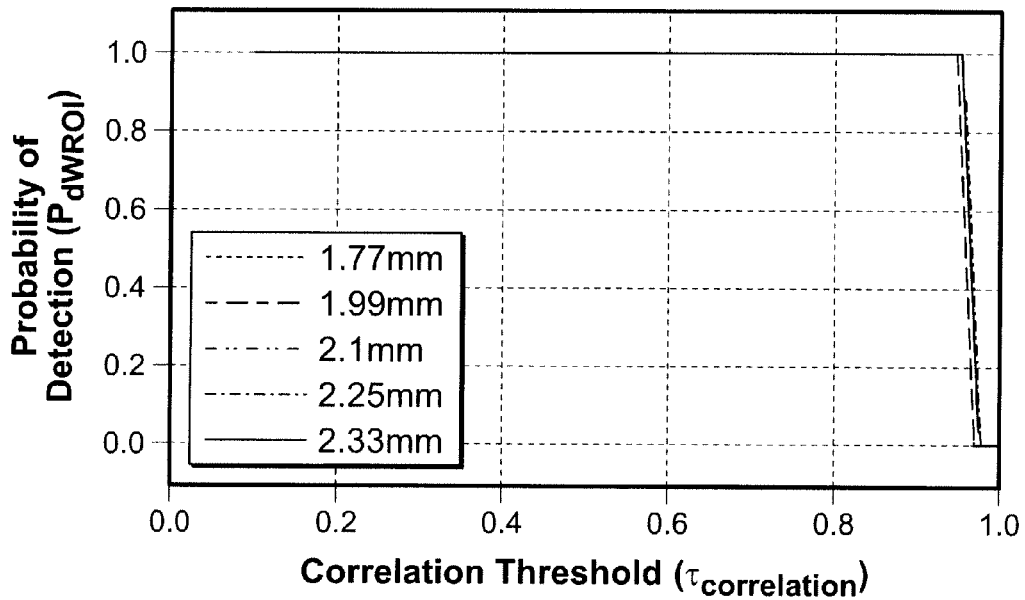
Figure 13A:
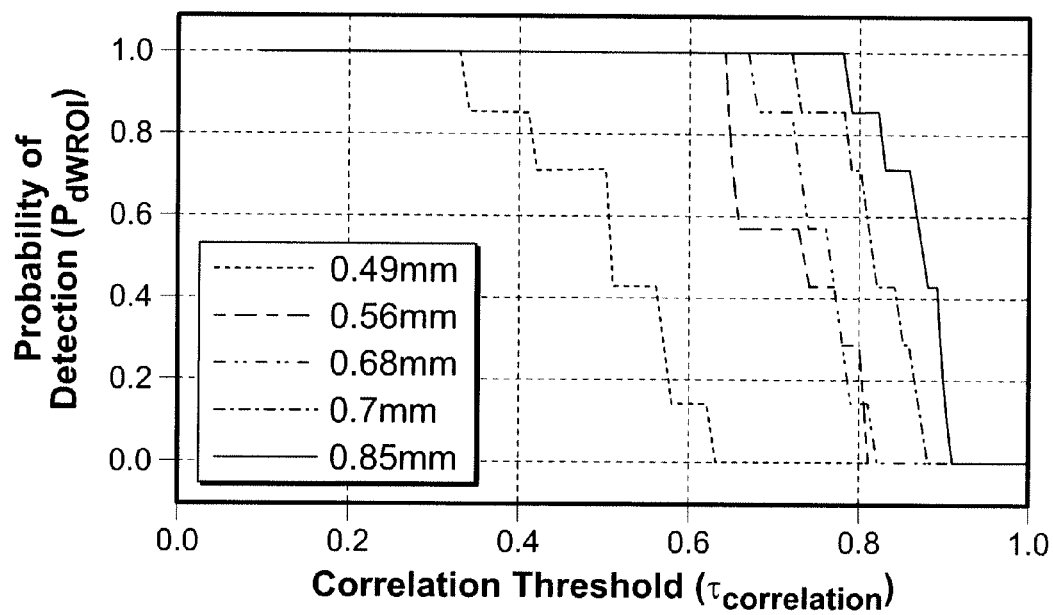
FIGS. 13A-D are plots of LIPE performance on TMeS-on-glass data for N=15 in accord with at least some aspects of the present concepts.
Figure 13B:
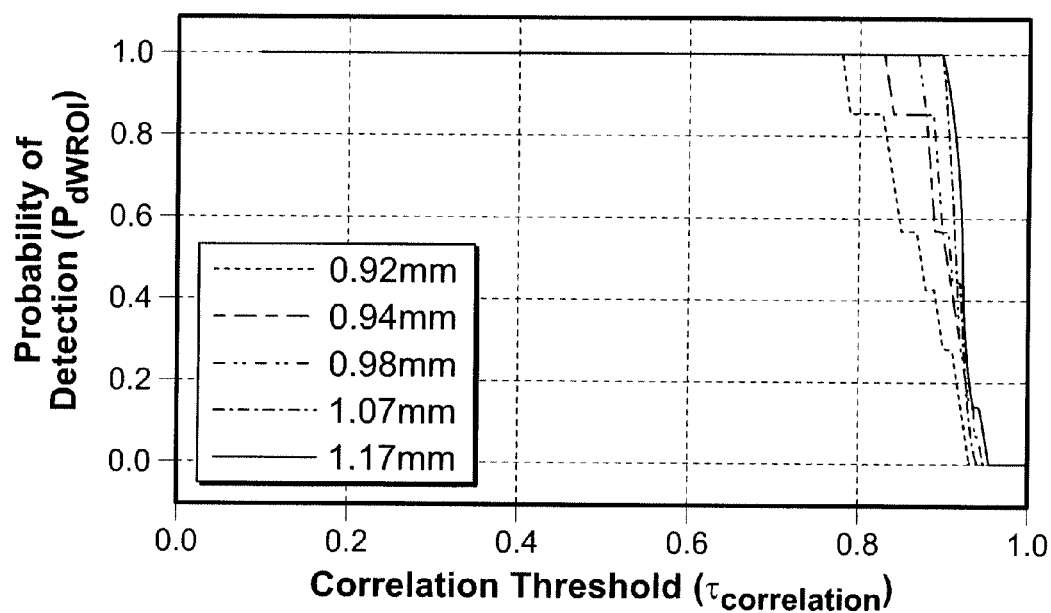
Figure 13C:
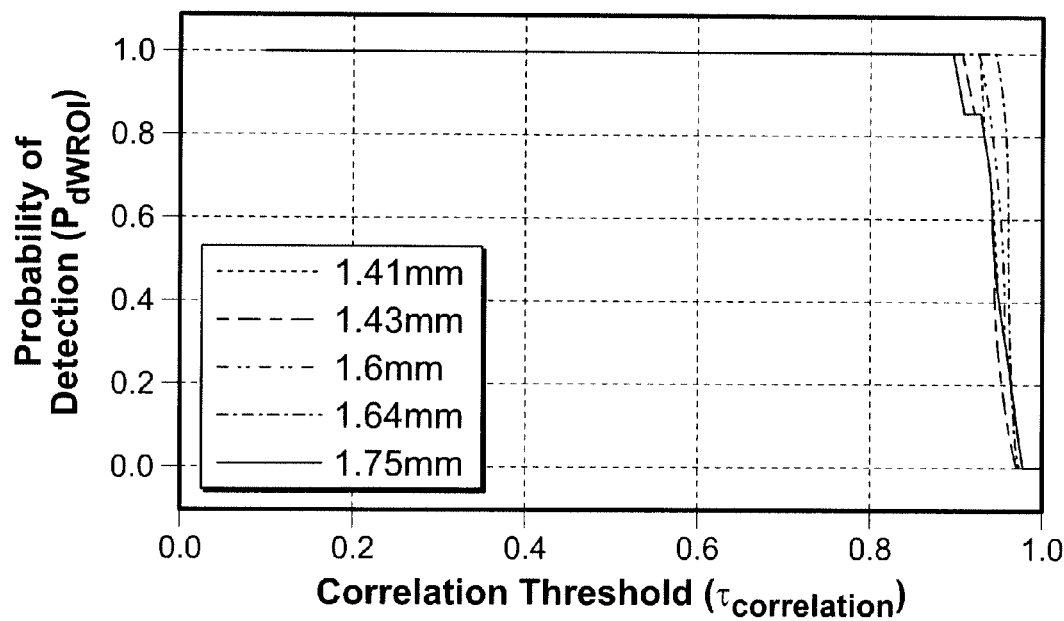
Figure 13D:
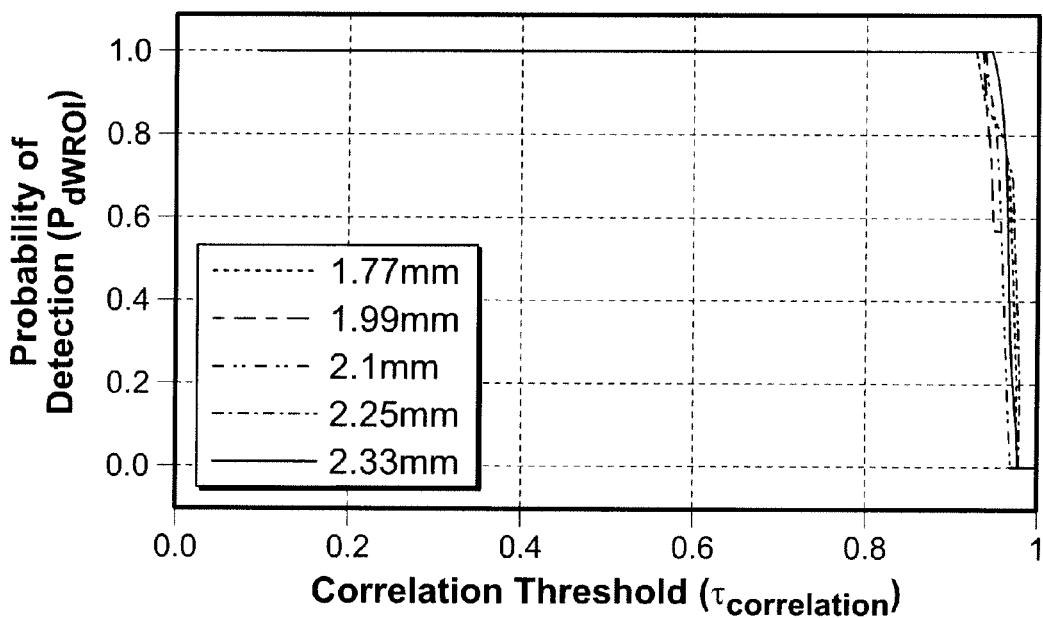
Figure 14A:
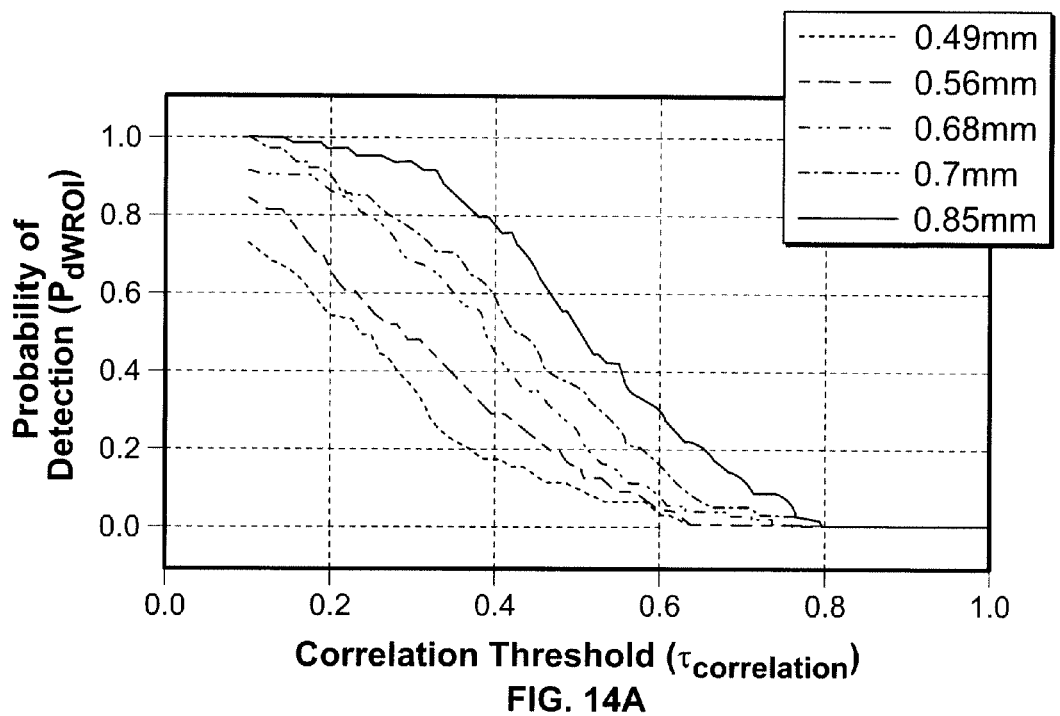
FIGS. 14A-D are plots of LIPE performance on TMeS-on-glass data for N=1 in accord with at least some aspects of the present concepts.
Figure 14B:
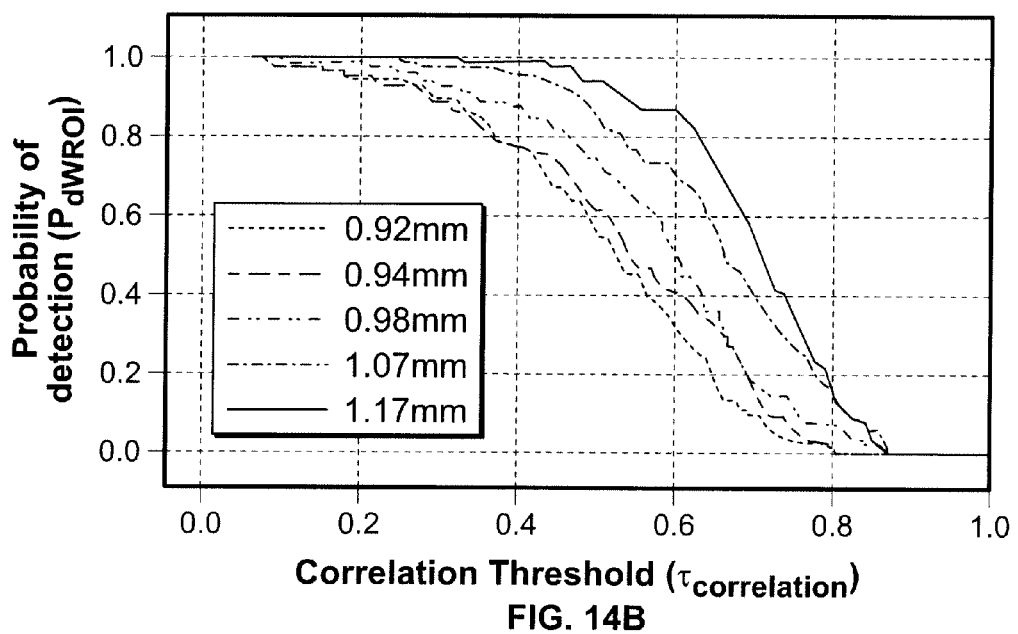
Figure 14C:
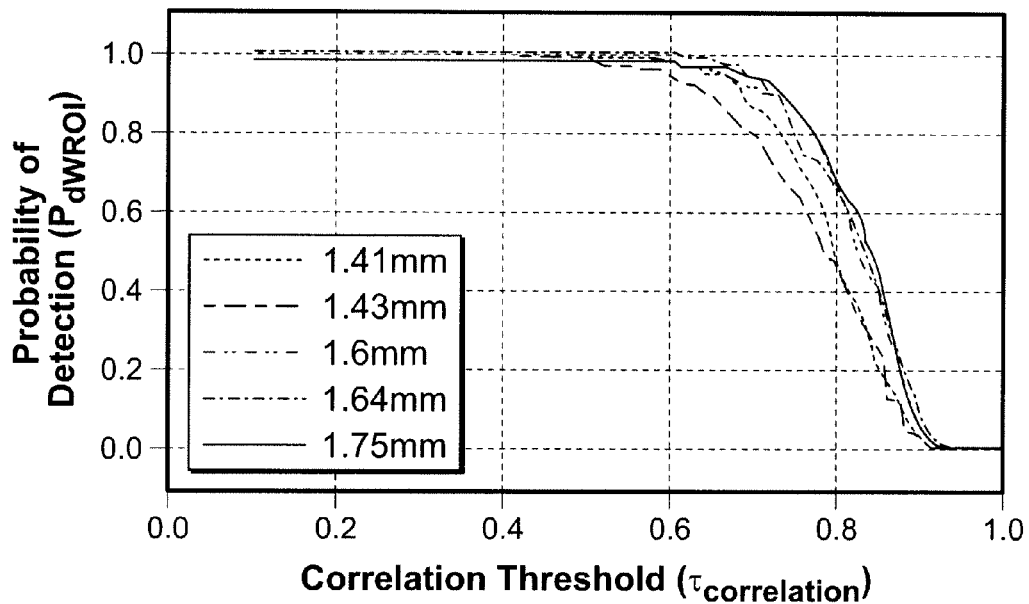
Figure 14D:
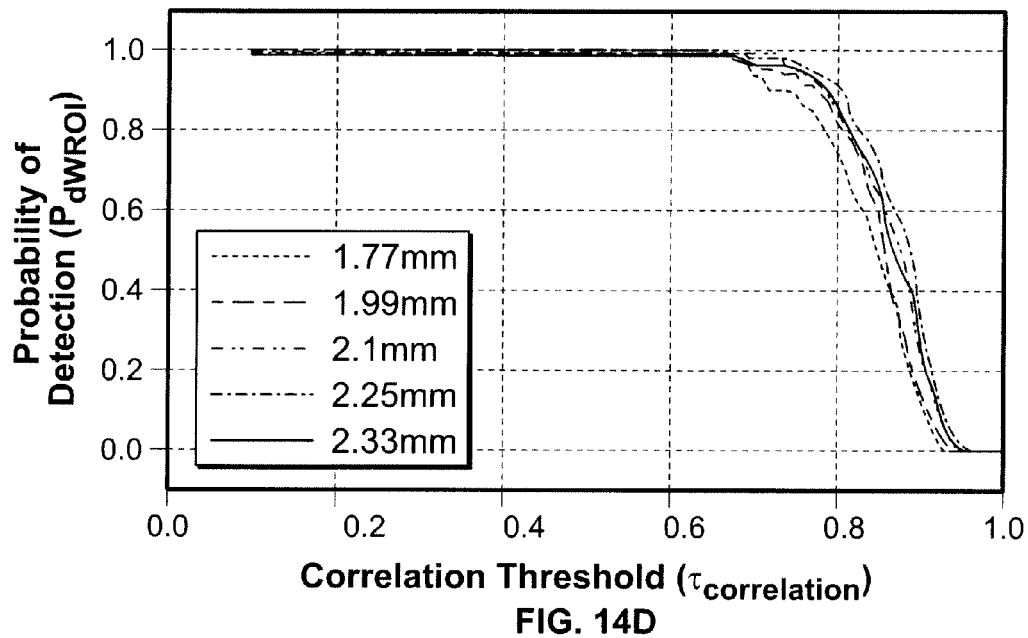

FIG. 11 shows a portion of a spectrum, as a solid line, in which a doublet of the chemical and its other major peaks are identified by the windows 1104. FIG. 11 further shows the difference of the spectrum 1106, and dashed lines as the threshold limits on the difference 1102. It can be seen in FIG. 11 that the differences at the sample points corresponding to the major chemical signature features (e.g., at approximately 760 on the primal-domain sample points) are higher in magnitude than at other sample points. It should be noted that not all chemical signature features are identified via this technique. Nonetheless, the objective of the technique—to identify the widest chemical feature (multiplet)—is achieved.

A difference threshold set to one-third of the standard deviation across all sample points of the spectrum seems to yield results comparable to that obtained via visual inspection. The threshold is set three times higher when library spectra are analyzed using this technique. This need for a change in parameters is not a cause of concern because library spectra are available offline enabling fine tuning of process parameters to achieve optimal results. The slope threshold in the SWTPE is also set empirically to the standard deviation of the spectral data across all sample points.

According to some aspects of the present concepts, prior knowledge of a chemical's spectrum stored in a library may be utilized to determine the sliding-window length. In combination with the library spectrum, common interferences such as, for example, Nitrogen or Oxygen, that cause peaks to potentially fall close to the chemical's signature may be considered. The widest multiplet is selected from a mixture spectra of the library spectrum and potential interference spectrum.

However, to be generic, we can say that the sliding window span selection is based on the widest multiplet that needs to be detected, which in practice, as I mentioned above, depends on the chemical's library and the interferences that may be expected to be present in the area of irradiation.

The processing steps of the SWTPE algorithm proceeds by, first, reading the measured spectral data and the wavenumber vector in the range of 400 cm$^{-1}$ to 3200 cm$^{-1}$. Second, the data at the wavenumbers corresponding to the library chemical is interpolated to match their spectral non-linearities. Third, the IRC data is read and interpolated at the wavenumbers corresponding to the measured data. The interpolated IRC is smoothed, for example, via a MA filter (l=31) and modify as described above. Fourth, the measured data is smoothed via a LP filter. Fifth, the smoothed data is corrected for IRC by dividing it with the modified IRC of step 4. Sixth, all negative values are replaced with zero. Seventh, the IRC corrected data is normalized with respect to energy by dividing it with the sum of its magnitudes. Eighth, a sliding-window length is selected via the dynamic-sliding-window length selection technique described above. Ninth, the pedestal of the IRC corrected data is estimated via the sliding-window technique for pedestal estimation using the sliding-window length of step 8. Tenth, the pedestal is subtracted from the IRC corrected data to obtain a pedestal-free data. Eleventh, the four interfering peaks are truncated. Twelve, the spectrum of step 11 is correlated with similarly processed library spectrum in both FWR and WROI. One of ordinary skill in the art will appreciate that some of these steps may be performed in a different order than described above.

The variability of the pedestal in Raman-shift data is addressed by estimating it as an approximation to the lower envelope of the data. The LIPE estimates the pedestal by linear interpolation on the entire set of local minima of the data. The LIPE works perfectly well for purposes of detection; however from a spectroscopist's perspective, the disadvantage of LIPE is that it splits multiplets into individual peaks. The SWTPE addresses the multiplet splitting problem of LIPE. The SWTPE processes data via sliding-windows and aims at retaining multiplets.

The performance of detection algorithms is generally assessed by plotting the receiver operating characteristics (ROC): a plot of the probability of detection, $P_d$, versus the probability of false alarm, $P_{fa}$, where each probability is computed for different correlation thresholds, $\tau_{correlation}$. The $\tau_{correlation}$ is the detection threshold that marks the boundary in the decision space between a positive and a negative match. Therefore, if the correlation coefficient between the processed spectrum and a chemical library spectrum is greater than or equal to $\tau_{correlation}$, then the processed spectrum is considered to match the library spectrum of the chemical. Otherwise, the processed spectrum does not represent the chemical corresponding to the library spectrum.

All datasets described herein, except Dataset 6, contain spectra that correspond to a single chemical. Dataset 6 comprises 750 Chemical_B-on-concrete spectra randomly inserted among 6750 concrete spectra and 750 Chemical_B-on-asphalt spectra randomly inserted among 6750 asphalt spectra. Also included in Dataset 6 is a library file of four chemicals, Chemical_A, Chemical_B, Chemical_C, and Chemical_E. Dataset 6, on the other hand, has chemical spectra randomly inserted between background spectra. This allows the computation of $P_d$ and $P_{fa}$. It is not possible to compute $P_{fa}$ in other datasets because all spectra are known to be chemical spectra; therefore, the detection performance for those datasets is assessed by plotting $P_d$ versus $\tau_{correlation}$.

The $P_d$ is computed as the ratio of the number of spectra that result in a positive match with the library spectrum to the total number of spectra processed. The $P_d$ in Dataset 6, on the other hand, is computed as the ratio of the number of chemical spectra that yield a positive match to the total number of chemical spectra. The $P_{fa}$ is computed as the ratio of the number of background spectra that result in a positive match to the total number of background spectra. In all the plots shown in FIGS. 12-31, the $\tau_{correlation}$ is varied from 0 to 1 in steps of 0.01 to get a sufficiently smooth curve.

As described above, two correlation coefficients are computed: (a) using the full wavenumber range (FWR) and (b) using the library spectra's wavenumber range of interest (WROI). Consequently, two probabilities of detection are computed—$P_{dFWR}$ and $P_{dWROI}$, respectively. The following are the FWR and WROI ranges used for the detection of the seven chemicals:

1. TMeS
   (a) FWR: 38 cm$^{-1}$ to 4849.7 cm$^{-1}$
   (b) WROI: 308 cm$^{-1}$ to 2227.5 cm$^{-1}$
2. MES
   (a) FWR: −131.6 cm$^{-1}$ to 3556.8 cm$^{-1}$
   (b) WROI: 746.8 cm$^{-1}$ to 1788.8 cm$^{-1}$
3. TEPO
   (a) FWR: −131.6 cm$^{-1}$ to 3556.8 cm$^{-1}$
   (b) WROI: 220 cm$^{-1}$ to 1661.4 cm$^{-1}$ and 2640 cm$^{-1}$ to 3095.5 cm$^{-1}$
4. Chemical_A
   (a) FWR: 401.1 cm$^{-1}$ to 3199.7 cm$^{-1}$
   (b) WROI: same as full wavenumber range
5. Chemical_B
   (a) FWR: 401.1 cm$^{-1}$ to 3199.7 cm$^{-1}$
   (b) WROI: 563.18 cm$^{-1}$ to 1621.1 cm$^{-1}$ and 2752.6 cm$^{-1}$ to 3187.1 cm$^{-1}$
6. Chemical_C
   (a) FWR: 401.1 cm$^{-1}$ to 3199.7 cm$^{-1}$
   (b) WROI: 441.9 cm$^{-1}$ to 1770.7 cm$^{-1}$
7. Chemical_E
   (a) FWR: 401.1 cm$^{-1}$ to 3199.7 cm$^{-1}$
   (b) WROI: 441.9 cm$^{-1}$ to 1528.8 cm$^{-1}$ and 2686.5 cm$^{-1}$ to 3187.1 cm$^{-1}$ The results are discussed according to the datasets involved. Each dataset is used to discuss one of several aspects of the algorithm, such as averaging, peak truncations, etc., that impact detection performance. For instance, LIPE results corresponding to Dataset 2 are used to demonstrate the advantages of averaging (assuming N spectra are from the same source). Next, SWTPE results for Dataset 2 are presented to demonstrate that SWTPE and LIPE results match closely. Results pertaining to Dataset 3 are used to demonstrate the advantages of WROI correlation over FWR correlation. Dataset 3 comprises Raman-shift data from an EDM0 instrument (comprising an ICCD made up of 1024×256 optical detectors) pertaining to four different concentrations (0.5, 1.0, 5.0, and 10.0 μL) each of two chemicals (MES and TEPO) on concrete, respectively. Dataset 3 also comprises library spectra of MES, TEPO, and other chemicals/backgrounds. Dataset 4 comprises 1024-point spectral measurements of five chemicals by an EDM0 instrument, designated as Chemical_A, Chemical_B, Chemical_C, Chemical_D, and Chemical_E. These measurements are rid of any backgrounds such as concrete or asphalt, but are interfered by an air signature. Dataset 5 comprises spectral measurements of six chemicals, Chemical_A, Chemical_B, Chemical_C, Chemical_D, Chemical_E, and Chemical_F, each placed on a concrete background, and another file containing a library quality spectra of 66 chemicals unmapped to chemical names. Results of Dataset 4 are used to present the effects of truncating interfering peaks, while results of Dataset 5 show the effect of background on detection performance. Finally, Dataset 6 is used to demonstrate SWTPE's performance in terms of $P_d$ and $P_{fa}$.

A correlation threshold, $\tau_{correlation}=0.7$, is used in the ensuing discussion of the performance of the algorithms because it was seen that $P_{dWROI}$ was sufficiently high ($\approx 0.8$) for this threshold value for most chemicals. Further, the correlation coefficients of background spectra and chemical library spectra are <<0.7, thereby, yielding a low $P_{fa}$ for $\tau_{correlation}=0.7$.

The preliminary detection algorithm involving the use of LIPE was used to analyze the TMeS drop data (Dataset 2). Since LIPE is based on averaging N spectra, three different values of N (1, 15, and 25) were chosen to study the effect of averaging on the detection performance via WROI correlation. FIGS. 12-14 show an overlay of $P_{dWROI}$ versus $\tau_{correlation}$ curves for N=25, 15, and 1, respectively. The 20 different curves in each figure correspond to 20 drop-diameters of TMeS on glass.

It can be seen from these figures that for drop diameters greater than 0.56 mm using N=25 yields a $P_d=1$ at a reasonably high $\tau_{correlation}=0.7$. However, $P_d$ drops significantly for $\tau_{correlation}>0.5$ for the smallest drop-diameter (0.49 mm). Decreasing the value of N to 15 yields $P_d=0$ (at $\tau_{correlation}=0.7$) for the smallest drop-diameter, while it is only marginally changed for the larger drop diameters.

The detection performance of the LIPE for N=1 significantly changes the $P_d$ curves for the smaller drop diameters. Even for drop diameters as high as 1.07 mm, $P_d \leq 0.5$ at $\tau_{correlation}=0.7$. For drop diameters less than 1 mm, $P_d \leq 0.2$.

Figure 15A:
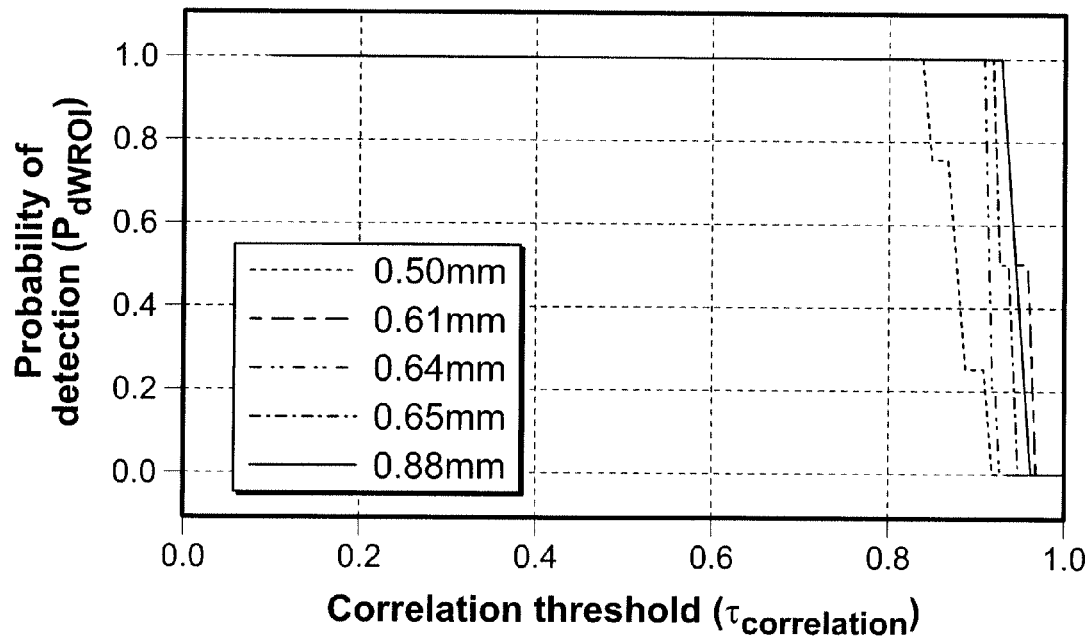
FIGS. 15A-C are plots of LIPE performance on TMeS-on-gravel data for N=25 in accord with at least some aspects of the present concepts.
Figure 15B:
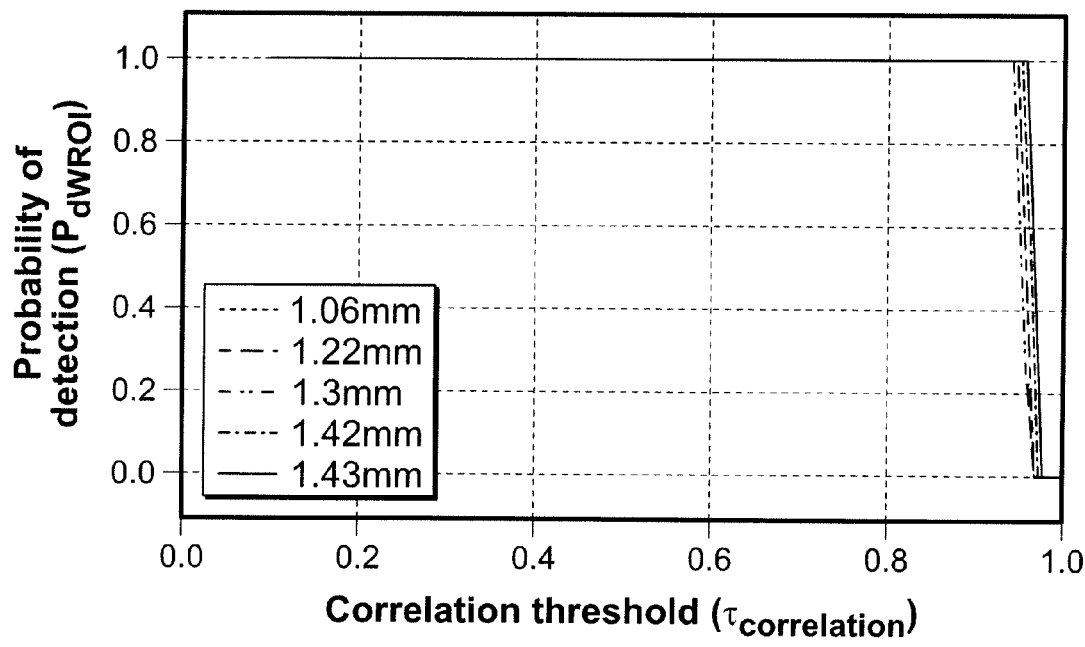
Figure 15C:
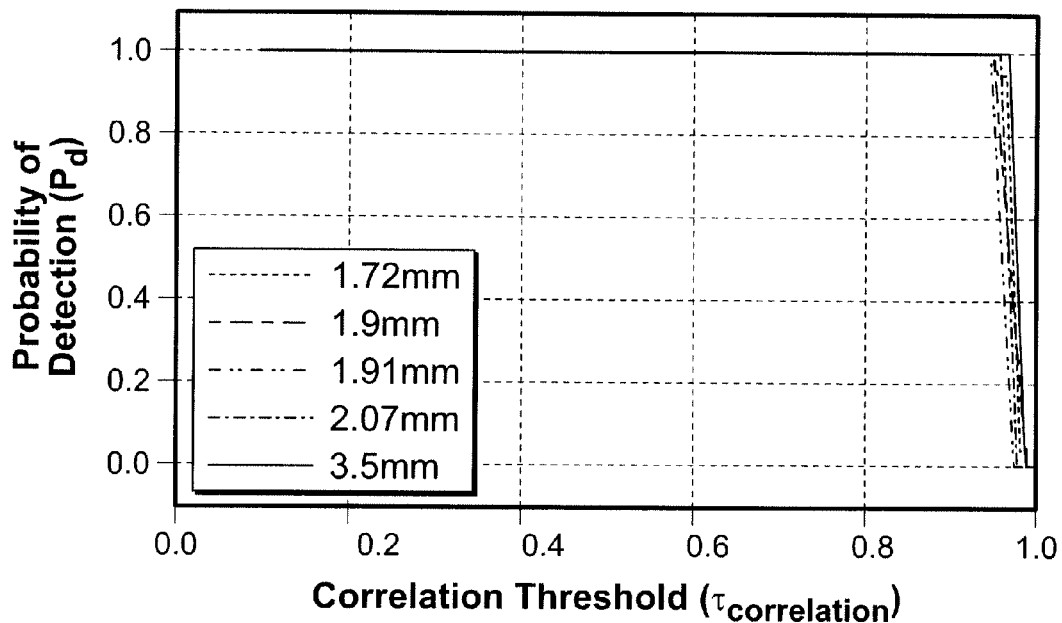
Figure 16A:
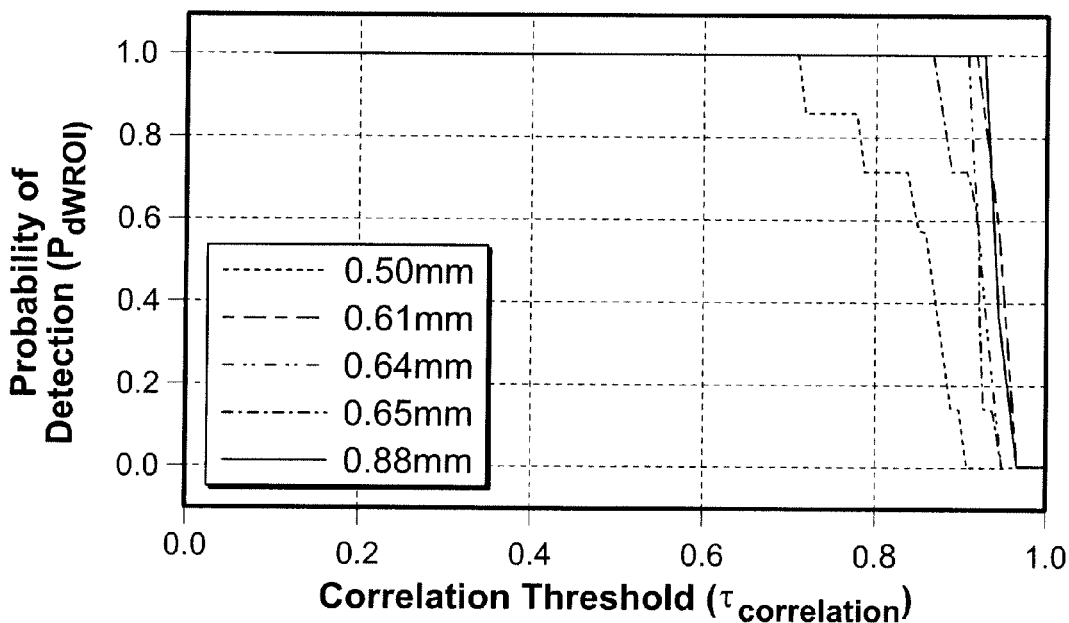
FIGS. 16A-C are plots of LIPE performance on TMeS-on-gravel data for N=15 in accord with at least some aspects of the present concepts.
Figure 16B:
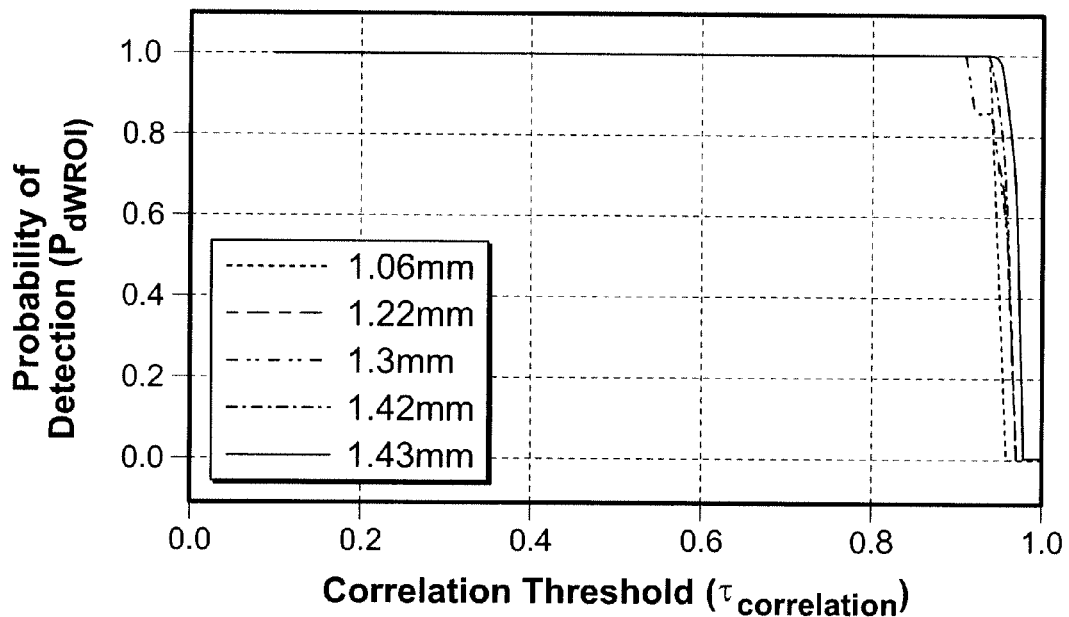
Figure 16C:
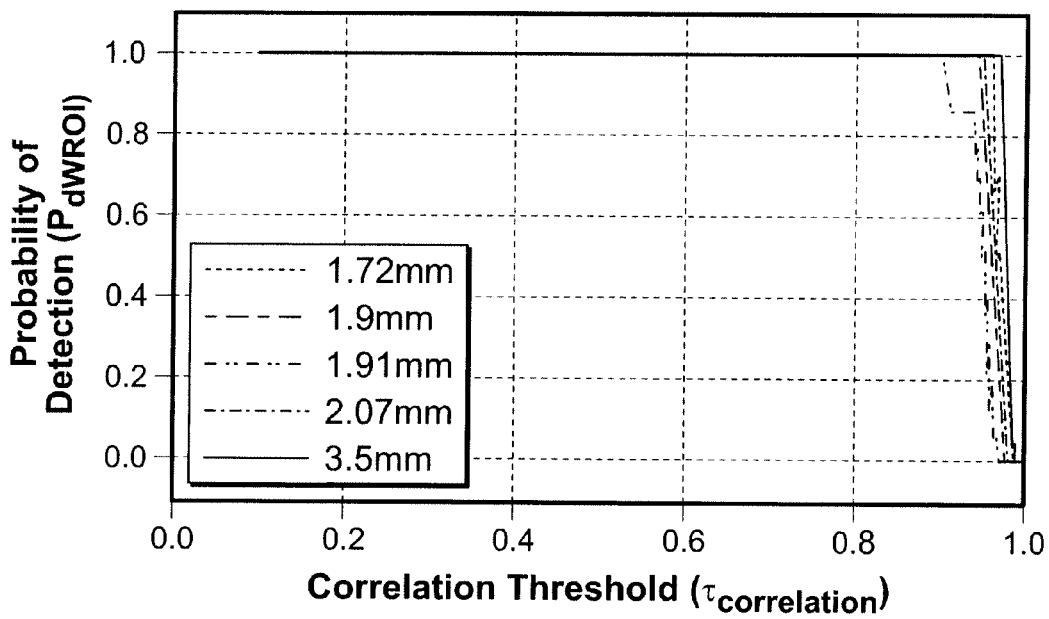
Figure 17A:
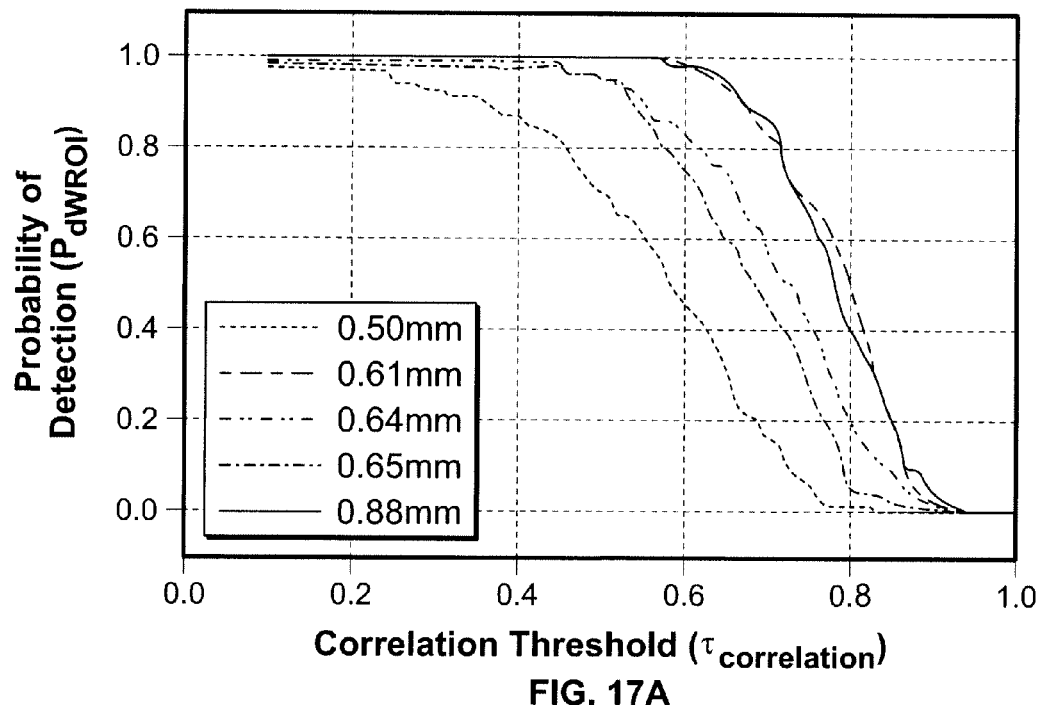
FIGS. 17A-C are plots of LIPE performance on TMeS-on-gravel data for N=1 in accord with at least some aspects of the present concepts.
Figure 17B:
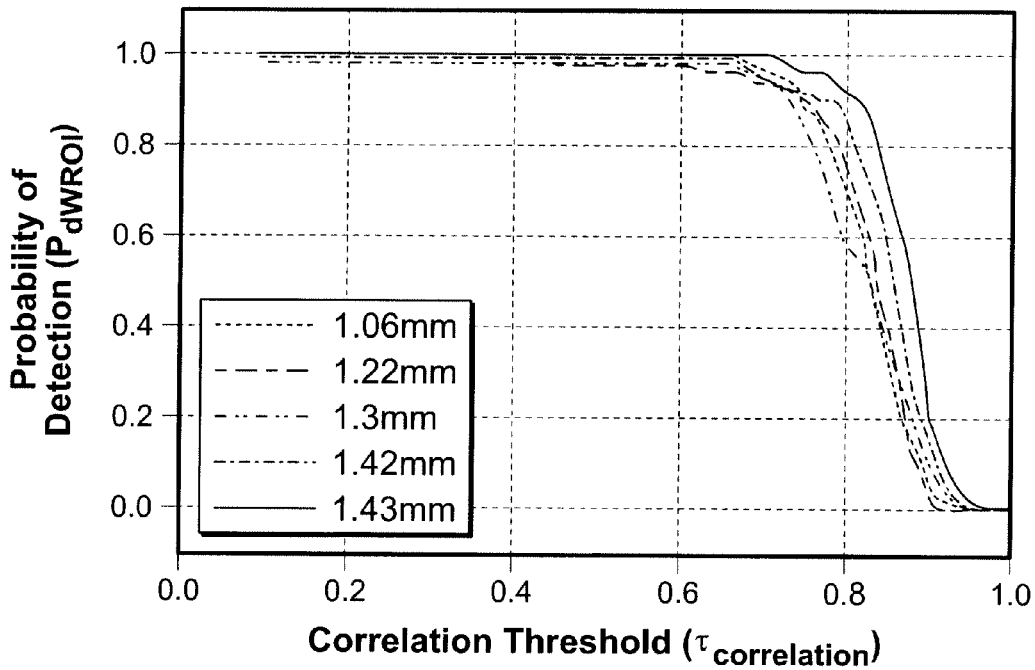
Figure 17C:
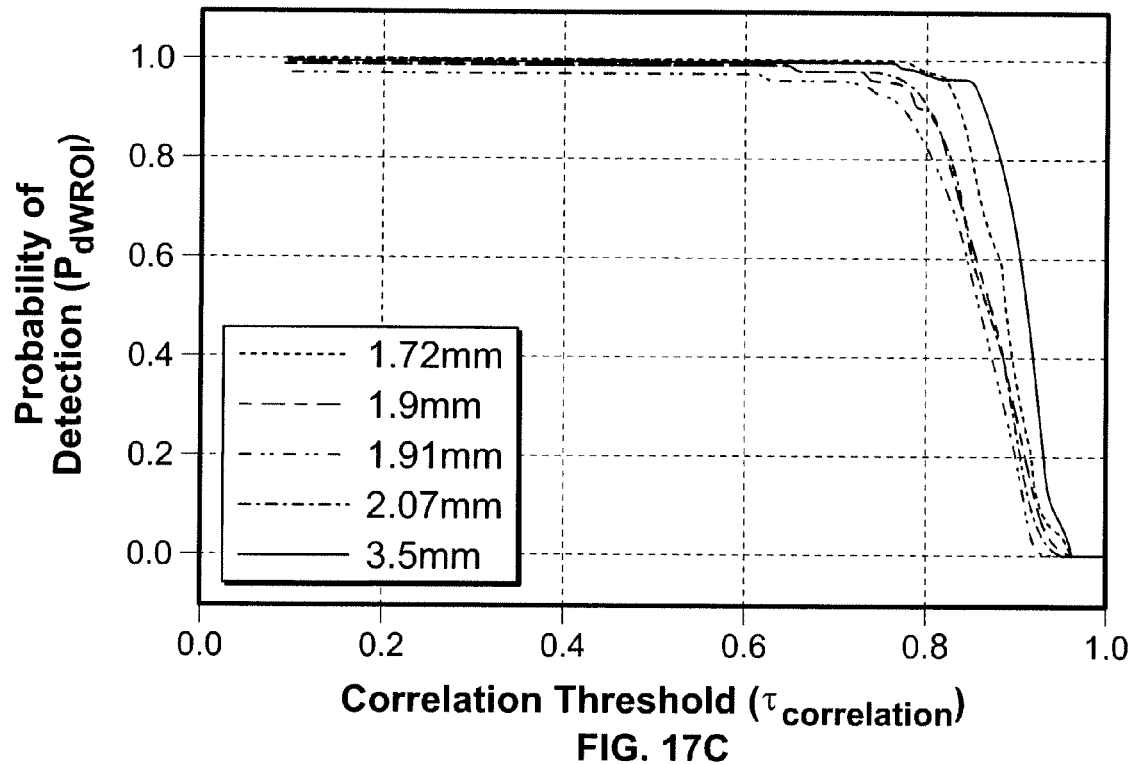
Figure 18A:
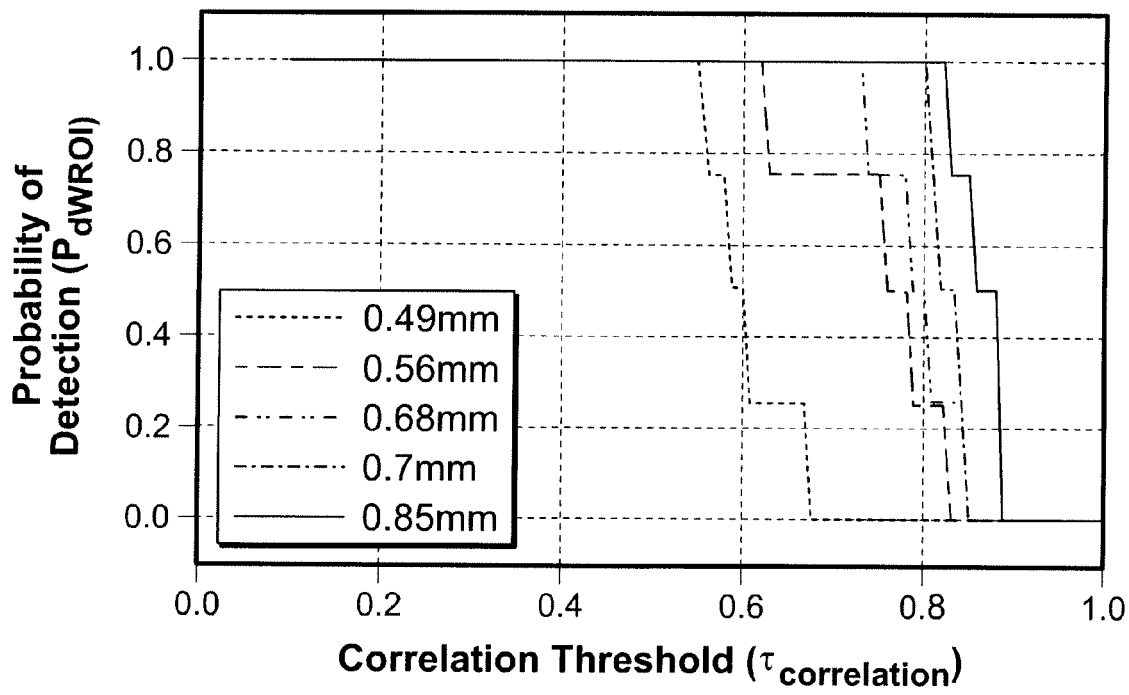
FIGS. 18A-D are plots of SWTPE performance on TMeS-on-glass data for N=25 in accord with at least some aspects of the present concepts.
Figure 18B:
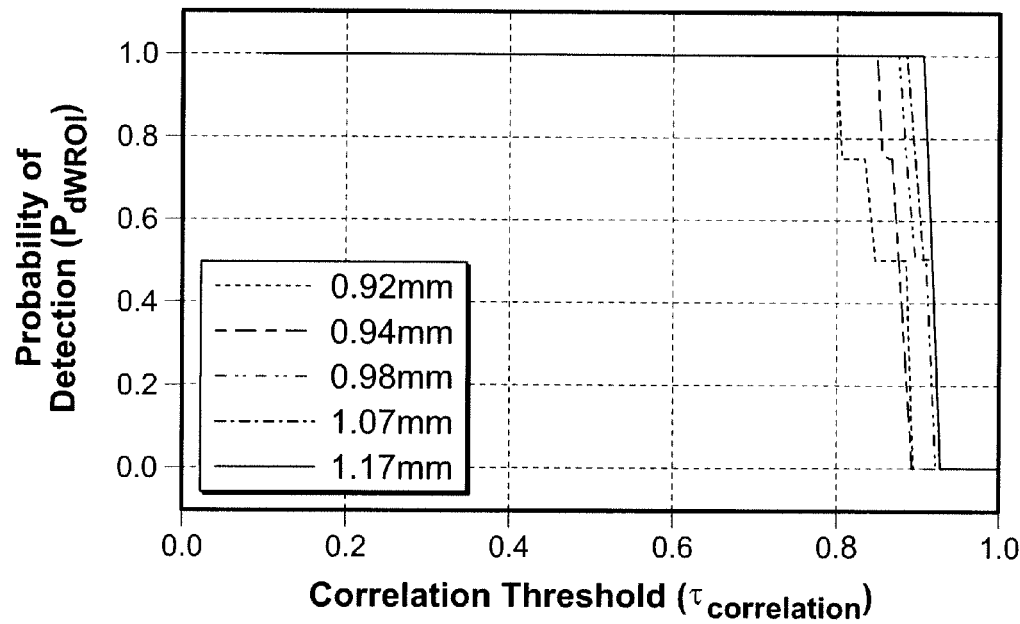
Figure 18C:
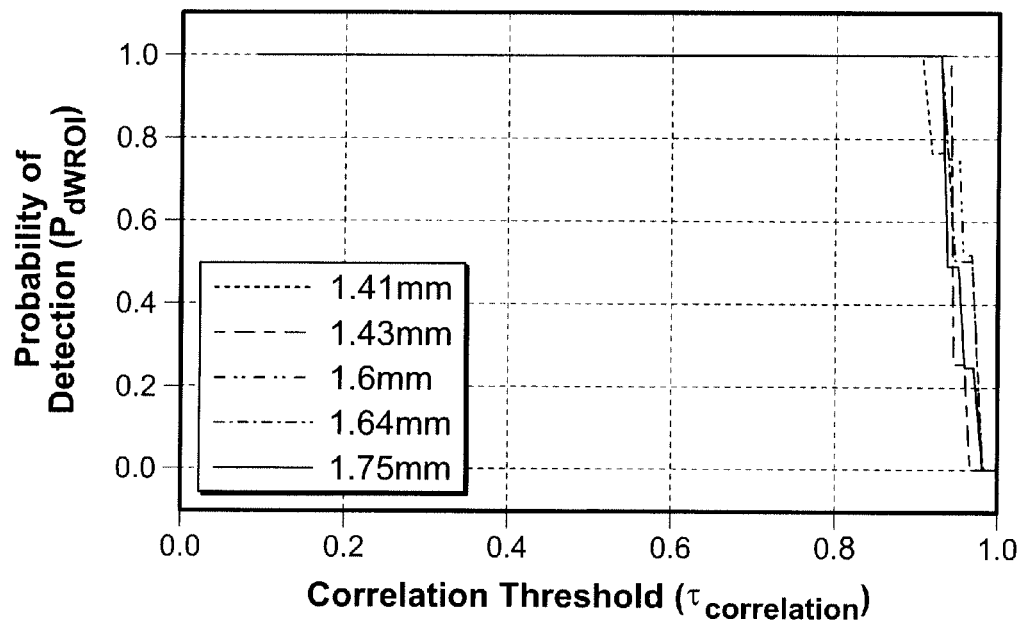
Figure 18D:
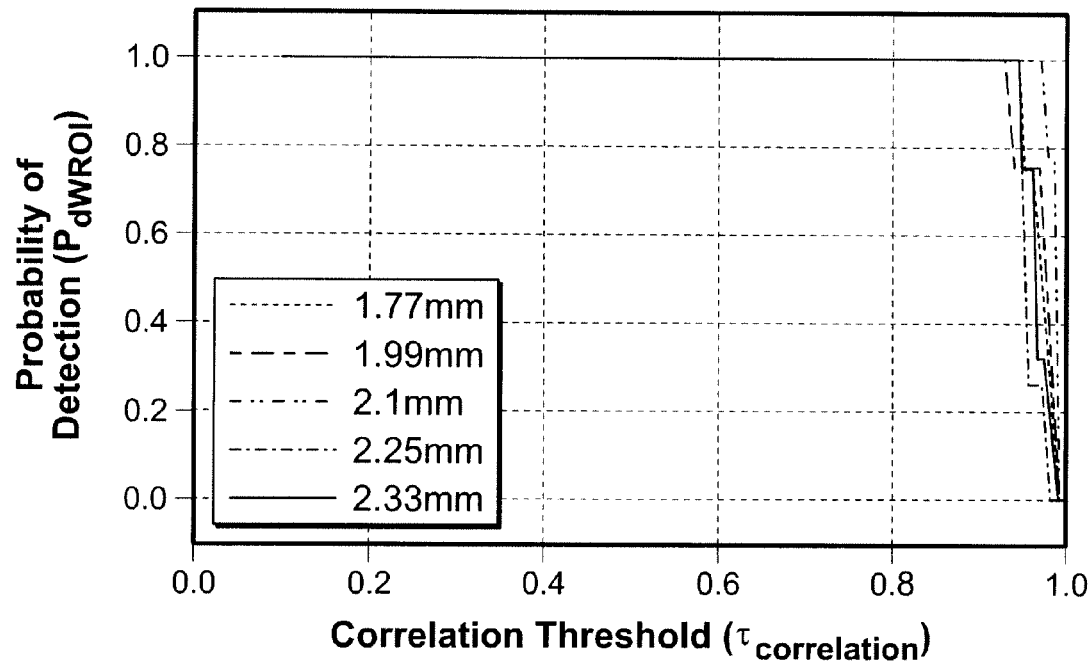
Figure 19A:
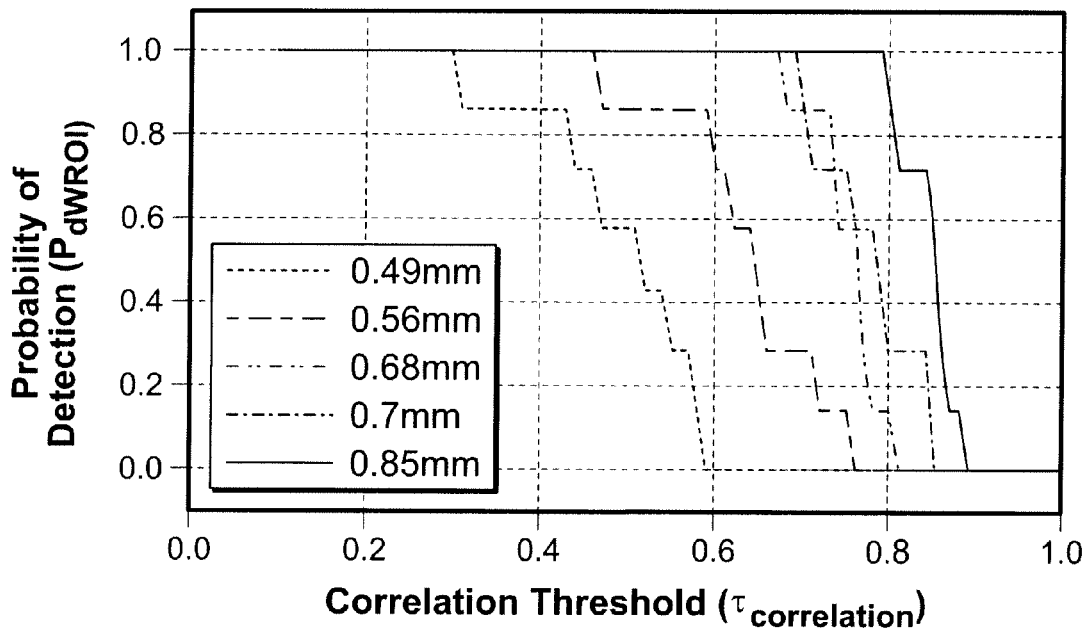
FIGS. 19A-D are plots of SWTPE performance on TMeS-on-glass data for N=15 in accord with at least some aspects of the present concepts.
Figure 19B:
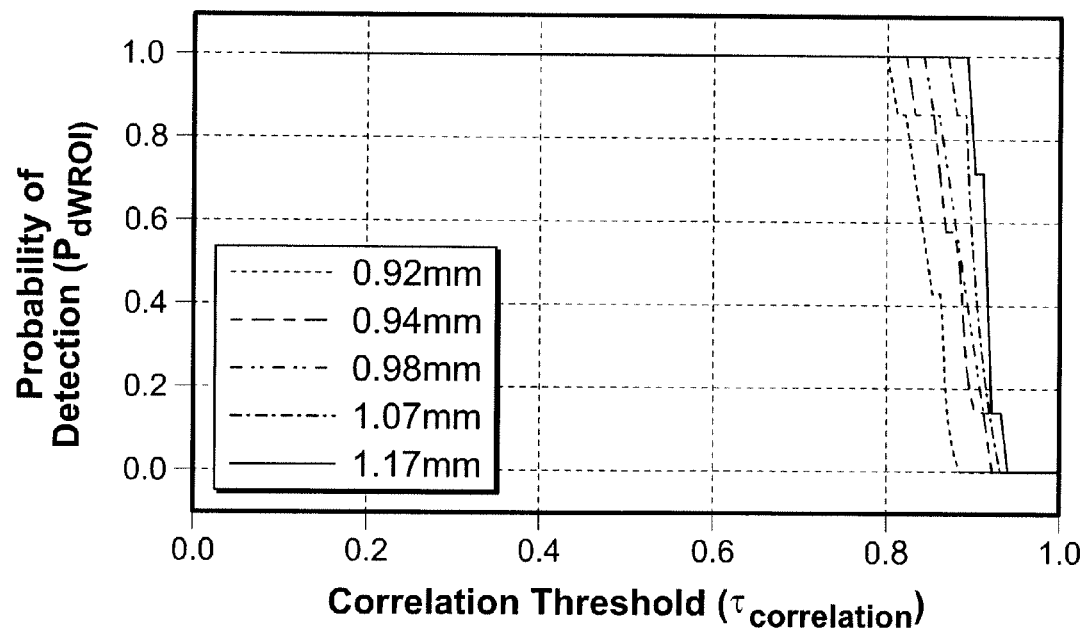
Figure 19C:
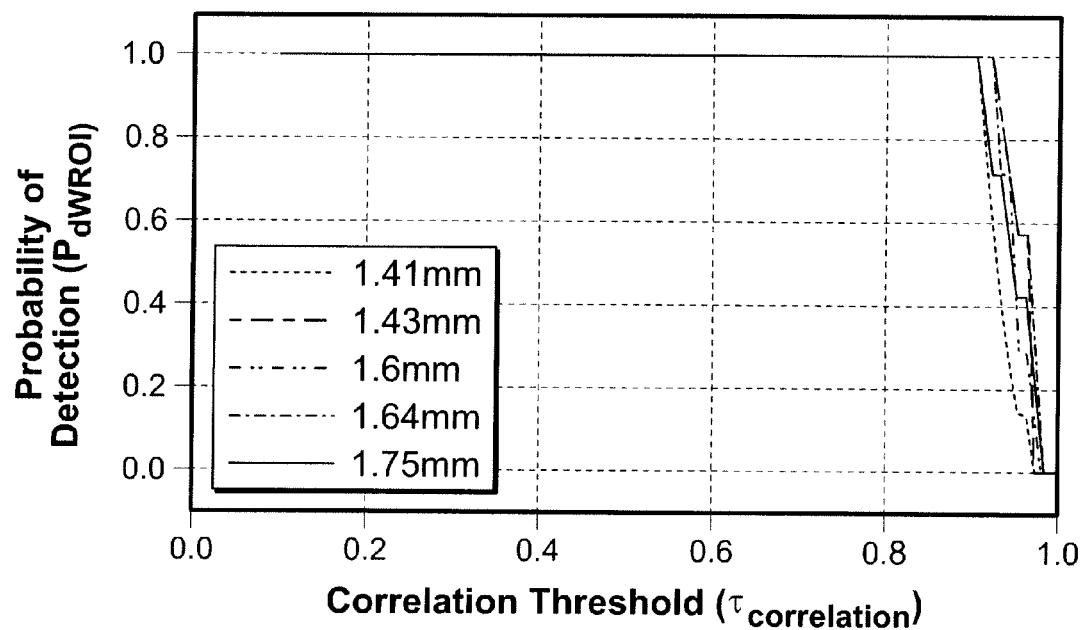
Figure 19D:
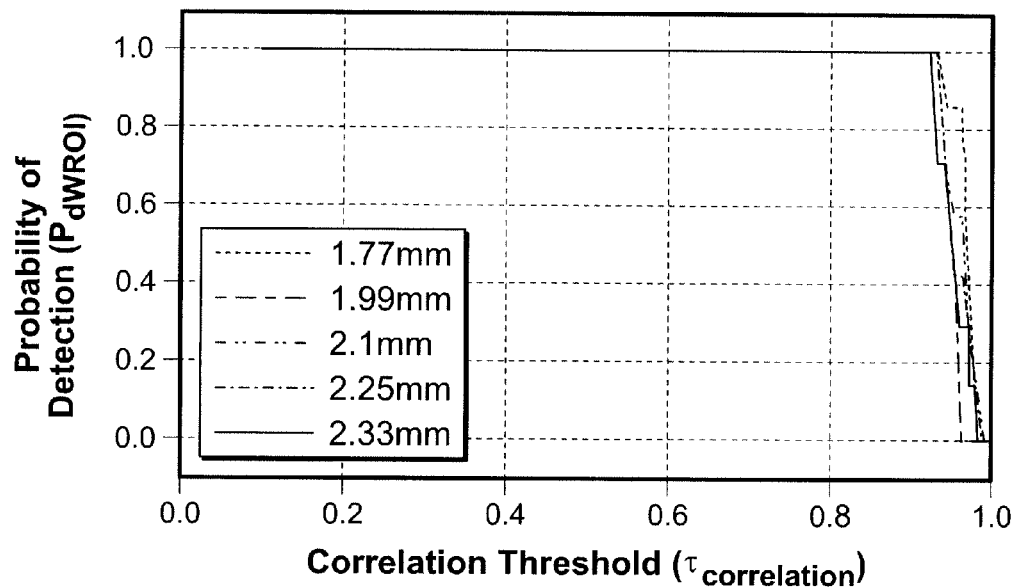
Figure 20A:
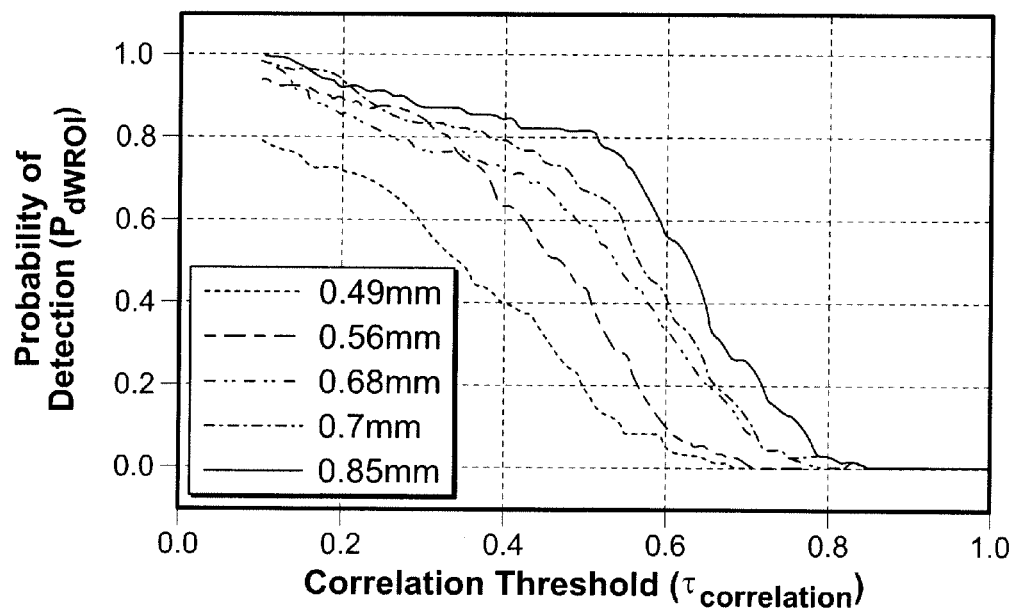
FIGS. 20A-D are plots of SWTPE performance on TMeS-on-glass data for N=1 in accord with at least some aspects of the present concepts.
Figure 20B:
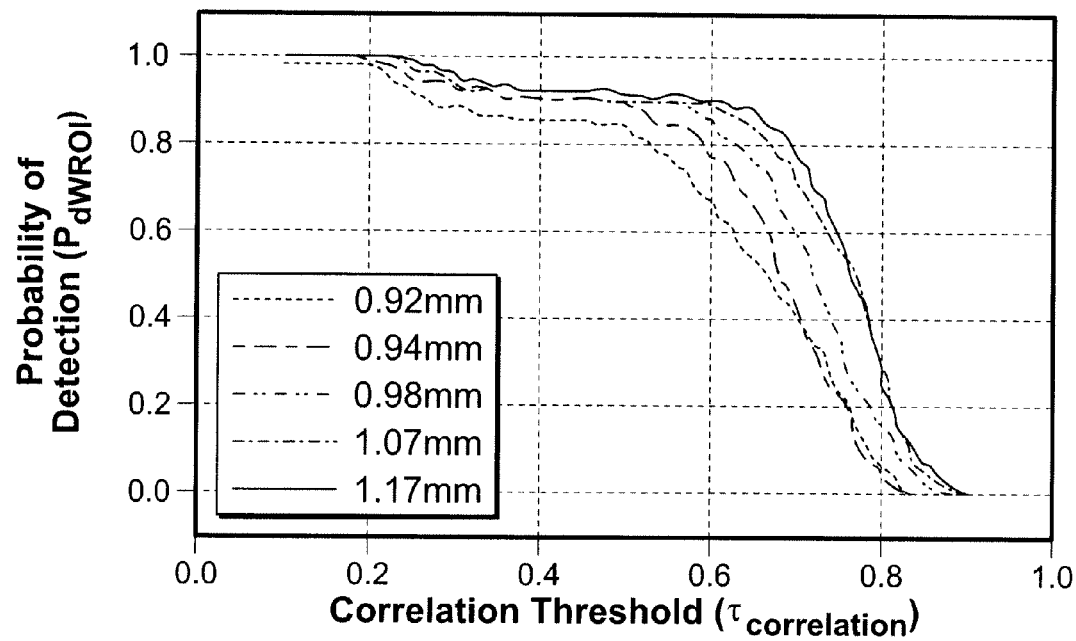
Figure 20C:
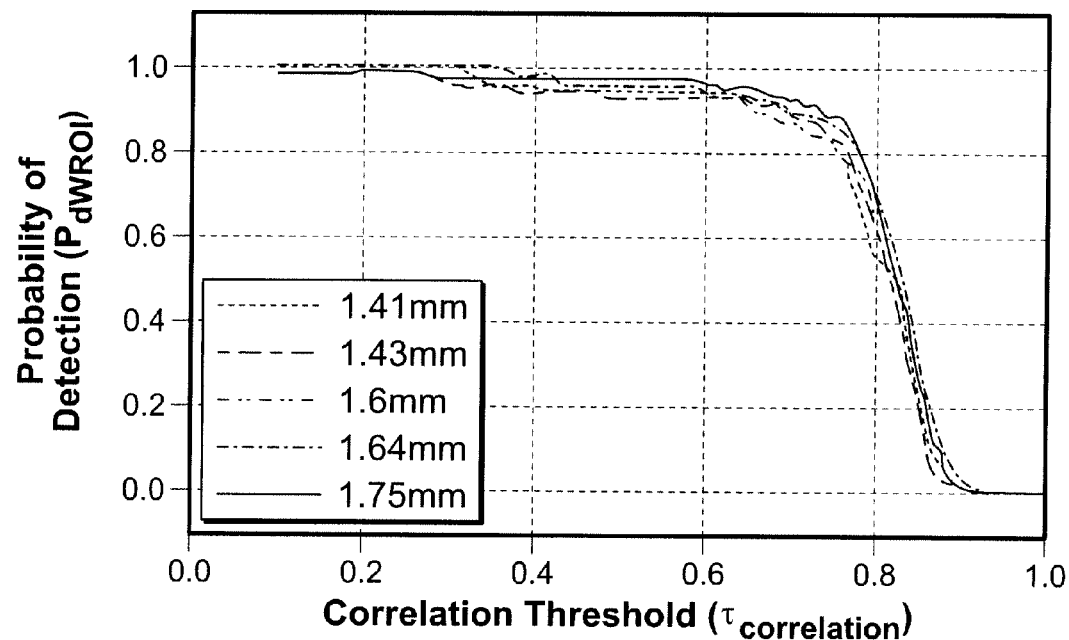
Figure 20D:
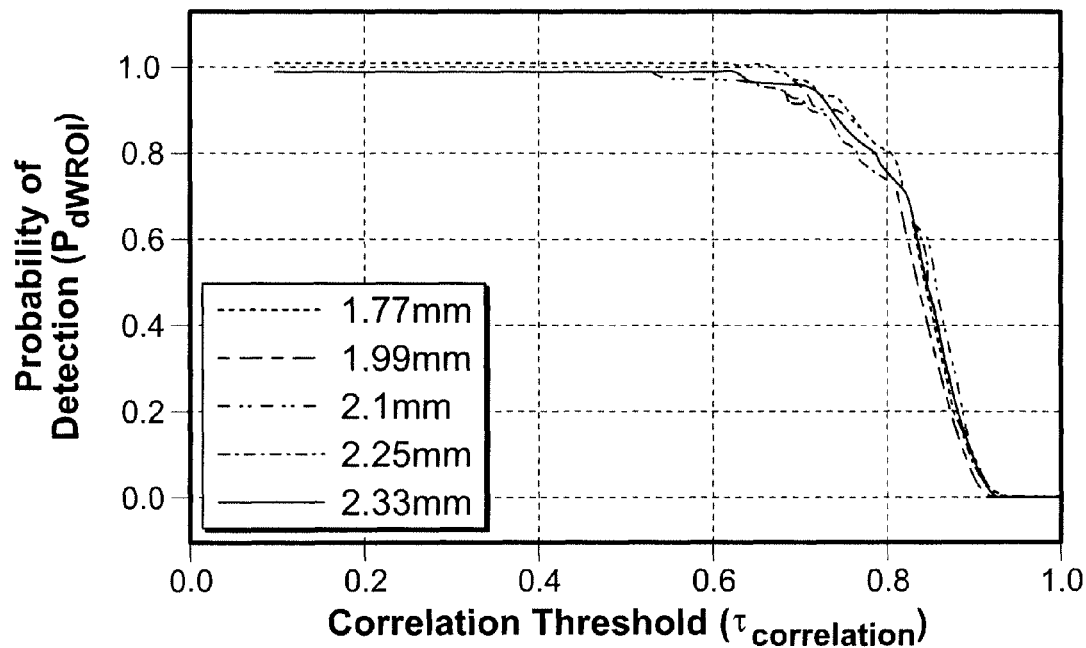

FIGS. 15-17 show $P_d$ versus $\tau_{correlation}$ curves for N=25, 15, and 1, respectively, corresponding to TMeS-on-gravel data. The $P_d=1$ for all drop diameters at $\tau_{correlation}=0.7$ in the case of N=25 and 15. For N=1 the $P_d$ at $\tau_{correlation}=0.7$ drops marginally for drop diameters greater than 0.64 mm, while $P_d$ drops to as low as 0.2 for smaller drop diameters.

Surprisingly, TMeS is more detectable when on gravel than on glass due to the stronger Raman signature of TMeS on gravel and the lower additive noise in TMeS-on-gravel data. Further, these results show that although the TMeS spectrum is altered significantly due to multiplet splitting, as a consequence of LIPE pedestal estimate subtraction, as long as both the measured data and the library data are processed similarly, they yield high correlation.

The SWTPE algorithm uses two parameters to estimate the pedestal—the slope threshold and the difference threshold. In processing the spectra from all datasets (i.e., seven different chemicals and four different backgrounds), both these parameters were unchanged. This was done so that the performance of the detection algorithm can be evaluated using a single set of parameters on varied chemicals on arbitrary backgrounds measured by two different instruments. These parameters were set as follows: (1) the "slope threshold" is the standard deviation of the spectrum across the sample points, and (2) the "difference threshold" is one third of the standard deviation of the spectrum across the sample points.

FIGS. 18-20 show SWTPE $P_d$ versus $\tau_{correlation}$ curves corresponding to TMeS-on-glass for N=25, 15, and 1, respectively, for Dataset 2. Comparing the SWTPE and LIPE plots corresponding to N=1, FIGS. 20 and 14, respectively, shows that although smaller drop diameters are difficult to detect via both the algorithms, the SWTPE performs better than the LIPE for smaller drop diameters in that the SWTPE $P_d$ at $\tau_{correlation}=0.6$ is not as low as for LIPE.

Figure 21A:
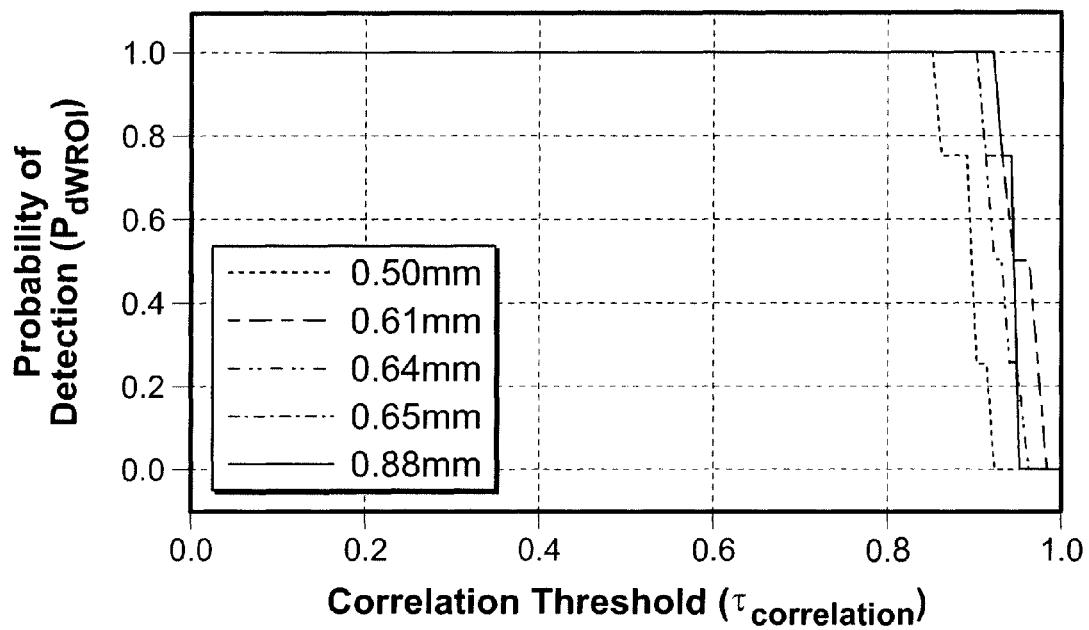
FIGS. 21A-C are plots of SWTPE performance on TMeS-on-gravel data for N=25 in accord with at least some aspects of the present concepts.
Figure 21B:
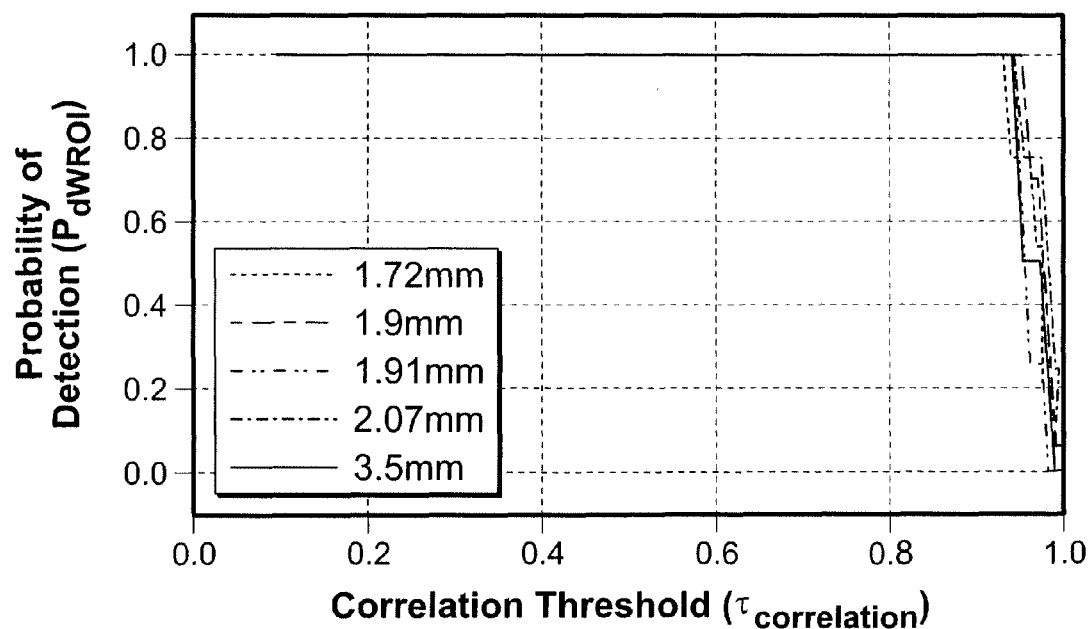
Figure 21C:
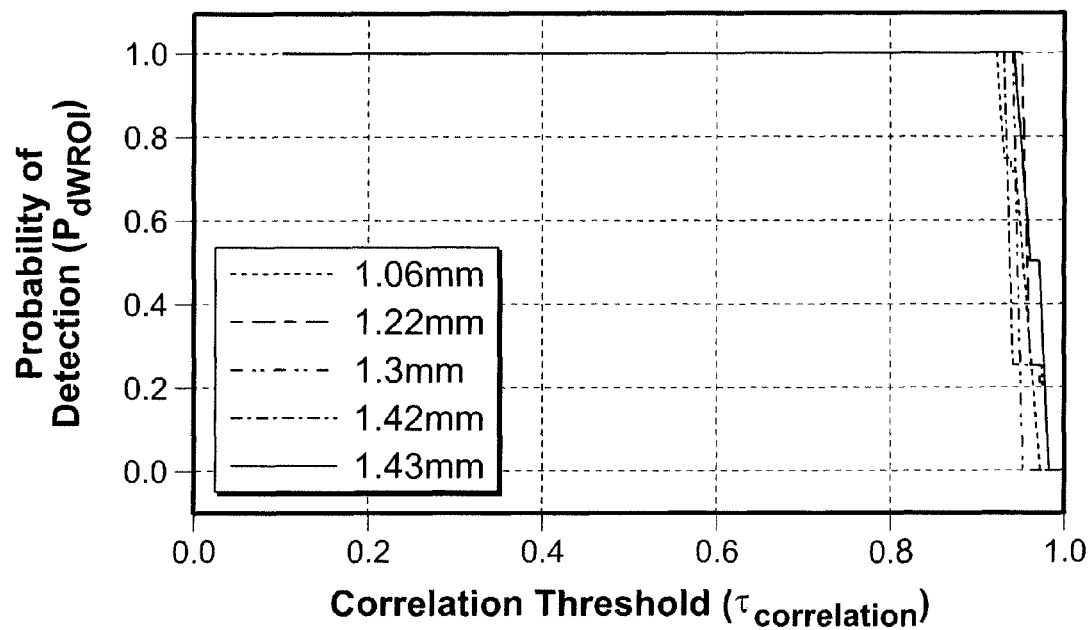
Figure 22A:
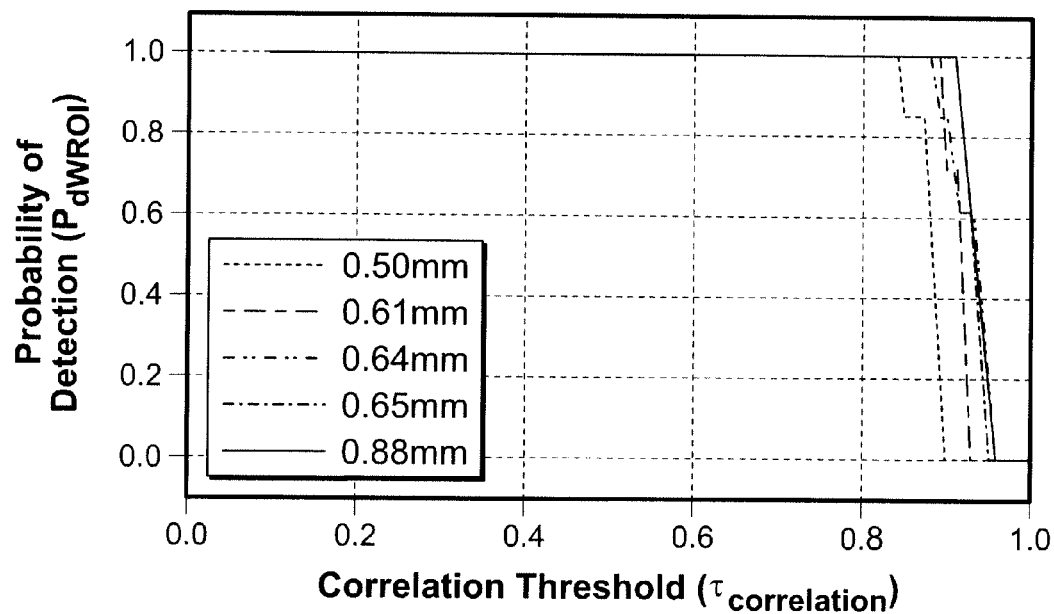
FIGS. 22A-C are plots of SWTPE performance on TMeS-on-gravel data for N=15 in accord with at least some aspects of the present concepts.
Figure 22B:
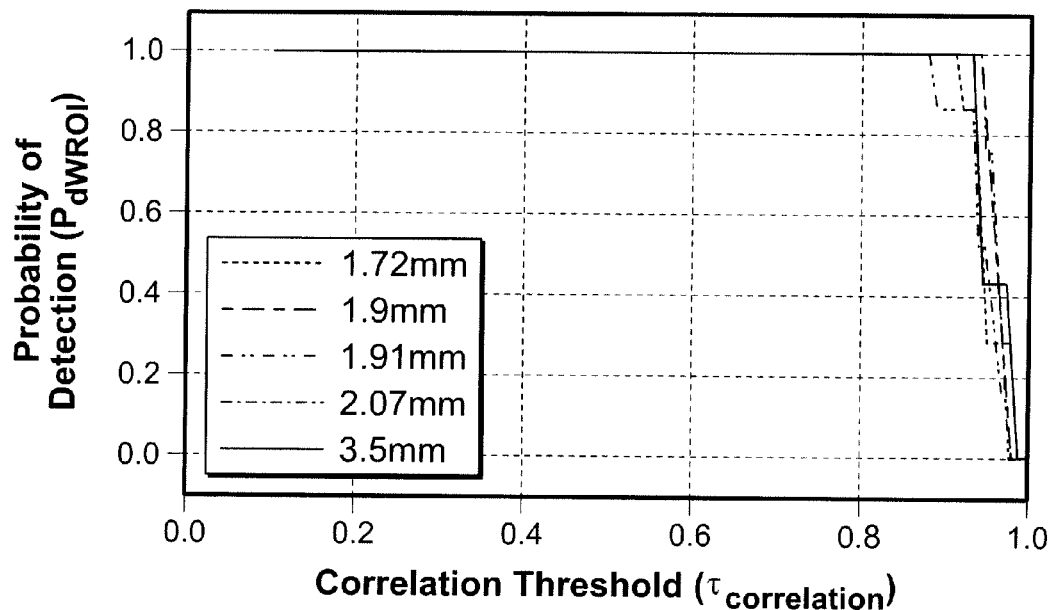
Figure 22C:
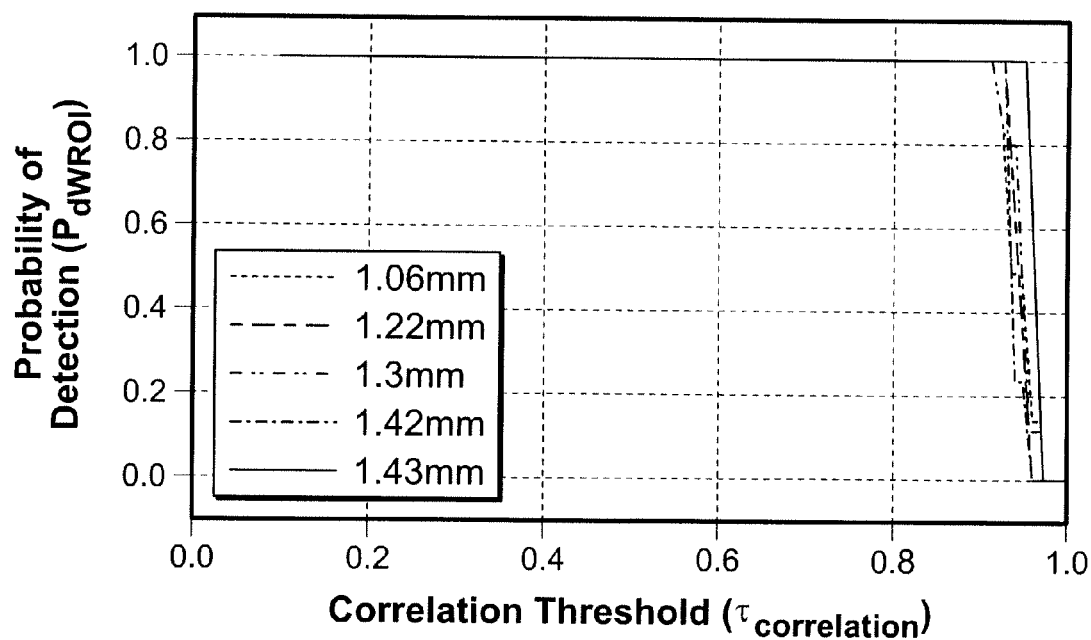
Figure 23A:
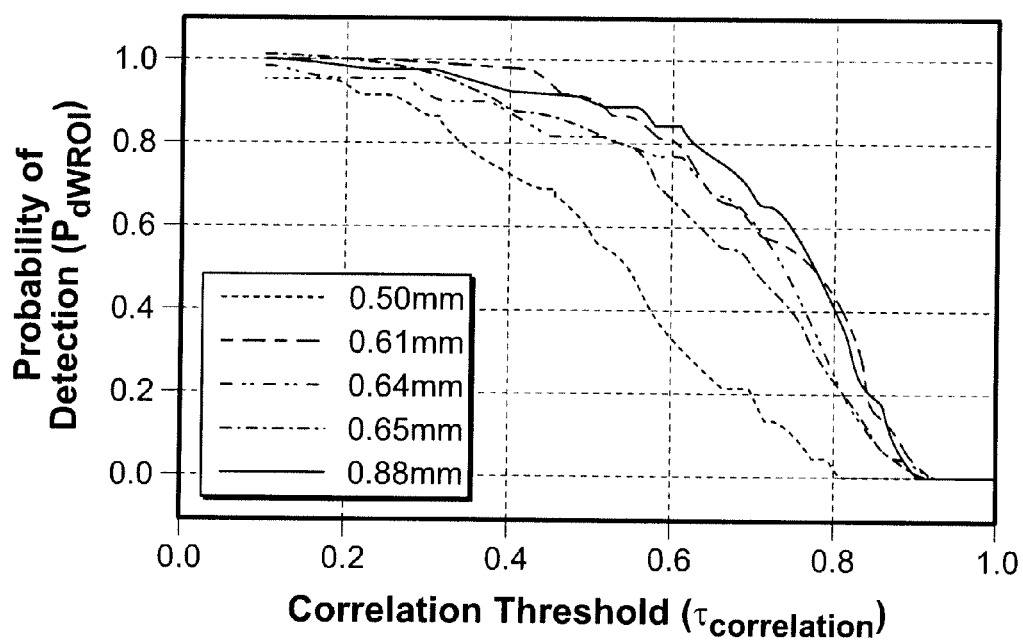
FIGS. 23A-C are plots of SWTPE performance on TMeS-on-gravel data for N=1 in accord with at least some aspects of the present concepts.
Figure 23B:
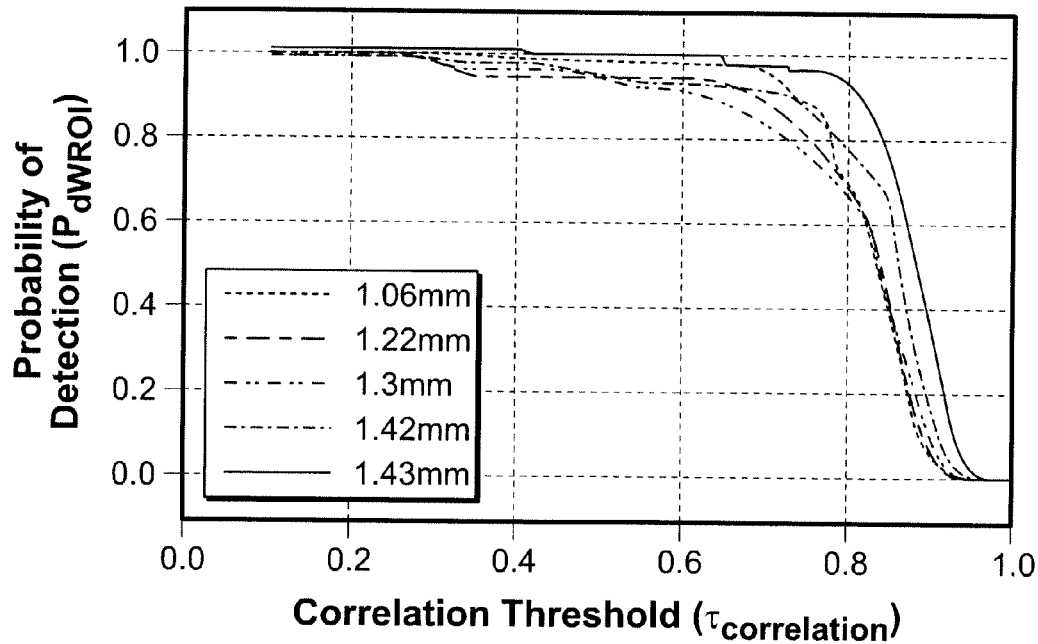
Figure 23C:
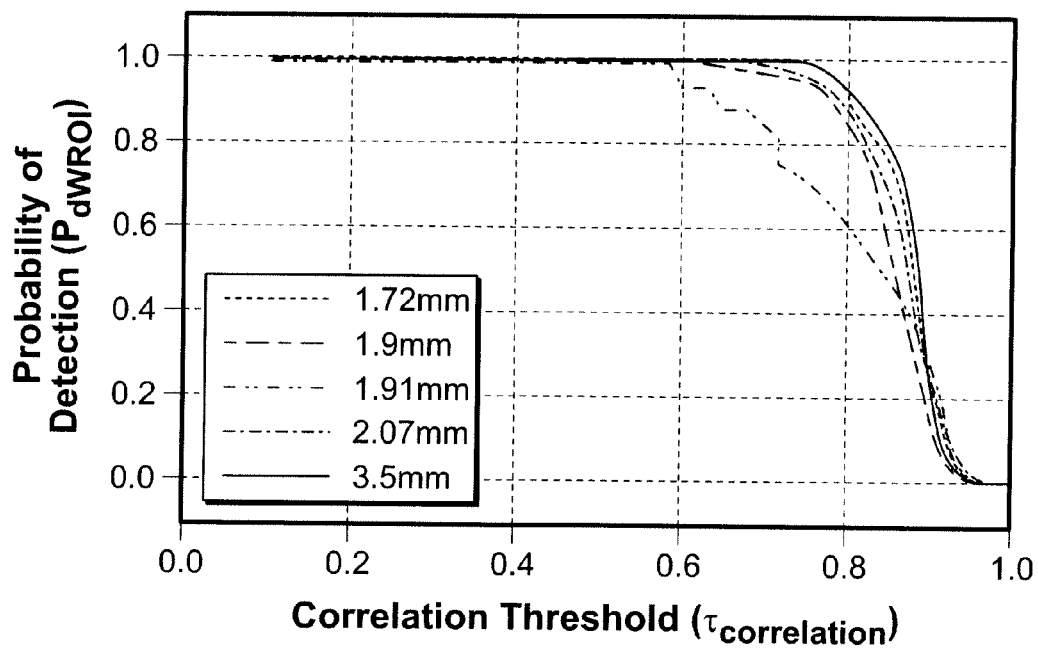
Figure 24A:
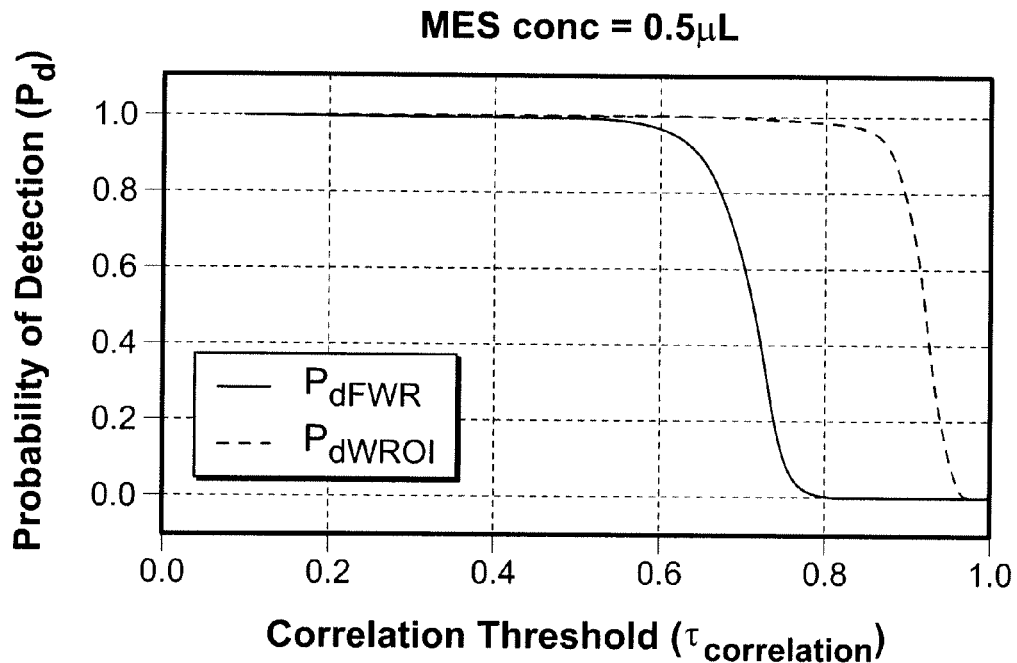
FIGS. 24A-D are plots of SWTPE performance on MES data for N=1 in accord with at least some aspects of the present concepts.
Figure 24B:
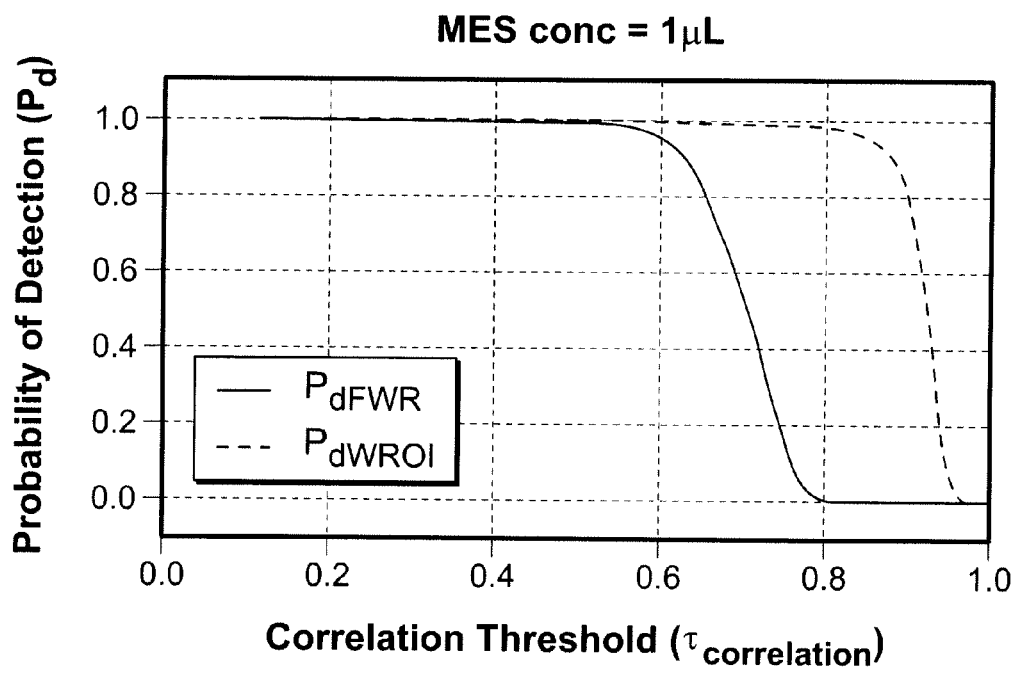
Figure 24C:
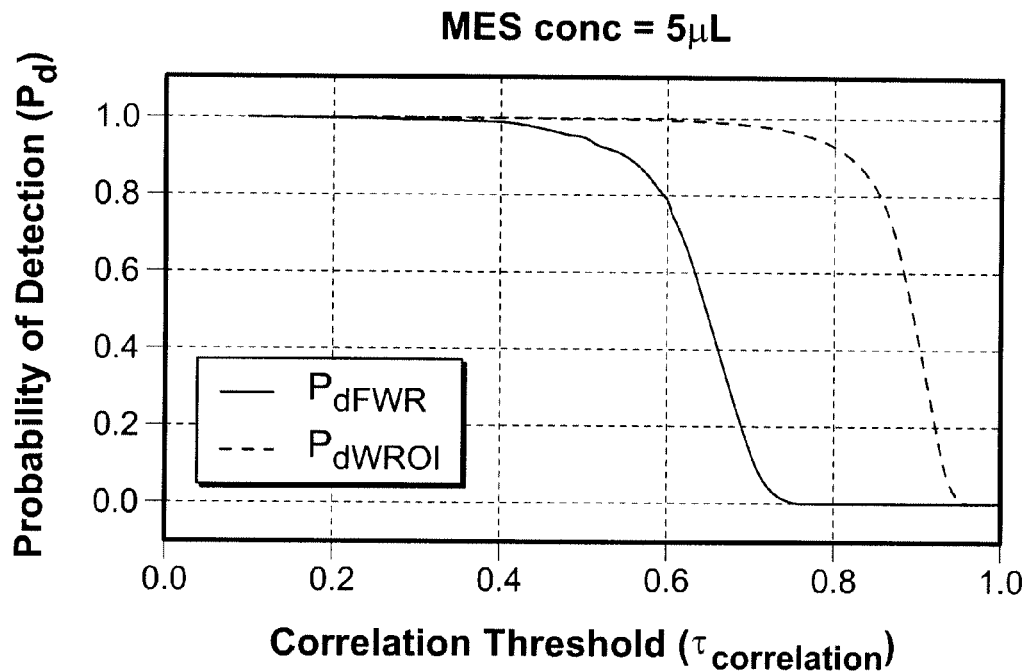
Figure 24D:
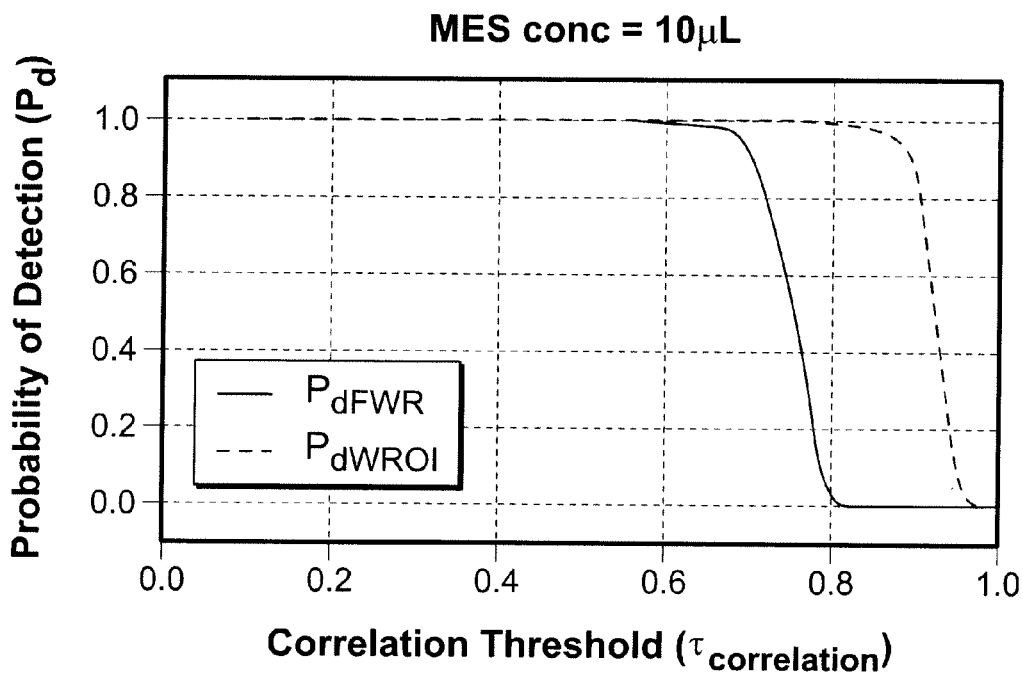
Figure 25A:
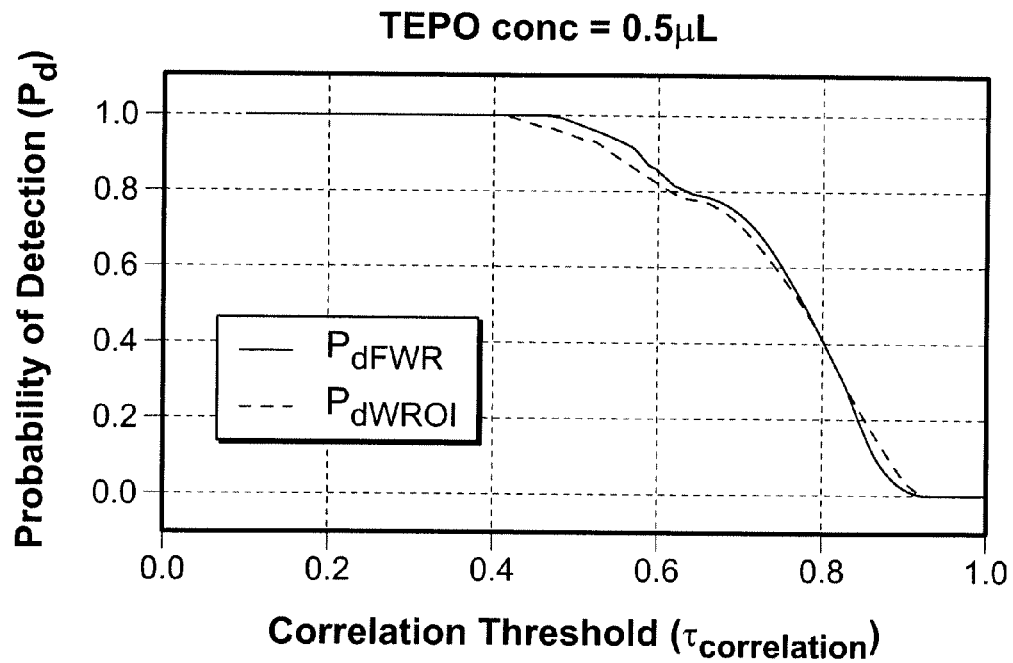
FIGS. 25A-D are plots of SWTPE performance on triethylphosphate (TEPO) data for N=1 in accord with at least some aspects of the present concepts.
Figure 25B:
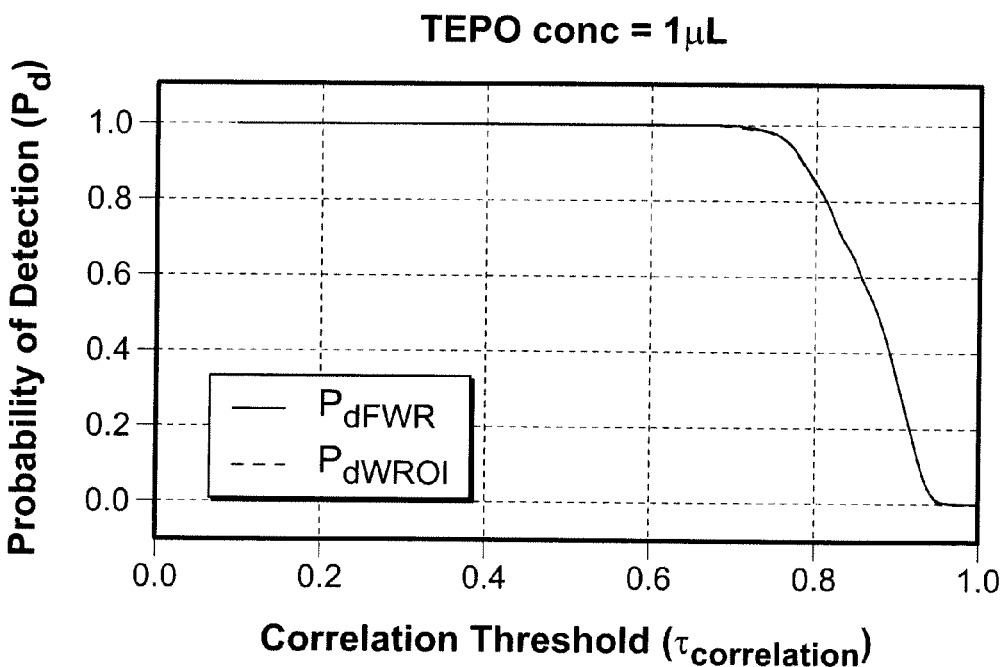
Figure 25C:
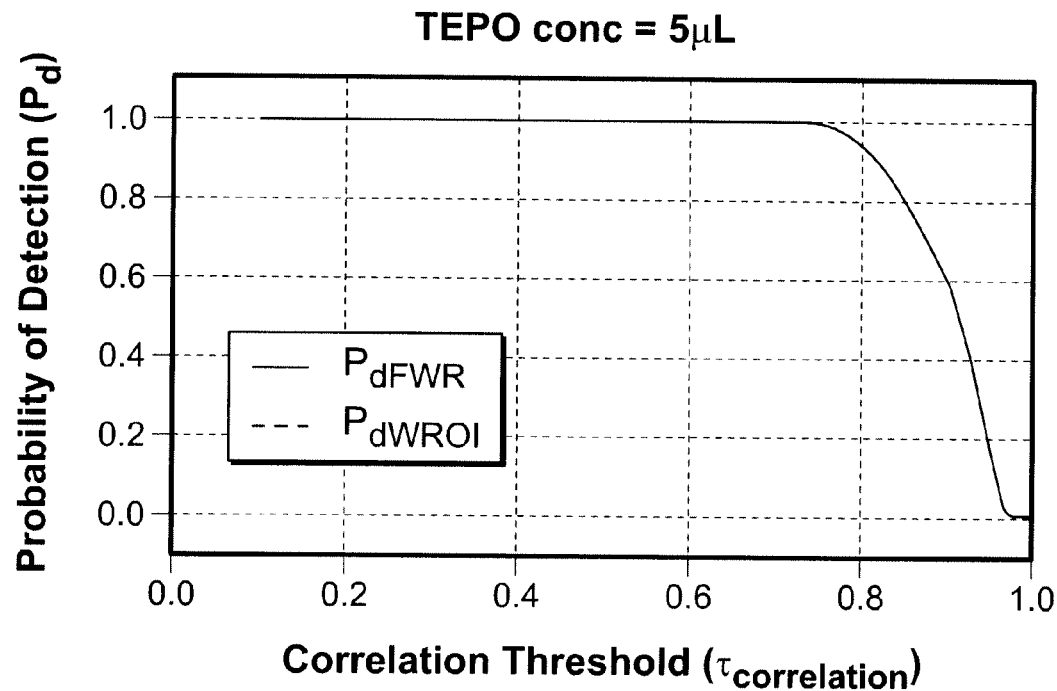
Figure 25D:
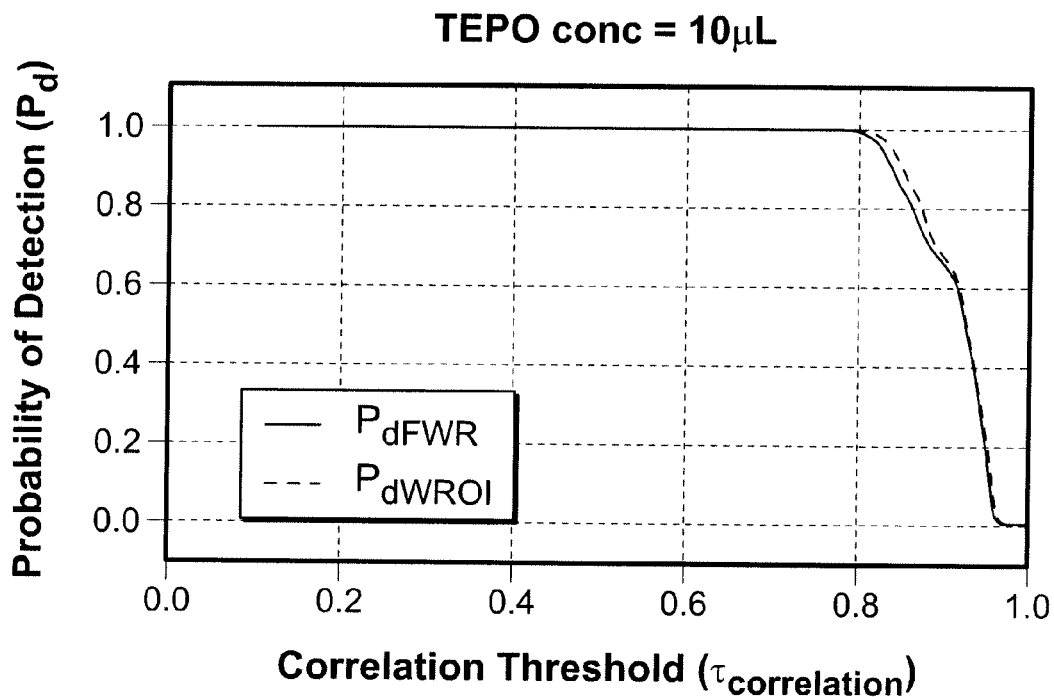
Figure 26A:
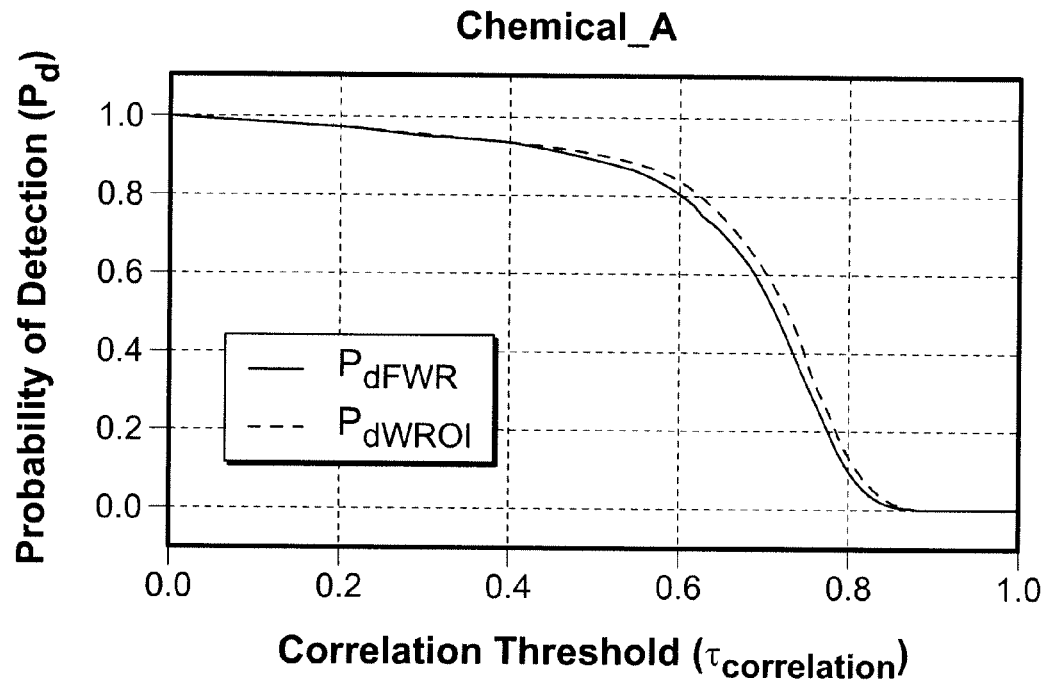
FIGS. 26A-D are plots of SWTPE performance on Dataset 4 for N=1 with only Nitrogen and Oxygen peaks truncated in both measured and library spectra, in accord with at least some aspects of the present concepts.
Figure 26B:
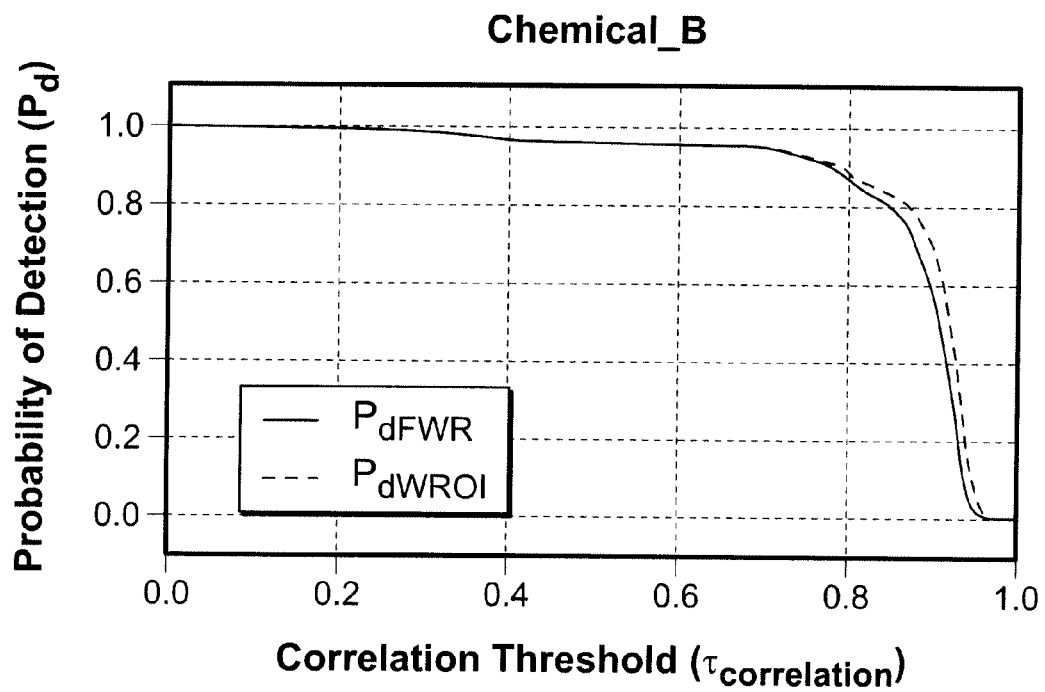
Figure 26C:
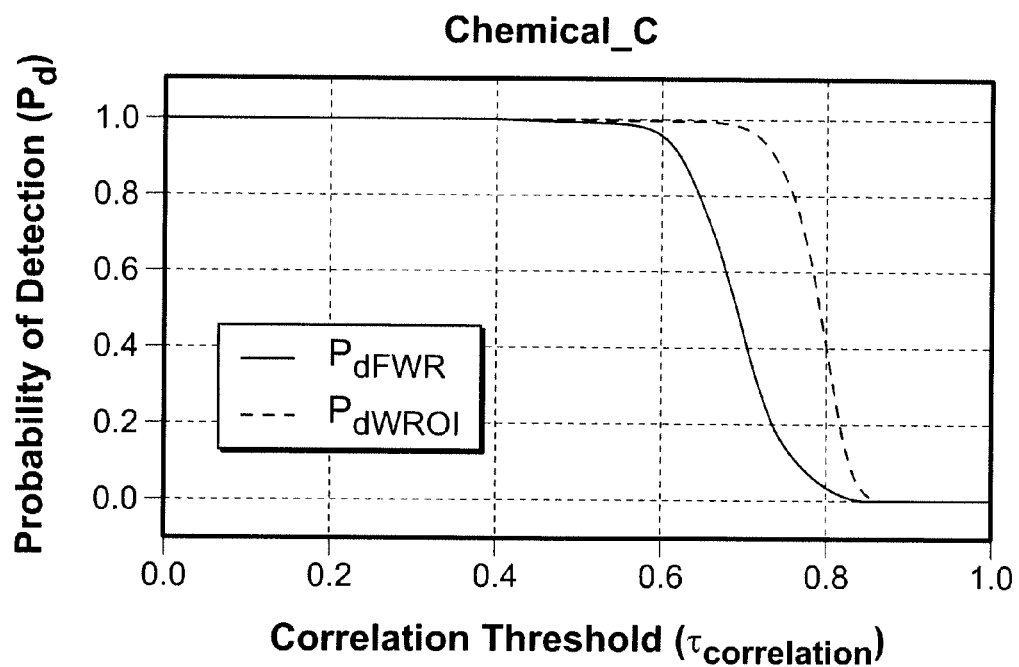
Figure 26D:
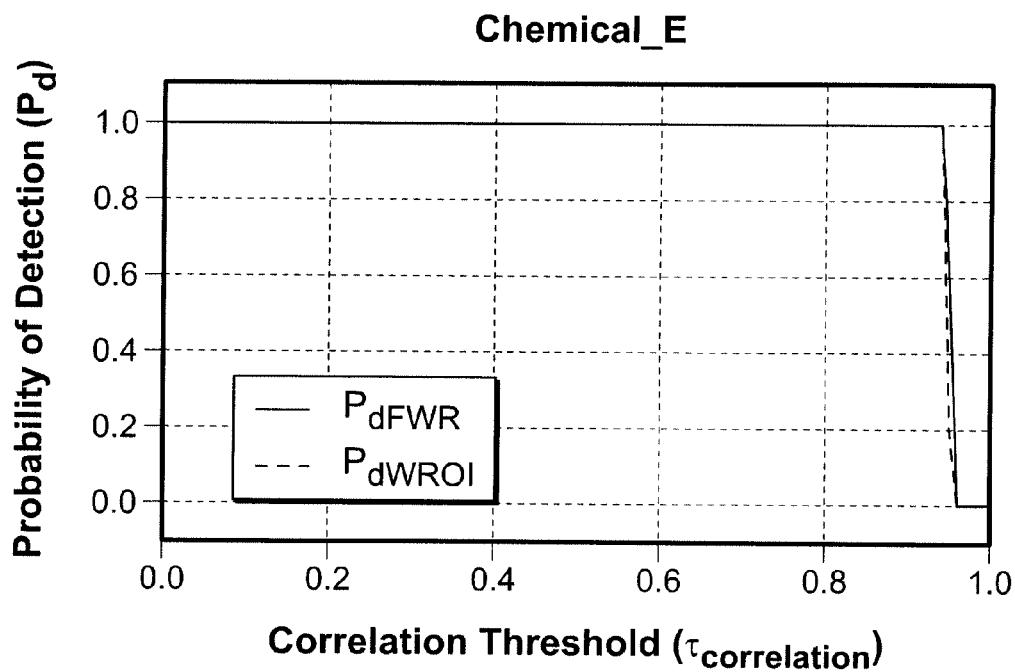
Figure 27A:
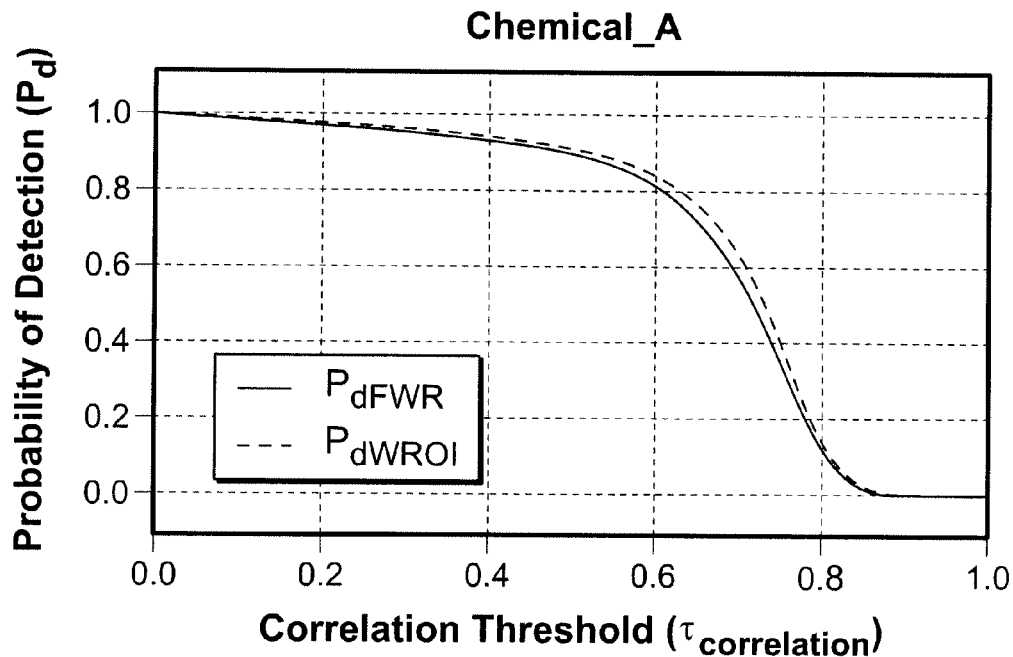
FIGS. 27A-D are plots of SWTPE performance on Dataset 4 for N=1 with only Nitrogen, Oxygen, and Carbonate peaks truncated in both the measured and library spectra, in accord with at least some aspects of the present concepts.
Figure 27B:
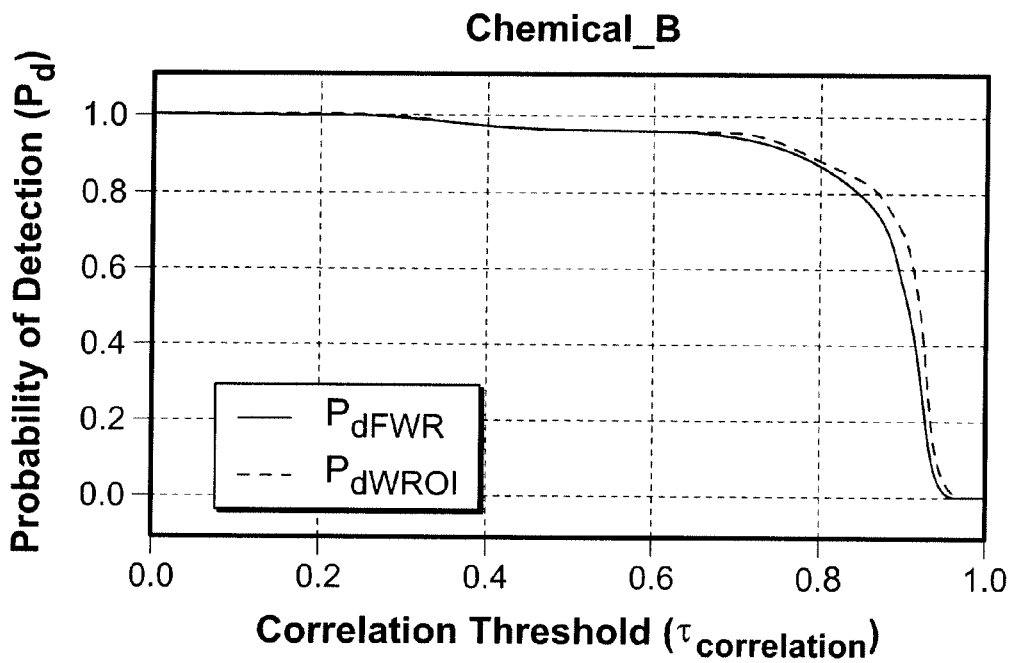
Figure 27C:
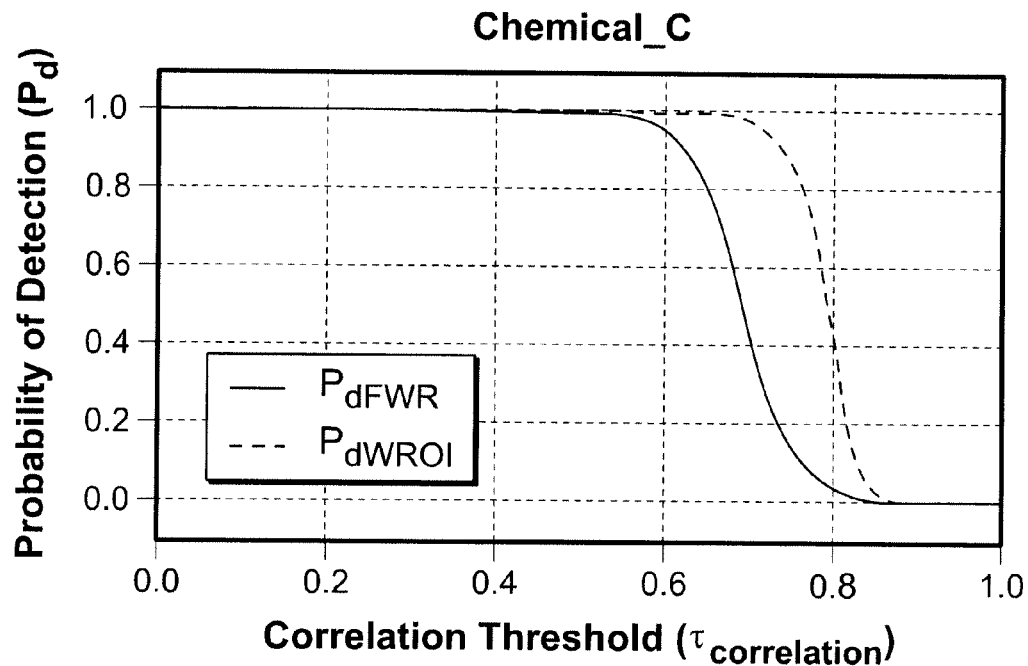
Figure 27D:
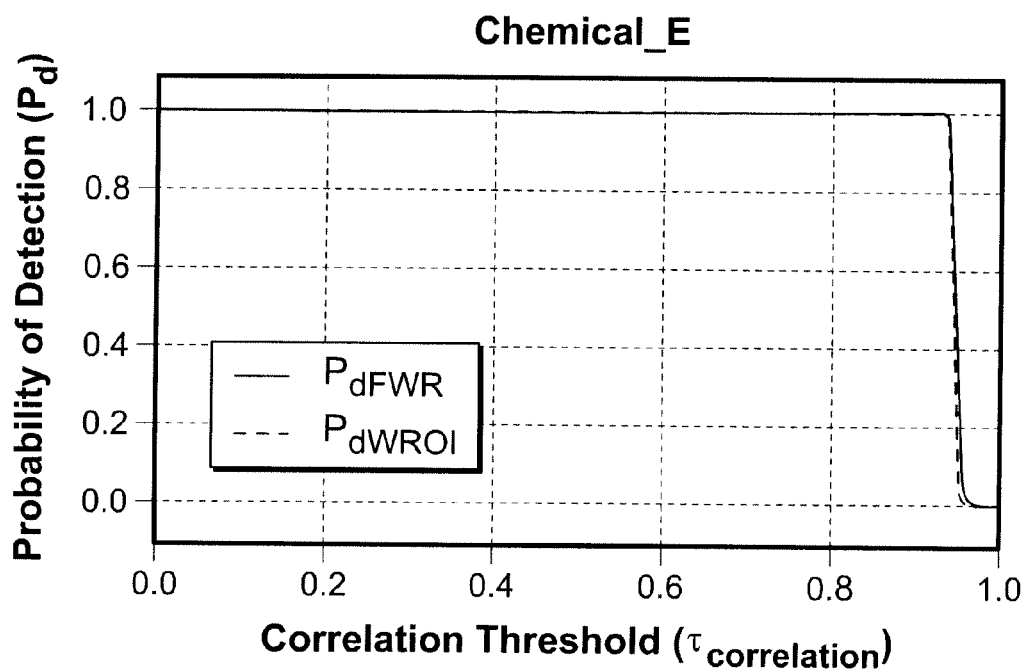
Figure 28A:
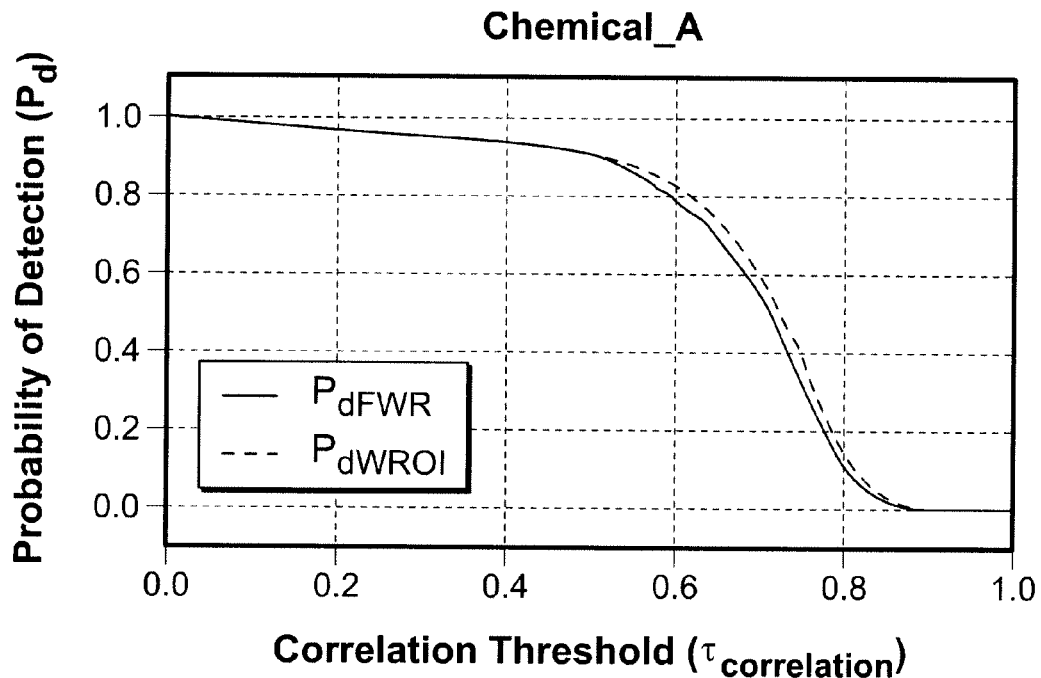
FIGS. 28A-D are plots of SWTPE performance on Dataset 4 for N=1 with Nitrogen, Oxygen, Carbonate, and Asphalt/Concrete interfering peaks truncated in both the measured and library spectra, in accord with at least some aspects of the present concepts.
Figure 28B:
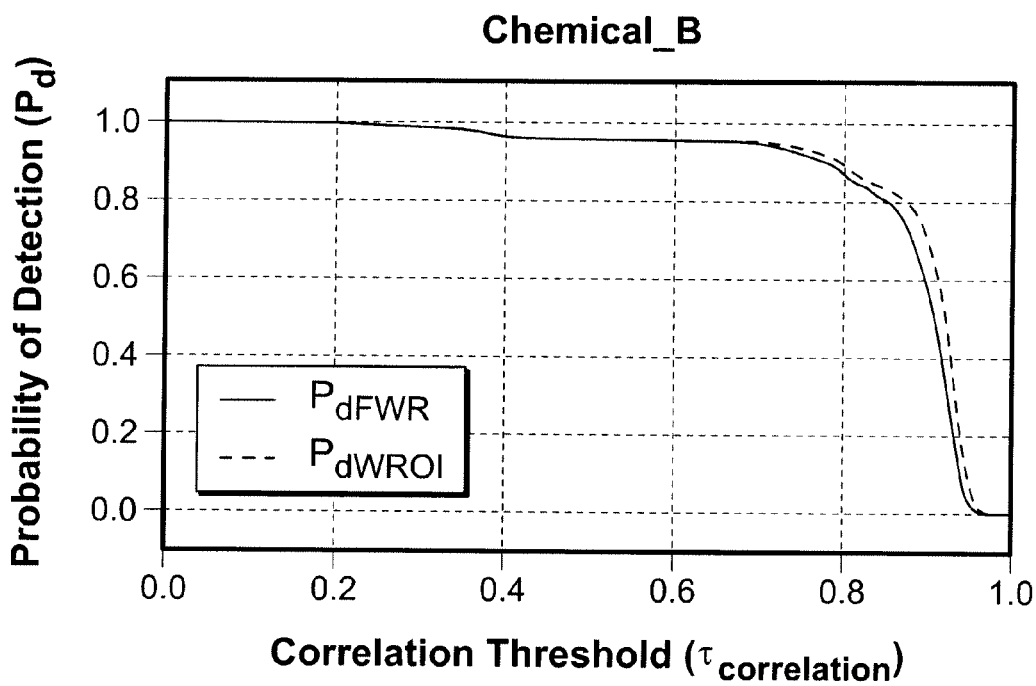
Figure 28C:
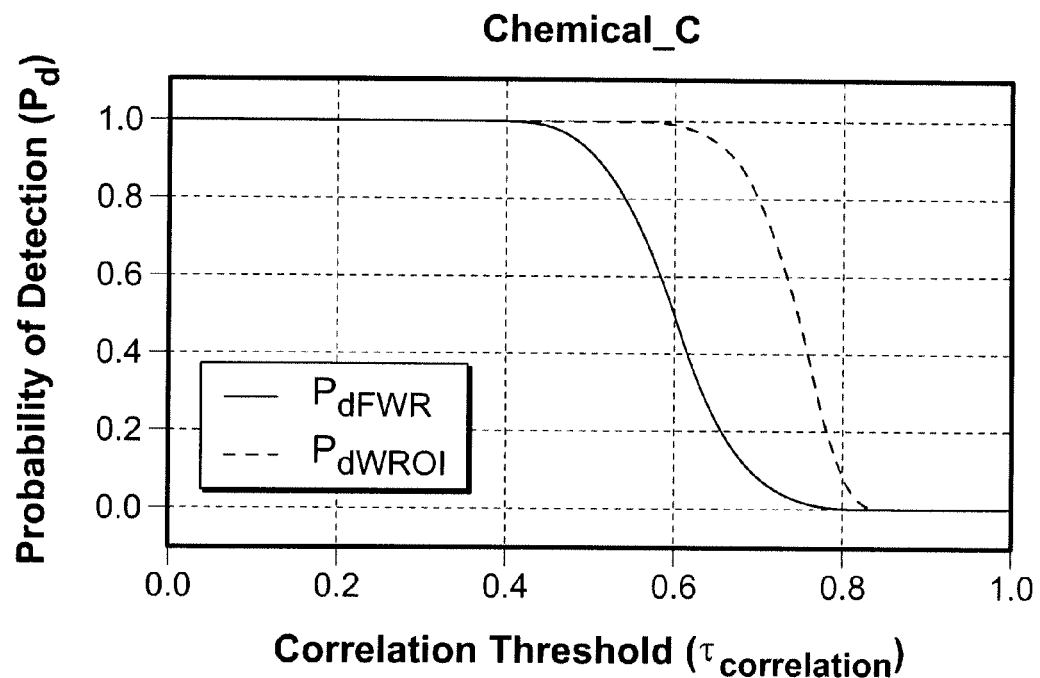
Figure 28D:
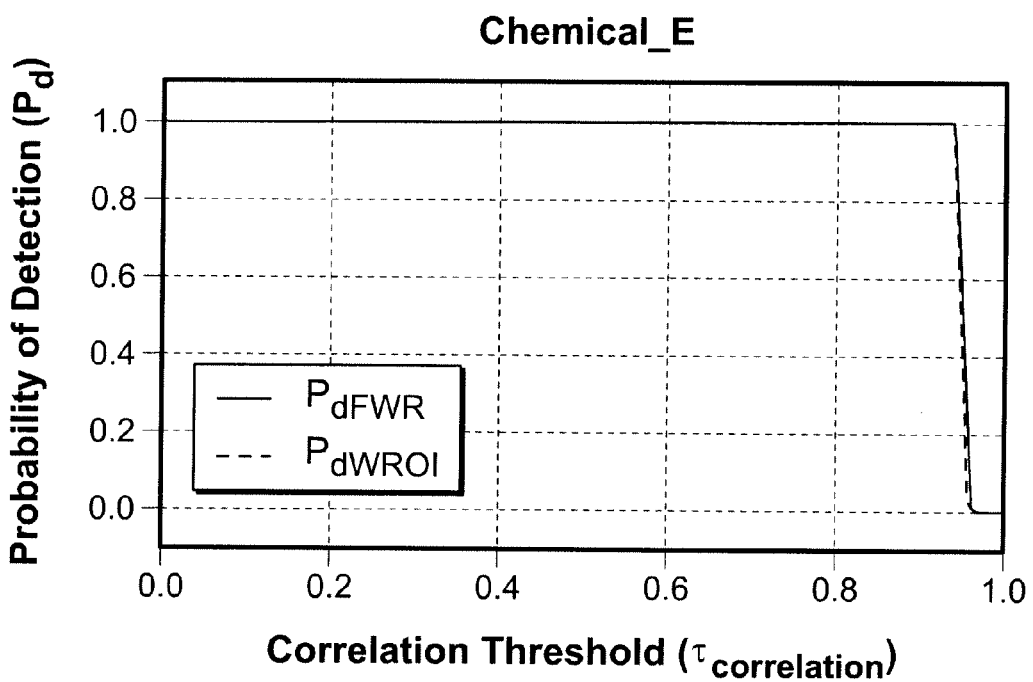
Figure 29A:
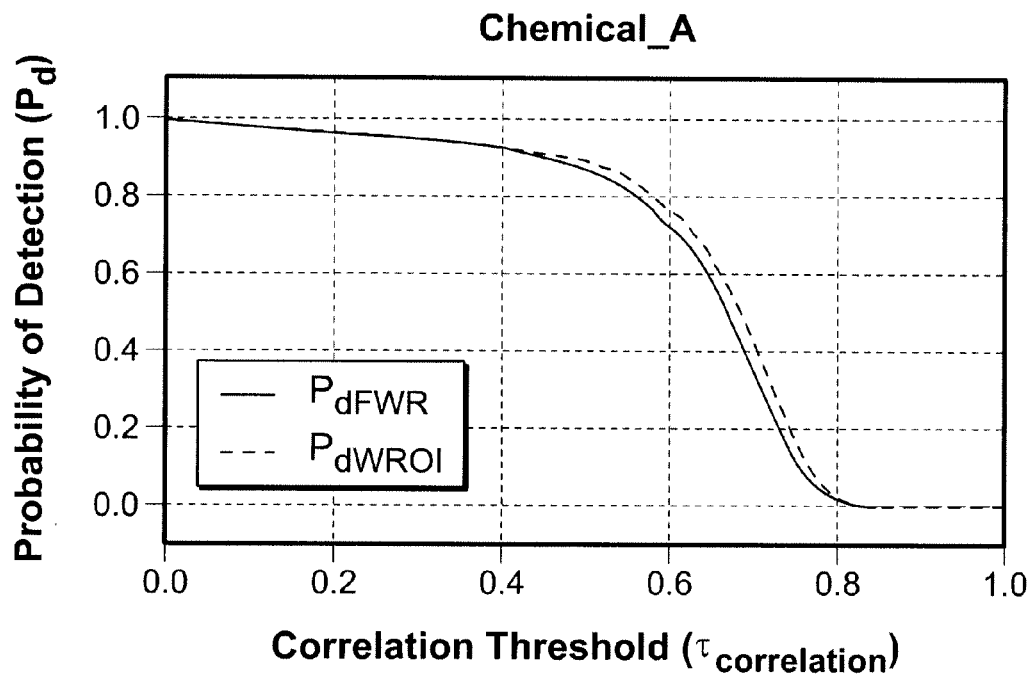
FIGS. 29A-D are plots of SWTPE performance on Dataset 4 for N=1 with Nitrogen, Oxygen, Carbonate, and Asphalt/Concrete interfering peaks truncated in only the measured spectra, in accord with at least some aspects of the present concepts.
Figure 29B:
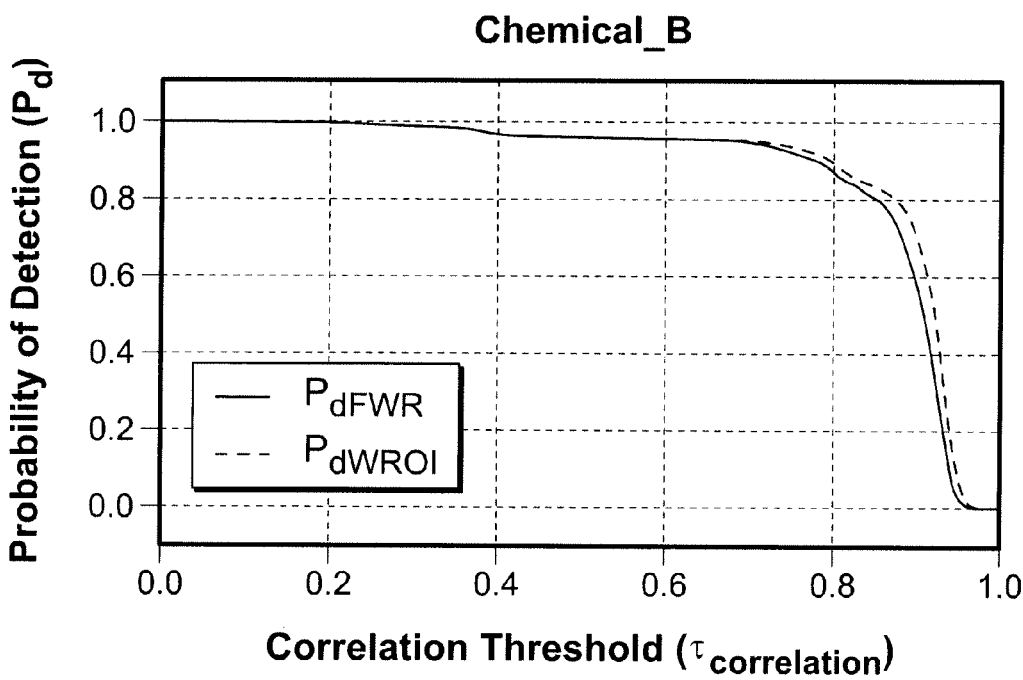
Figure 29C:
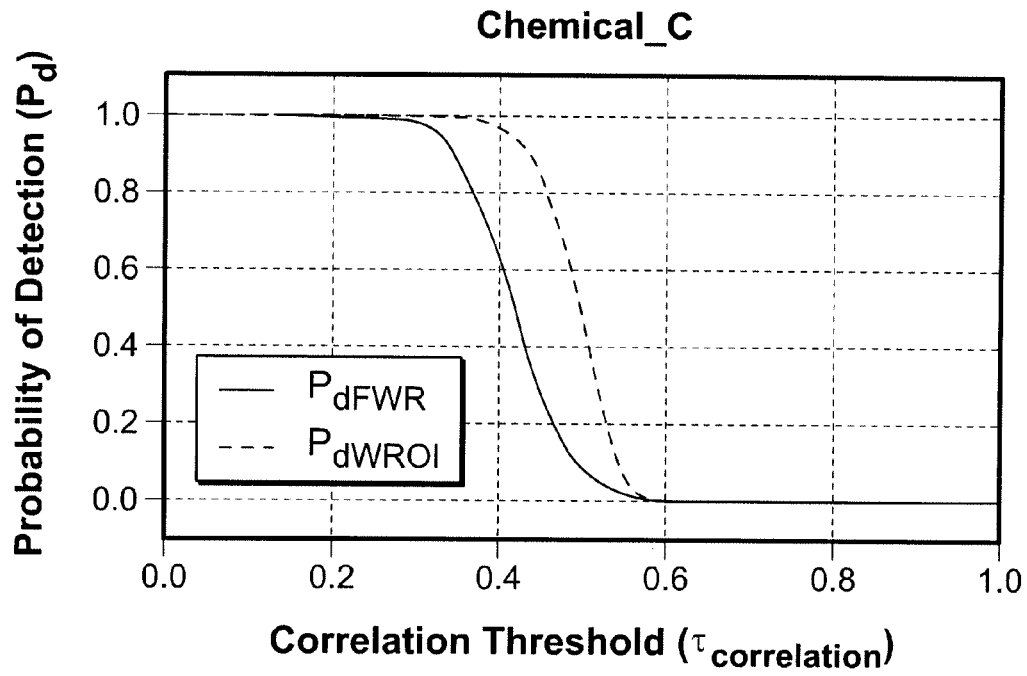
Figure 29D:
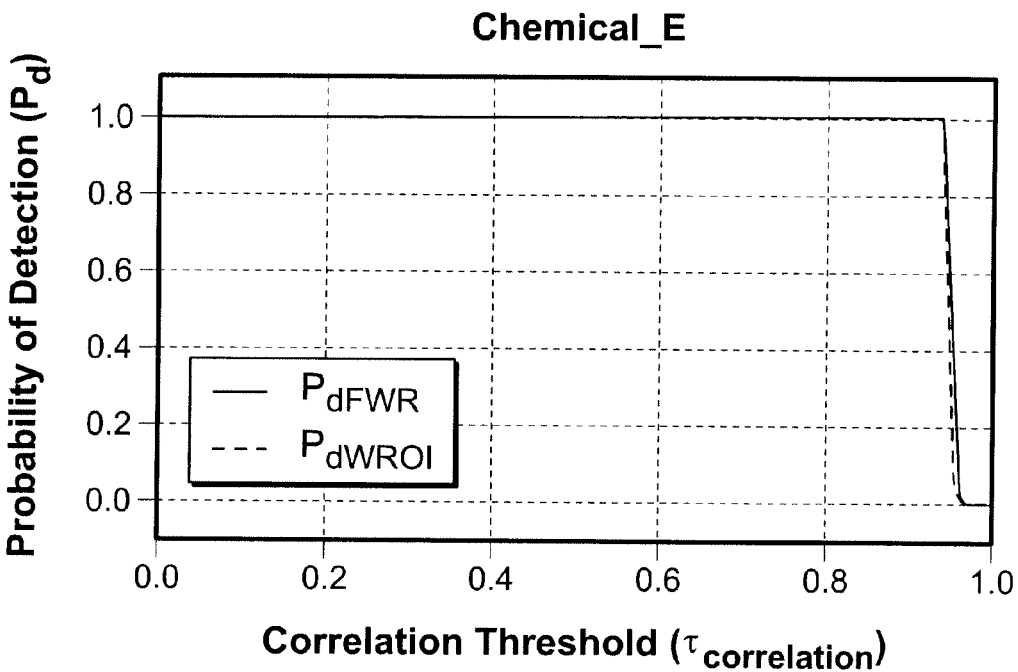
Figure 30A:
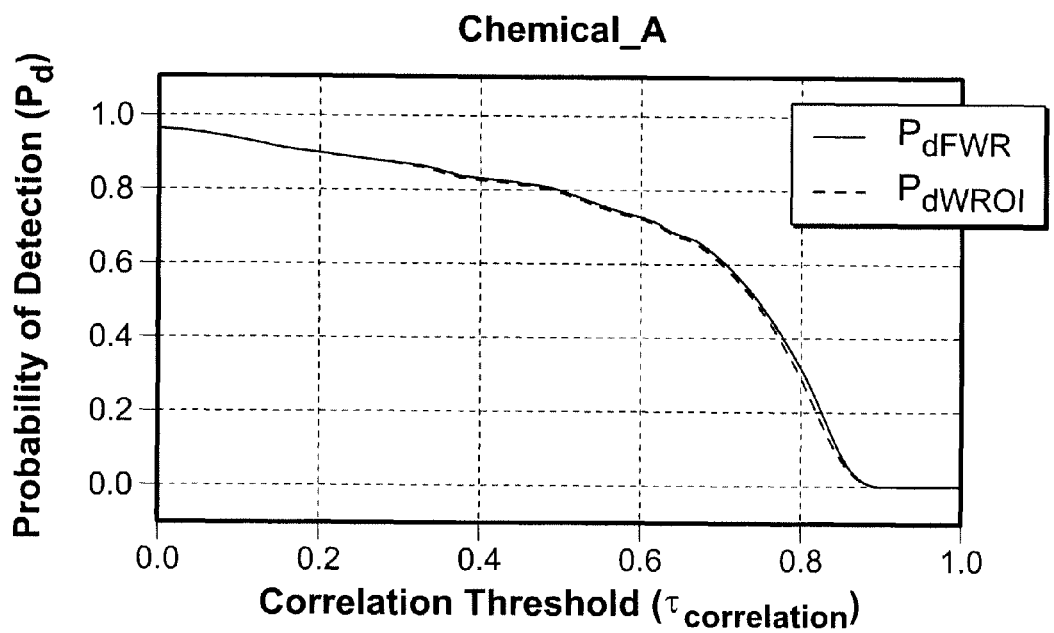
FIGS. 30A-D are plots of SWTPE performance on Dataset 5 with concrete background for N=1 in accord with at least some aspects of the present concepts.
Figure 30B:
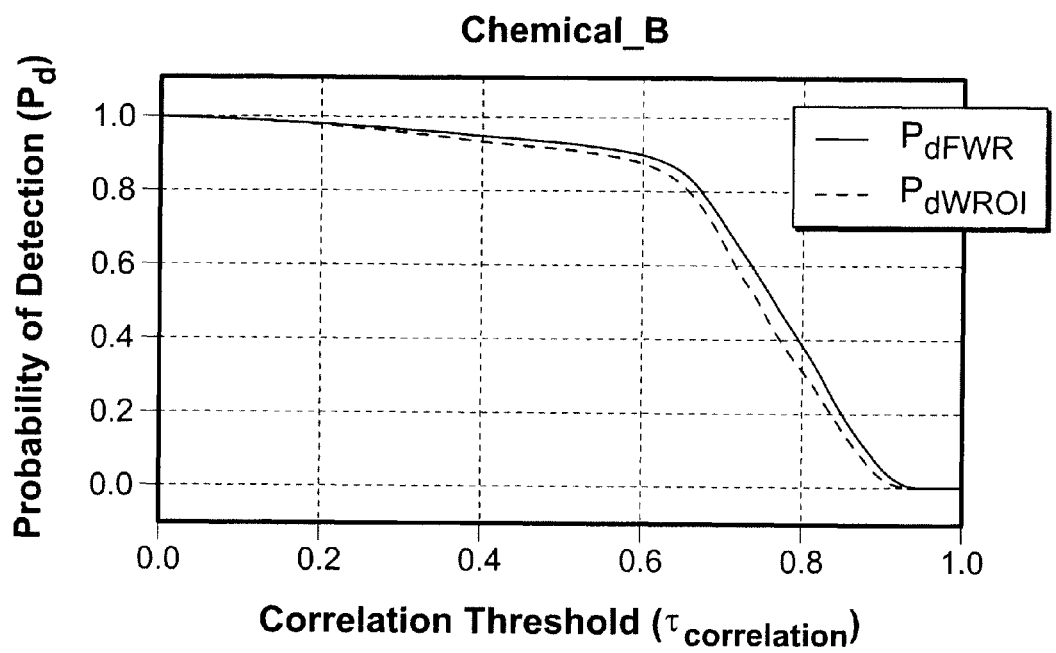
Figure 30C:
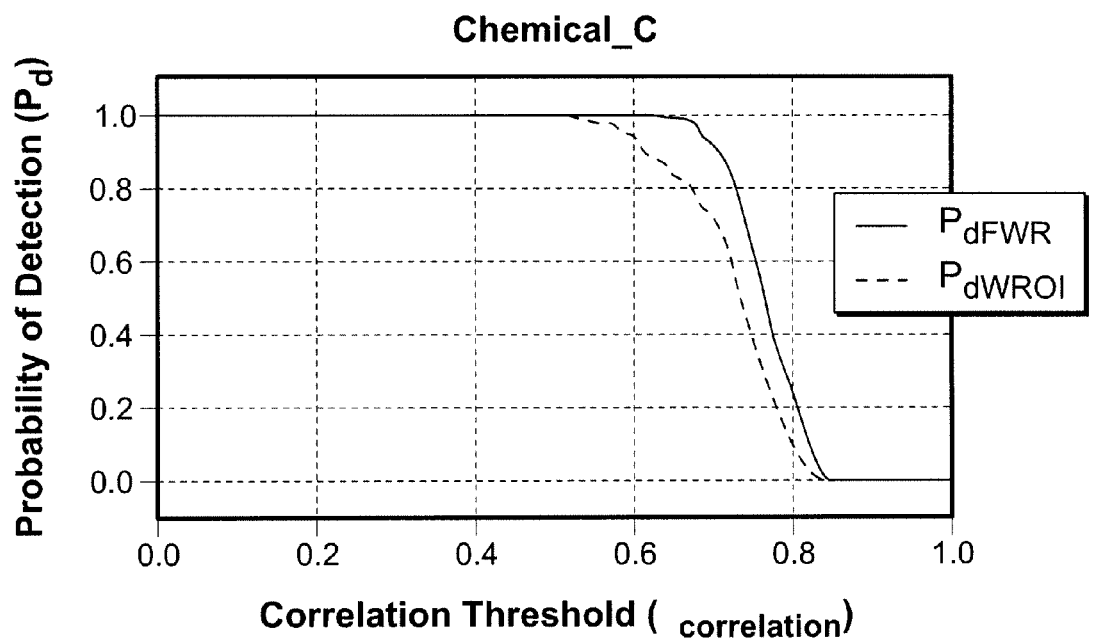
Figure 30D:
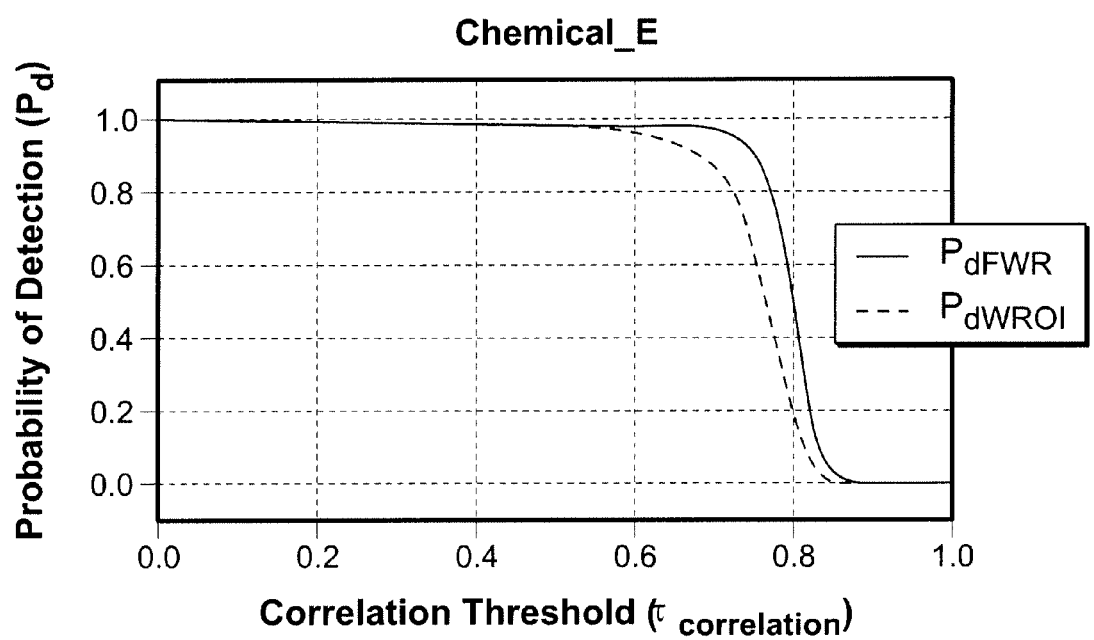
Figure 31A:
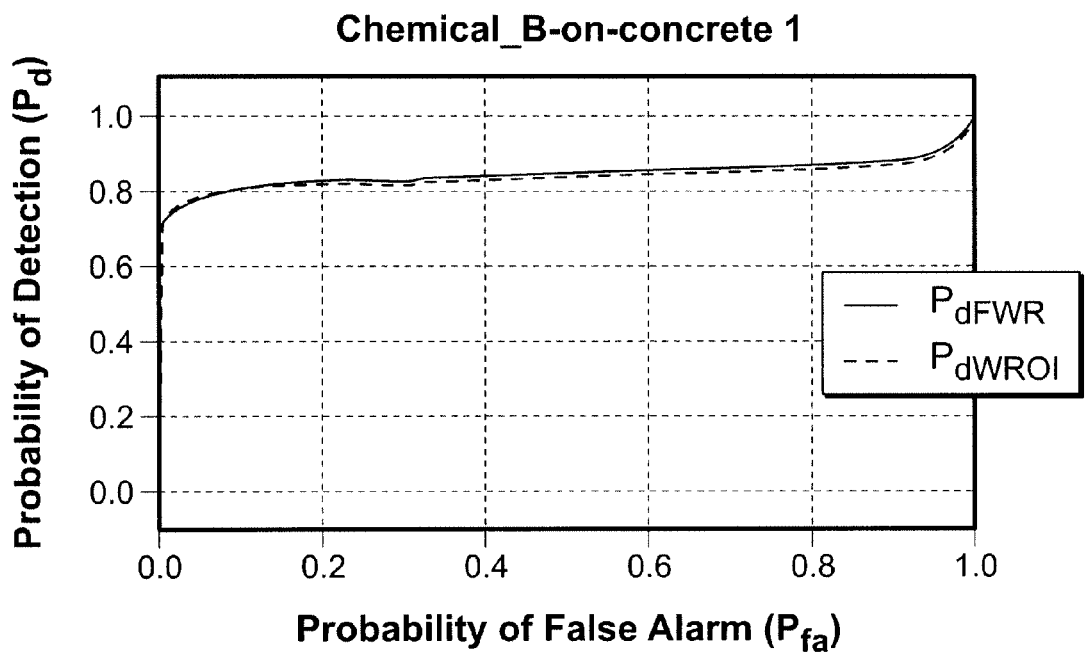
FIGS. 31A-D are plots of receiver operating characteristics (ROC) curves corresponding to Dataset 6 in accord with at least some aspects of the present concepts.
Figure 31B:
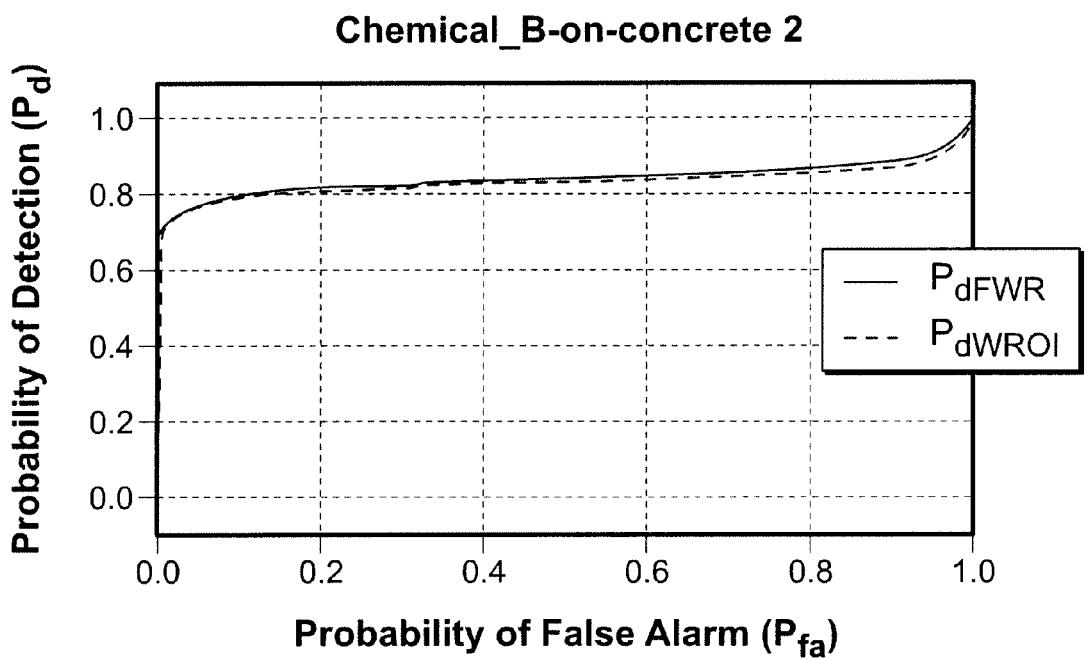
Figure 31C:
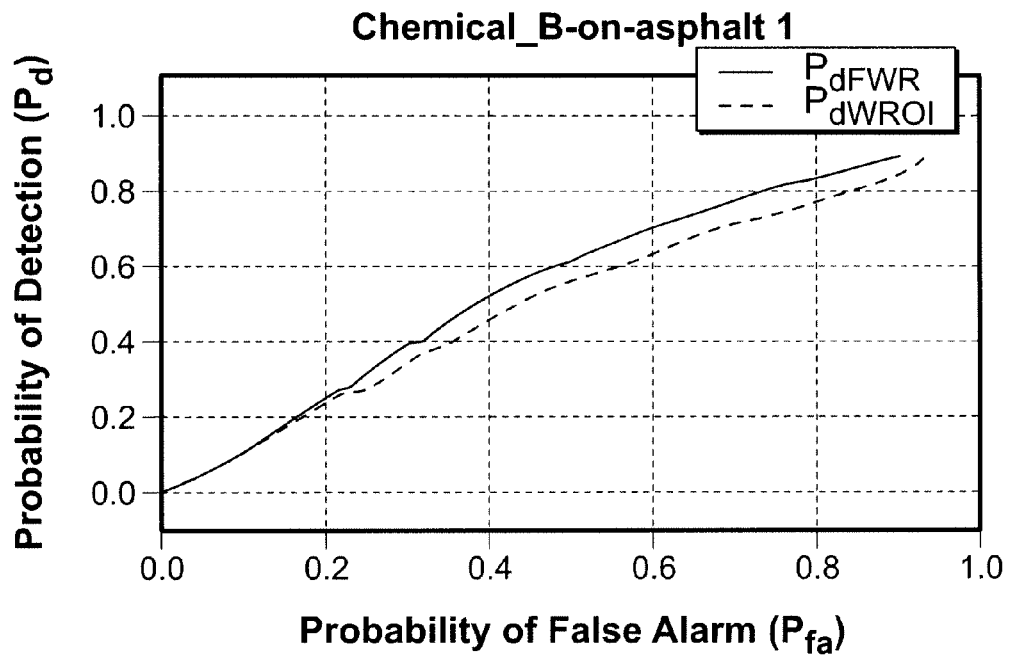
Figure 31D:
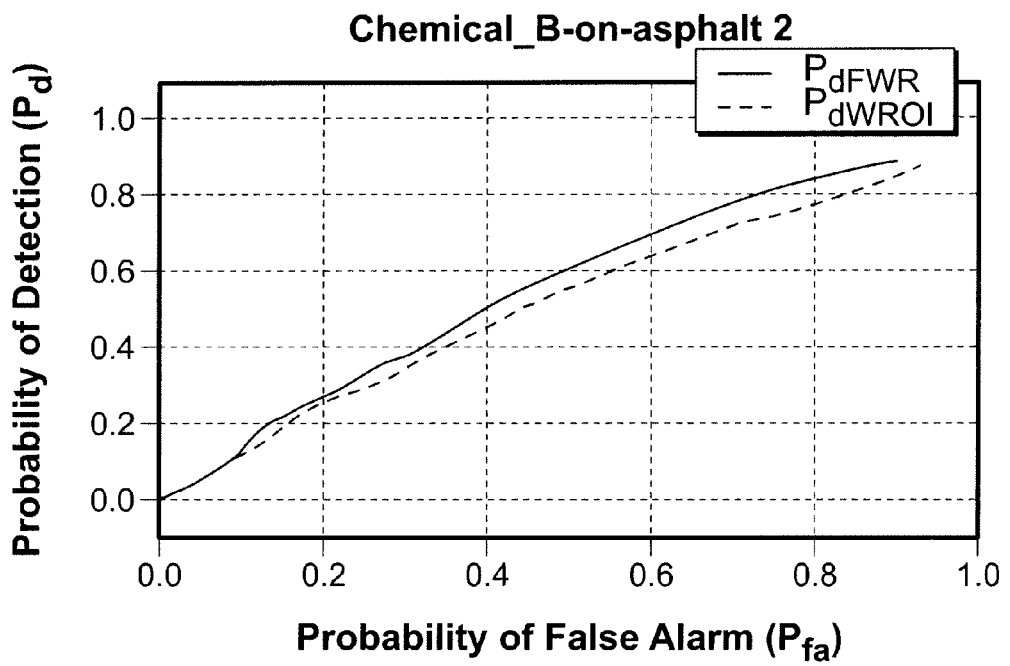

FIG. 21-23 show $P_d$ versus $\tau_{correlation}$ corresponding to TMeS-on-gravel for N=25, 15, and 1, respectively. It can be seen from these curves that they are similar to the LIPE curves of FIGS. 15-17. For N=1, however, the LIPE seems to perform better than SWTPE. This could be caused by suboptimal sliding-window lengths. The LIPE has no dependence on the data in terms of how it processes the data. However, the SWTPE has two data dependent parameters, as mentioned above, that can alter the way it processes two different spectra. The relative performance drop of SWTPE may be attributed to this fact. The drop in performance, however, is not significant.

Having understood the importance of single spectrum processing, Dataset 3 was analyzed via the SWTPE algorithm for N=1. Both FWR and WROI correlation coefficients were computed and the two corresponding $P_d$ were obtained. They are designated as $P_{dFWR}$ and $P_{dWROI}$, respectively. FIGS. 24 and 25 show these probabilities ($P_{dFWR}$ as a solid line and $P_{dWROI}$ as a dashed line) versus $\tau_{correlation}$ for four different concentrations of MES and TEPO, respectively. In most concentrations of MES the $P_{dFWR}\approx 0$ at $\tau_{correlation}<0.9$, whereas $P_{dWROI}\approx 1$ at $\tau_{correlation}=0.9$. WROI correlation has a significant advantage because it does not consider the noise regions while comparing the measured and library spectra.

In the case of TEPO, however, there is no significant advantage in WROI correlation because the wavenumber ranges excluded from WROI seem to be fairly low in energy content. Thus, although WROI correlation may not always yield a higher $P_d$, it will not decrease it.

Four chemicals in Dataset 4, designated Chemical_A, Chemical_B, Chemical_C, and Chemical_E, were analyzed for N=1. These chemicals were not placed on any background that has a Raman signature. Therefore, apart from the air signature there is no other interference. Chemical_A is a chemical that is known to seep into the background resulting in a weak chemical signature. Chemical_C is TMeS and Chemical_E is a chemical that is difficult to detect when placed on concrete.

Truncating air peaks is essential, as the air signature (i.e., Nitrogen and Oxygen) is present in all chemical spectra. FIGS. 26A-D show the $P_d$ versus $\tau_{correlation}$ for the four chemicals when the air peaks are truncated in both the measured and the library spectra. It is seen that except for Chemical_A, all other chemicals have $P_{dWROI}>0.8$ for $\tau_{correlation}=0.7$. Chemical_A, on the other hand, due to its weak Raman signature, yields $P_{dWROI}\approx 0.6$ at $\tau_{correlation}=0.7$.

In order to demonstrate the effects of truncating interfering peaks, FIGS. 27A-D show the $P_{dWROI}$ versus $\tau_{correlation}$ plots when the air signature and the Carbonate peak are truncated. FIGS. 28A-D show the $P_{dWROI}$ curve when the air signature, Carbonate, and asphalt/concrete peaks are truncated. The truncation is performed in both the measured and the library spectra. It can be seen from these figures that $P_{dWROI}$ does not alter significantly even when more interfering peaks are truncated. This is true only when truncation is performed in both the measured and library spectra.

To demonstrate the effect of truncating the interfering peak only in the measured spectra, FIGS. 29A-D show the $P_{dWROI}$ versus $\tau_{correlation}$ curves obtained by truncating all the four interfering peaks only in the measured spectrum. It is evident from the $P_{dWROI}$ curve of Chemical_C that the detection performance is severely affected by truncating interfering peaks only in the measured spectrum. It should be noted that this drastic reduction in detection performance is not necessarily true for all chemicals as evidenced from the $P_{dWROI}$ curves of Chemical_A, Chemical_B, and Chemical_E. This happens because their Raman signatures do not overlap with any of the truncated interfering peaks. However, to maintain generality, it is best to truncate all four interfering peaks in both the measured and library spectra.

We know for certain that the spectra of Dataset 4 do not contain any background signature. The spectra in Dataset 5, however, contain the concrete signature as they are measurements of chemical-on-concrete. The detection performance is analyzed for this dataset to evaluate the methodology of processing interfering peaks. FIGS. 30A-D show the $P_{dWROI}$ versus $\tau_{correlation}$ for the four chemicals placed on concrete. It should be noted that the detectability of Chemical_A is reduced owing to its seepage into the background. It yields $P_{dWROI} \approx 0.6$ at $\tau_{correlation}=0.7$. On the other hand, Chemical_E, which is more difficult to detect on concrete, has $P_{dWROI} \approx 1$ at $\tau_{correlation}=0.7$. Chemical_B and Chemical_C also yield $P_{dWROI}$ 0.8 and 0.9, respectively, for $\tau_{correlation}=0.7$.

FIGS. 31A-D show four ROC curves, two each corresponding to Chemical_B on concrete and asphalt, respectively. It is seen from the two ROC curves corresponding to Chemical_B-on-concrete that the SWTPE algorithm performs reasonably well, yielding $P_{dWROI}=0.8$ for $P_{fa}$ as low as 0.1. The $P_{dFWR}$ is nearly the same as $P_{dWROI}$ just as in the case of Dataset 4 and 5.

Surprisingly, the two ROC curves corresponding to Chemical_B-on-asphalt are nearly linear indicating that the SWTPE does not detect the chemical. However, because Chemical_B reacts with asphalt, resulting in a new chemical, it can be asserted that the SWTPE algorithm indeed performs well in detecting Chemical_B, as well as rejecting non-Chemical_B spectra.

Based on the above performance results, some conclusions can be drawn. The LIPE yields good detection rates for reasonably large drop diameters ($\geq 1.43$ mm) of TMeS. The pedestal estimation works well to minimize the effects of the pedestal. The LP filter, also supports LIPE reasonably well in accurately estimating the pedestal. The air signature truncation from the TMeS data further boosts the detection rate.

The LIPE, however, suffers from breakages of multiplets. This effect, nonetheless, is inconsequential to detection performance because as long as the library and measured data are processed similarly, the correlation coefficient will not decrease.

The SWTPE, designed to address the multiplet splitting problem yields results comparable to LIPE's results. This in itself is a highlight of SWTPE. Some optimization may be performed via mapping the window domains in each run and stopping a run if the current window domain overlaps with a domain of a previous run. The basis for this optimization is that when a window domain overlaps with a domain from a previous run, the subsequent domains will be the same and, therefore, the pedestal estimates will be the same from that domain onwards.

Although SWTPE may be favored over LIPE in some instances because of its multiplet retention capability, LIPE yields nearly the same $P_d$ curves. It is seen that averaging (N=25) substantially improves the detectability of various TMeS drop-diameters via both algorithms. Further, processing a single spectrum decreases the detection rates of small drop-diameters for both algorithms; nonetheless, SWTPE shows marginally better $P_d$ curves for smaller drop-diameters. It can be inferred, therefore, that the correlation coefficients will remain nearly the same as long as the measured and library spectra are similarly processed.

This is true also for the interfering peak truncations; it was demonstrated by SWTPE results for Dataset 4 that if the interfering peaks are truncated in both the measured and library spectra, then the correlation coefficients will remain nearly the same. If more interfering signatures are identified, then truncating all of them might result in the target Raman signature being retained only in a very narrow wavenumber range compromising the detection capability of the algorithm.

The SWTPE results for Dataset 3 showed that WROI correlation increases $P_d$ significantly in some chemicals. It was also shown that WROI correlation does not decrease $P_d$ in the event of the ignored regions lacking sufficient energy. A cause of concern for WROI correlation, however, is that when two chemicals have nearly the same WROIs, then they need to be grouped into a class. WROI correlation may then be used to identify classes of chemicals instead of individual chemicals. Additional processing will be required to discriminate chemicals belonging to the same class.

Finally, the results of SWTPE on Dataset 6 showed that it can detect chemical spectra randomly present among background spectra with a detection rate of ≈0.8 and a false alarm ≈0.1. Further, the validation of the linear ROC curves corresponding to Chemical_B-on-asphalt corroborates the algorithm's reasonably high detection and rejection capability.

In developing the SWTPE algorithm the pedestal in a given spectrum was considered as a single slow-varying entity spanning the entire spectral range. Consequently, the Raman signature of the chemical was also considered as a single entity. This treatment of the data is useful because it allowed the formulation of the pedestal as an approximation to the lower envelope of the measured spectrum. In doing so, however, the pedestal is estimated also in spectral regions that do not contain any chemical information resulting in processing redundancies. The SWTPE was developed without regards to computational constraints owing to the fact that averaging N spectra reduces the frequency of the algorithm's use to once per N measurements. Collecting N spectra from the same source may impose undesirable operational constraints. Single spectrum processing (SSP), therefore, became more appropriate for the operational demands. Although SWTPE yields good detection results for SSP, its speed of processing may be a concern for some applications.

In accord with another embodiment of at least some other aspects of the present concepts, an alternative approach for addressing the pedestal only in the spectral regions where chemical signature may be present is thus desirable. In order to identify such spectral regions, it is imperative to assess the likelihood of chemical information being present in the measured data at those spectral regions. A feature, in general, is defined as that part of a curve whose first and last sample points are local minima of the curve, and there exists a local maximum of the curve between the two minima. Every spectral data, consequently, can be represented as a series of adjacently placed spectral features if no local extreme points of the same kind (maxima or minima) appear successively. In other words, every local minimum must alternate with a local maximum. Local extreme points have so far been defined via identification of zero-crossing/touching of the difference of the spectral data as described above.

Figure 32A:
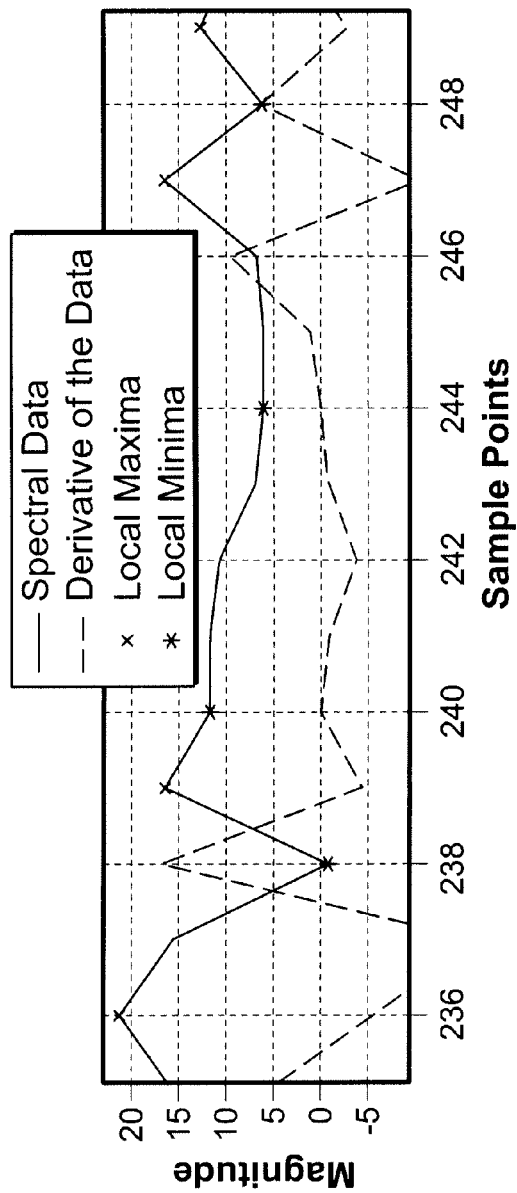
FIG. 32A is a plot of spectral data having consecutive local minima in accord with at least some aspects of the present concepts.
Figure 32B:
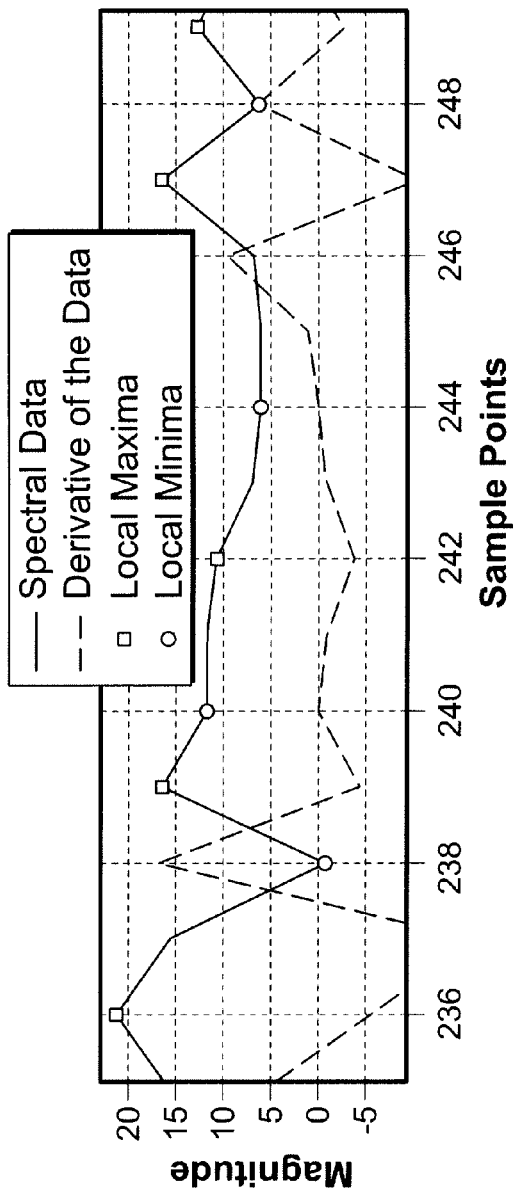
FIG. 32B is a plot of spectral data having a local maximum introduced between the consecutive local minima shown in FIG. 32A.

In some spectral data, however, local extreme points occur consecutively. For example, FIG. 32A shows a region of the spectrum (shown as a solid line) where the data seems to have two local minima successively (at sample points 240 and 244). This scenario occurs when the difference touches zero but does not change sign. When the difference once again touches or crosses zero, its sign is the same as before and, therefore, a local extreme of the previous kind is identified again. A modification to the local extreme points identification technique was necessitated, therefore, so that a spectral data can be represented as a series of consecutive features. Primarily, where there were two consecutive local minima (or maxima) points, a local maximum (or minimum) was introduced at the sample point corresponding to the minimum (or the maximum) of the derivative (shown as a dashed line). FIG. 32B shows new alternating local extreme points obtained using this modification to the technique of identifying extreme points.

The advantage of representing spectral data as a series of consecutive features is that: (a) each feature can be processed separately providing a higher degree of freedom, (b) only chemical signature features can be extracted from the data and used for comparisons with the library set, and (c) the speed of processing can be increased because fewer features need to be processed.

Signature features in reasonably high (SINR) spectral data can be identified in several ways: feature magnitude, feature width, and/or feature location. Feature magnitude provides a good estimate of the feature's importance in terms of its contribution to the spectral signature and energy. Pedestal effects, however, can increase magnitudes of noisy features leading to ambiguity in the true source of the feature's energy and true contribution to the chemical's signature. Feature width is also a good indicator of the feature's importance, again in terms of its spectral energy and signature contribution. As a result of additive noise, broad features are often characterized as a series of smaller consecutive features, thereby rendering feature width ineffective in identifying the broad signature. Feature location is another valid indicator of the feature's importance in terms of the match between the measured data and the library spectrum. With many library spectra available to compare with the measured spectrum, any use of the feature location proves to be computation intensive.

Figure 33:
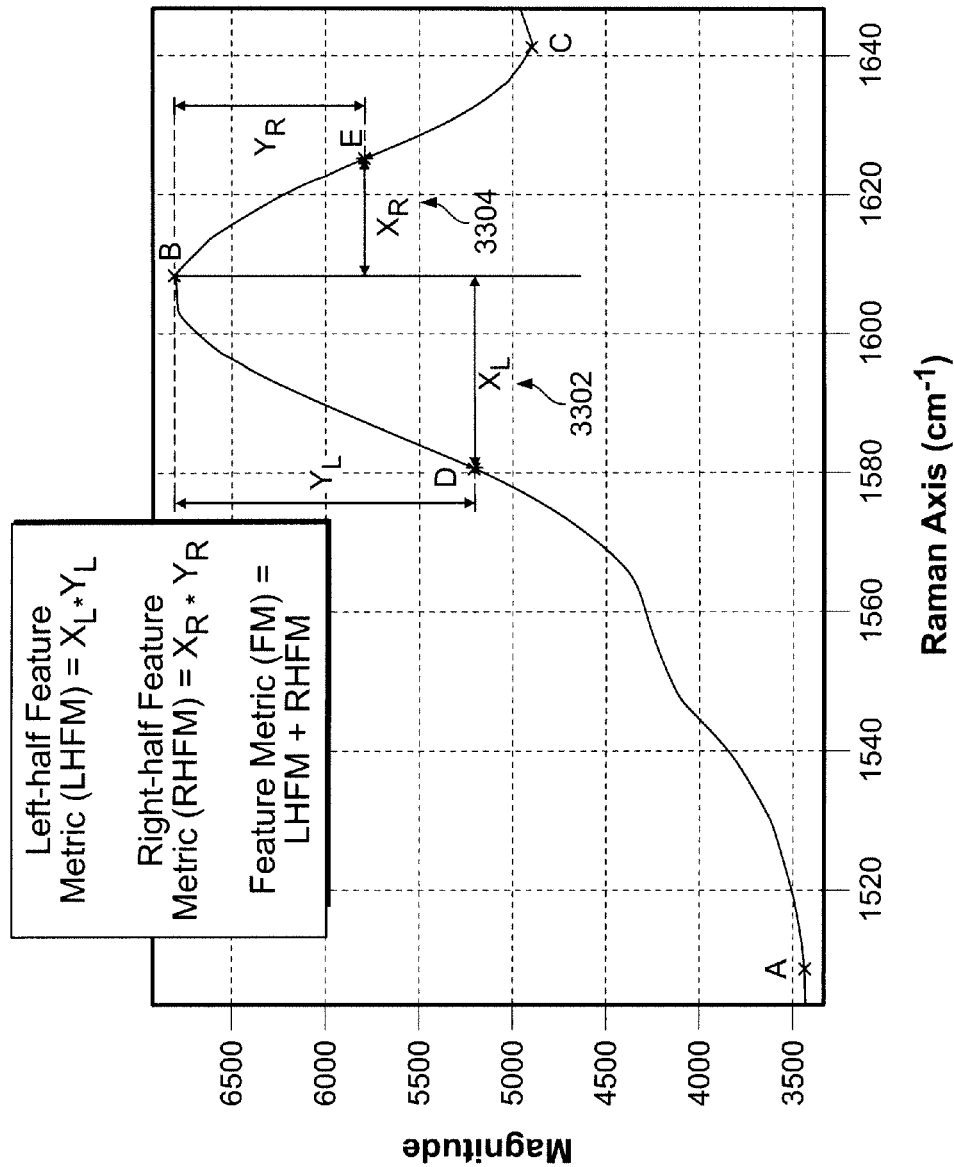
FIG. 33 is a plot of a feature metric computation in accord with at least some aspects of the present concepts.

In order to define a feature metric that quantitatively measures the importance of a feature as a chemical signature component, both feature magnitude and feature width need to be considered. To negate pedestal effects, the feature magnitude can be obtained by considering the magnitude difference between the local maximum and the local minimum. Referring to FIG. 33, there are two local minima, A at coordinates $(A_x, A_y)$ and C at coordinates $(C_x, C_y)$, one on either side of the local maximum, B at coordinates $(B_x, B_y)$, therefore two contributions to the feature metric are defined: a left-half feature metric (LHFM) 3302 and a right-half feature metric (RHFM) 3304.

To compute the LHFM 3302, $A_y$ and $B_y$ are first averaged to determine the y-axis point of a left-half midpoint, D. A left-half midpoint, D at coordinates $(D_x, D_y)$, is identified on the y-scale of the data curve toward the left side of the local maximum, B, and the x-axis point is noted. A left-half-height, $y_L$, is computed by the difference of $B_y$ and $D_y$. A left-half width, $x_L$, is computed by the difference of $D_x$ and $B_x$. The LHFM 3302 is computed as the product of the left-half-height, $y_L$, and the left-half-width, $x_L$, as alternatively represented by equation 10.

$$\text{LHFM} = y_L * x_L = (B_y - D_y) * (B_x - D_x) \quad \text{(Equation 10)}$$

Similarly, the RHFM 3304 is computed by first averaging $C_y$ and $B_y$ to determine the y-axis point of a right-half midpoint, E. The right-half midpoint, E at coordinates $(E_x, E_y)$, is identified on the y-scale of the data curve toward the right side of the local maximum, B, and the x-axis point is noted. A right-half-height, $y_R$, is computed by the difference of $B_y$ and $E_y$. A left-half width, $x_R$, is computed by the difference of $B_x$ and $C_x$. The RHFM 3304 is computed as the product of the right-half-height, $y_R$, and the right-half-width, $x_R$, as alternatively represented by equation 11.

$$\text{RHFM} = y_R * x_R = (B_y - E_y) * (E_x - B_x) \quad \text{(Equation 11)}$$

The feature metric (FM) is the sum of the two contributing half metrics: FM=LHFM+RHFM.

Chemical signature features can be identified as those features whose FM exceed a certain threshold. Noise features are assumed to have low FMs because they neither have the strength in terms of magnitude nor the width to compete with a chemical signature's stronger features. This assumption is based on the fact that the SINR is sufficiently high. Adjacent features that are identified as signature components can be grouped together forming a "feature-set." Several such feature-sets may be obtained based on the distribution of the signature features across the spectral range for a given spectral data. A "feature-mask" is defined as the support of the feature-sets of a given spectrum (i.e., the sample points corresponding to the feature-sets). A feature-mask includes all the feature-sets.

Figure 34:
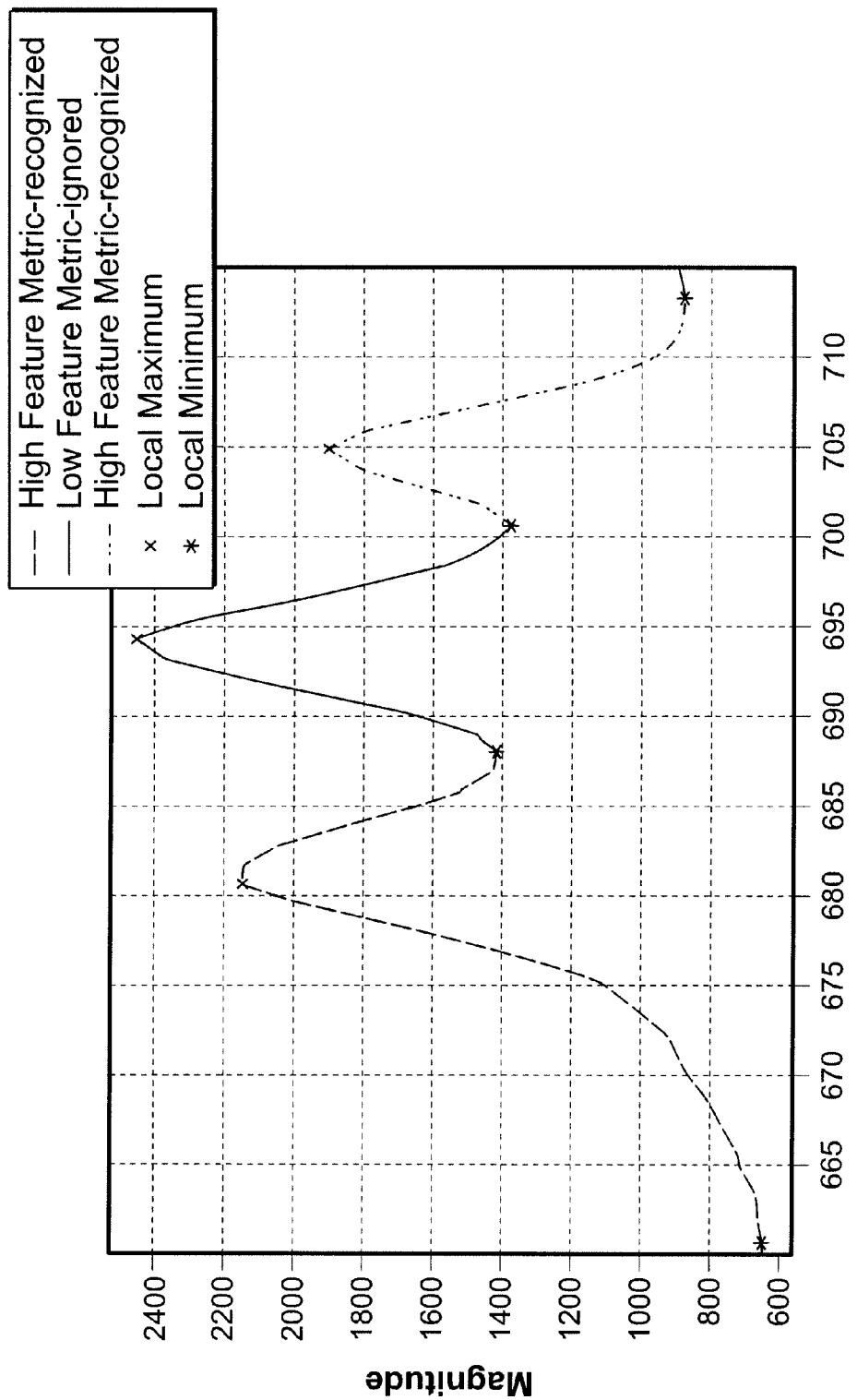
FIG. 34 is a plot of a data according to the feature metric technique that illustrates the problem of ignoring smaller features in a multiplet in accord with at least some aspects of the present concepts.

Referring to FIG. 34, in multiplets, however, the smaller features (e.g., feature B) that are enclosed by the larger features (e.g., features A and C) will have low FMs because of the low half-maximum magnitudes. Thresholding the FMs, consequently, may result in the outer larger features of the multiplet being designated as signature components and the inner smaller features being ignored. This problem of ignoring smaller features that belong to a multiplet is avoided by redefining feature-sets to include those ignored features that separate two feature-sets by a distance of at most two features. This allows recognition of multiplets up to a quadruplet.

The FM threshold must be either independent of the data or adapt to the data. All spectral data are normalized with respect to energy before the FMs are computed. The FMs corresponding to different spectral data, therefore, are standardized. But FMs are also a function of the SINR, which is not necessarily the same for each measurement. Computing the SINR involves knowing the signal, interference, and noise energy levels. Since such information is not available (operational assumption), there is no certainty that a particular chosen value of the FM threshold will be optimal for spectral data corresponding to different measurements (likely different SINR).

Figure 35A:
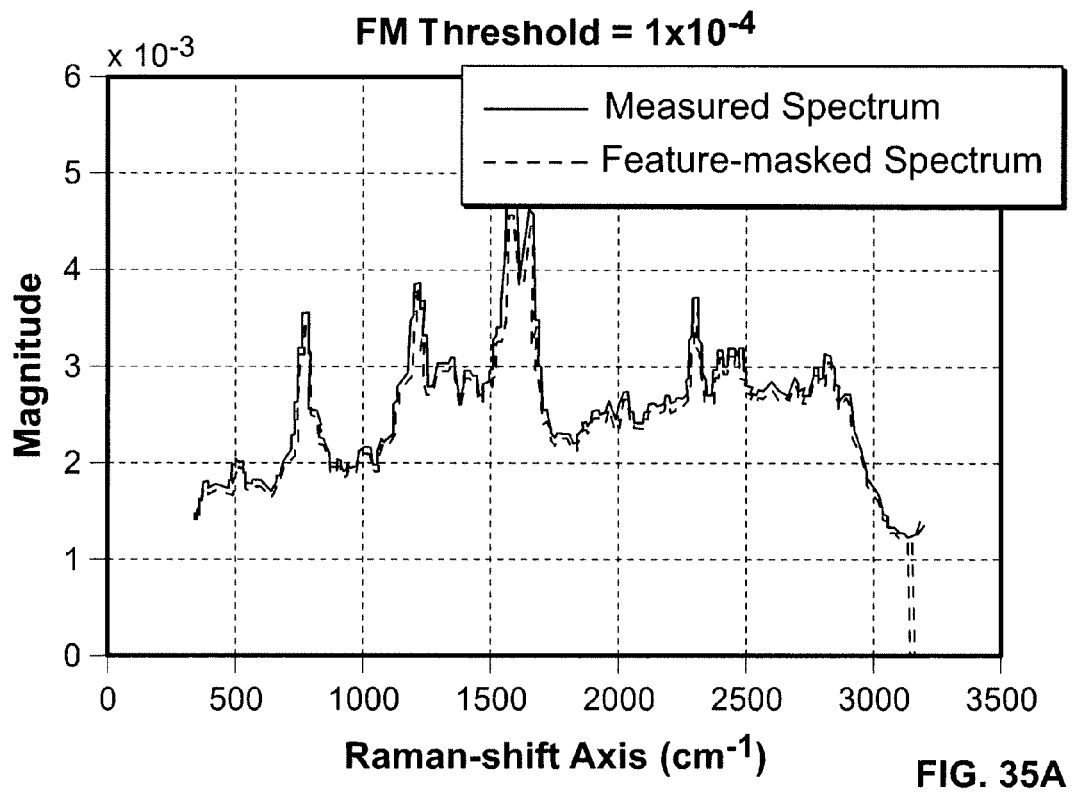
FIGS. 35A-D are plots of the effects of varying a feature metric threshold on a feature mask in accord with at least some aspects of the present concepts.
Figure 35B:
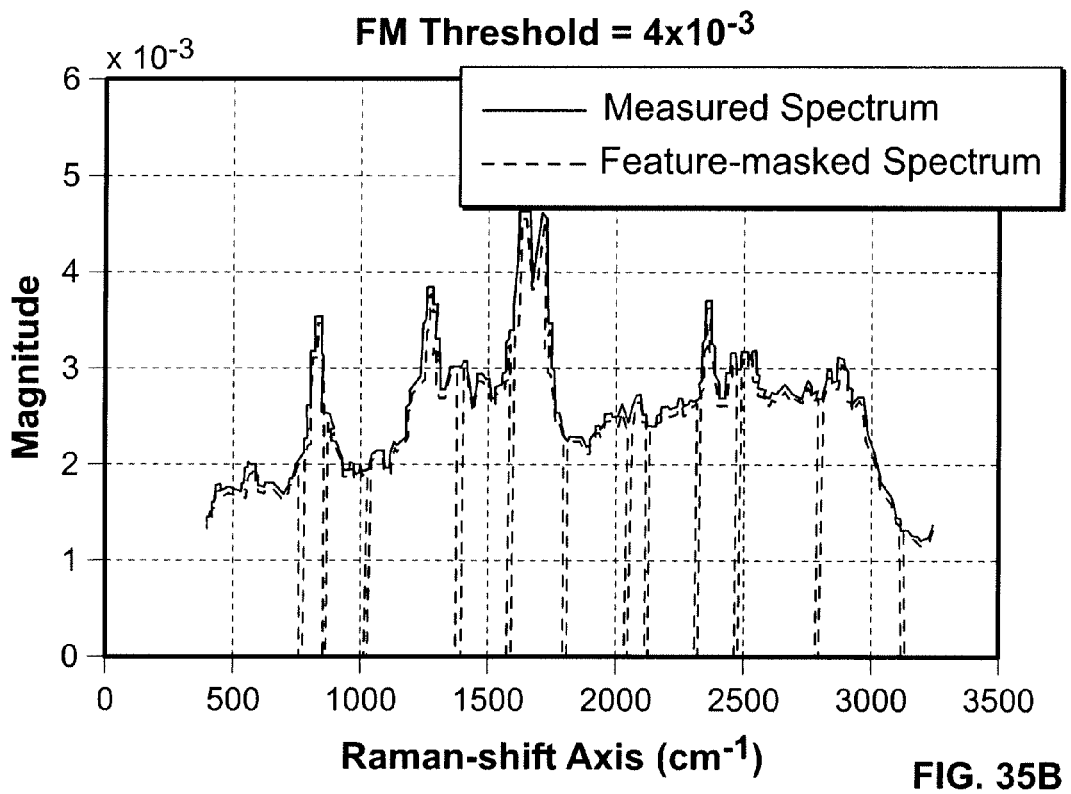
Figure 35C:
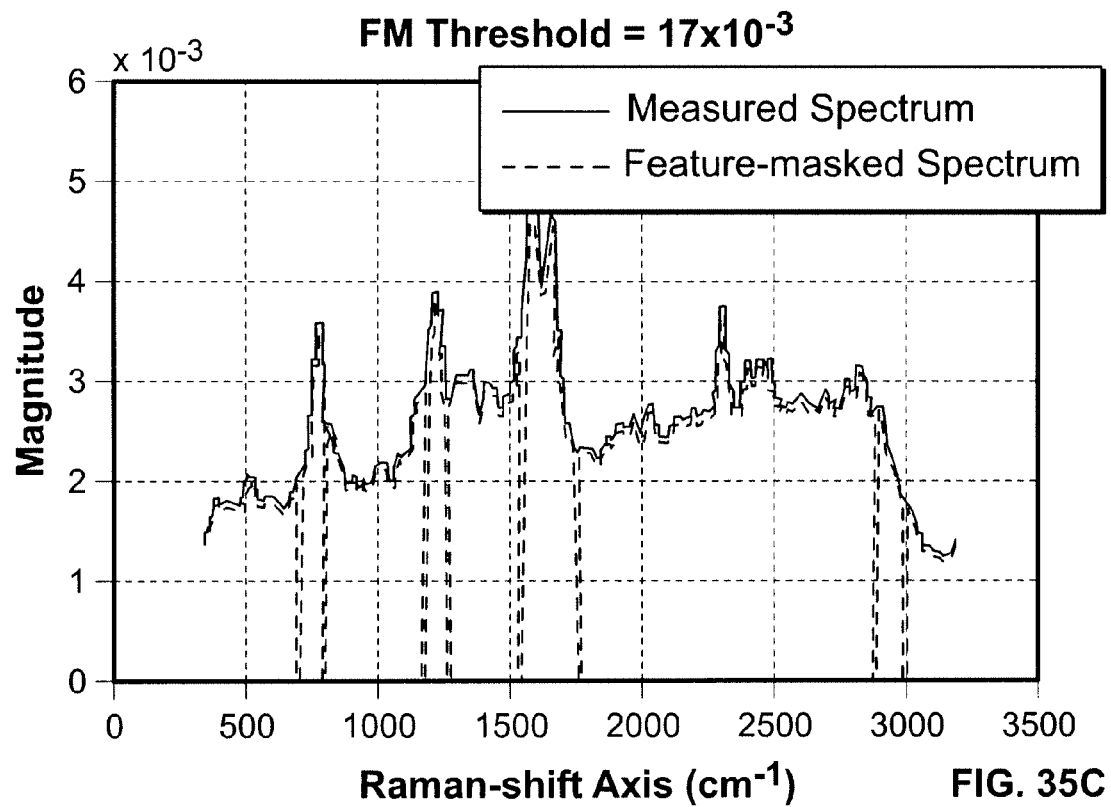
Figure 35D:
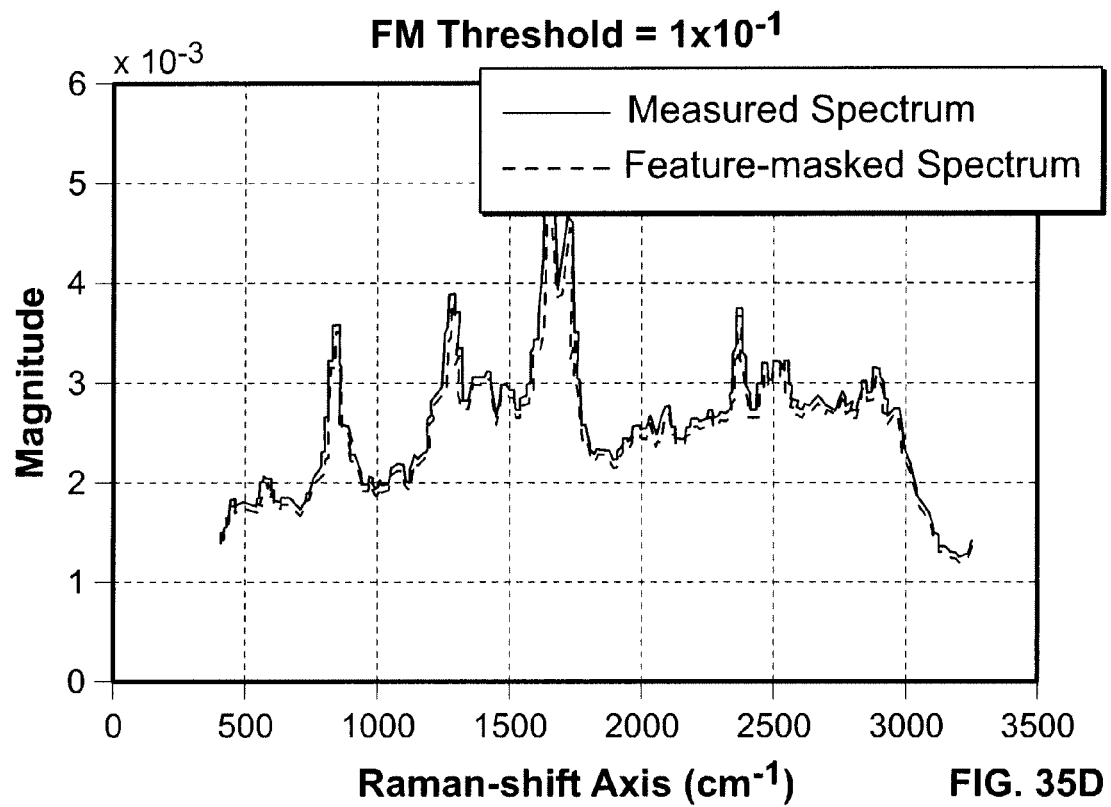
Figure 36A:
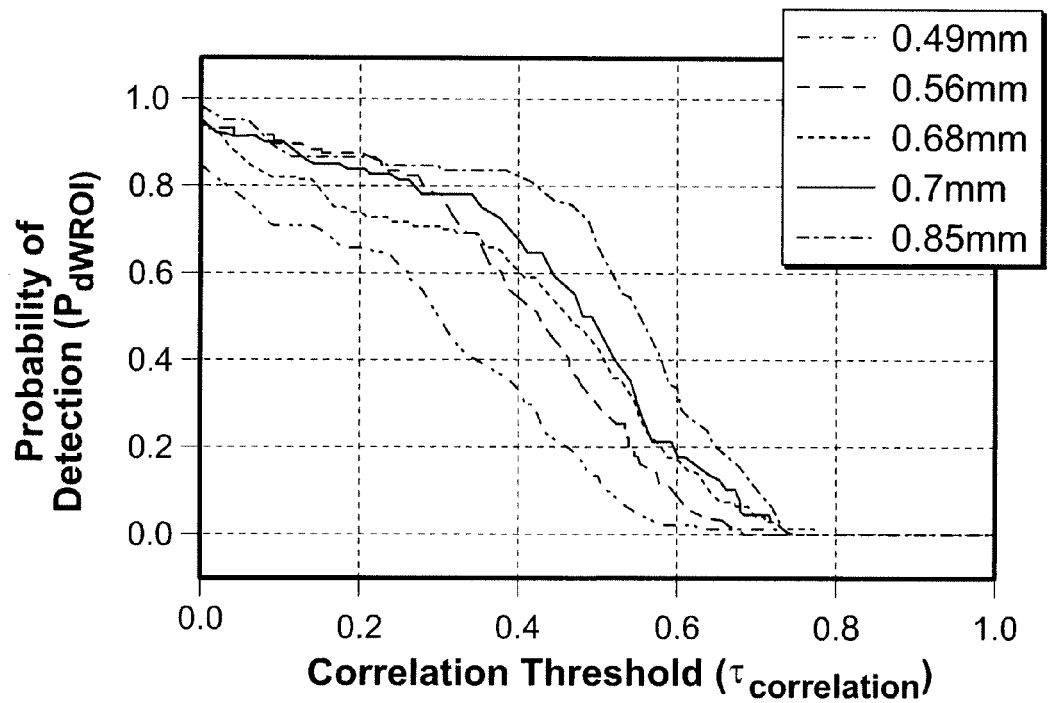
FIGS. 36A-D are plots of the feature metric algorithm (FMA) performance results for TMe-S-on-glass data with N=1 in accord with at least some aspects of the present concepts.
Figure 36B:
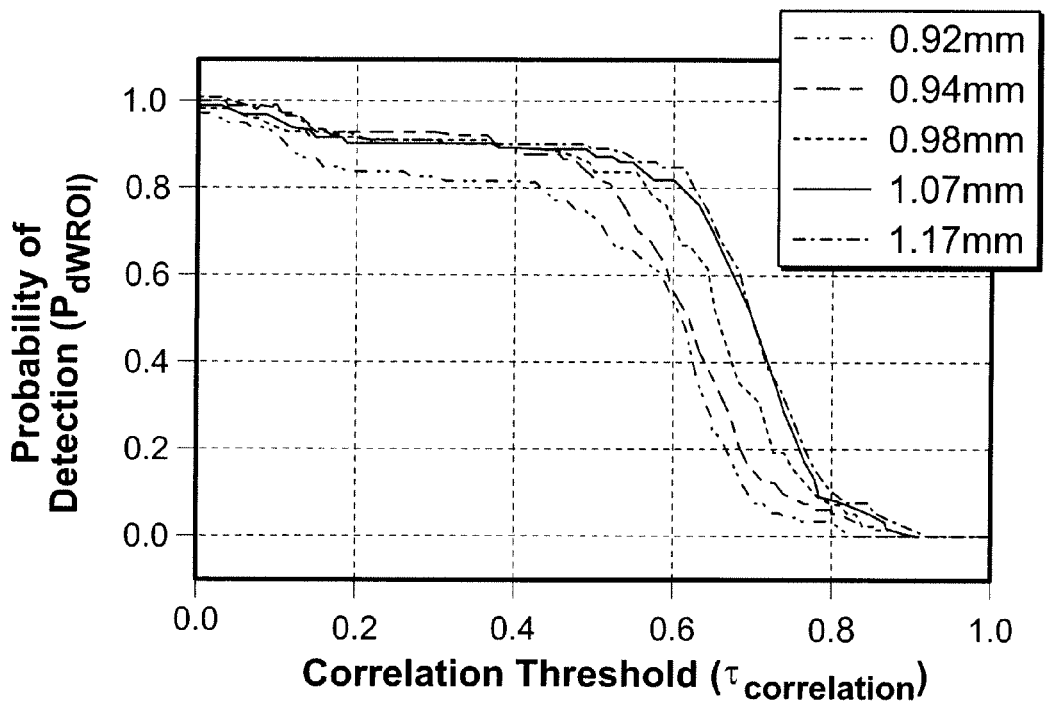
Figure 36C:
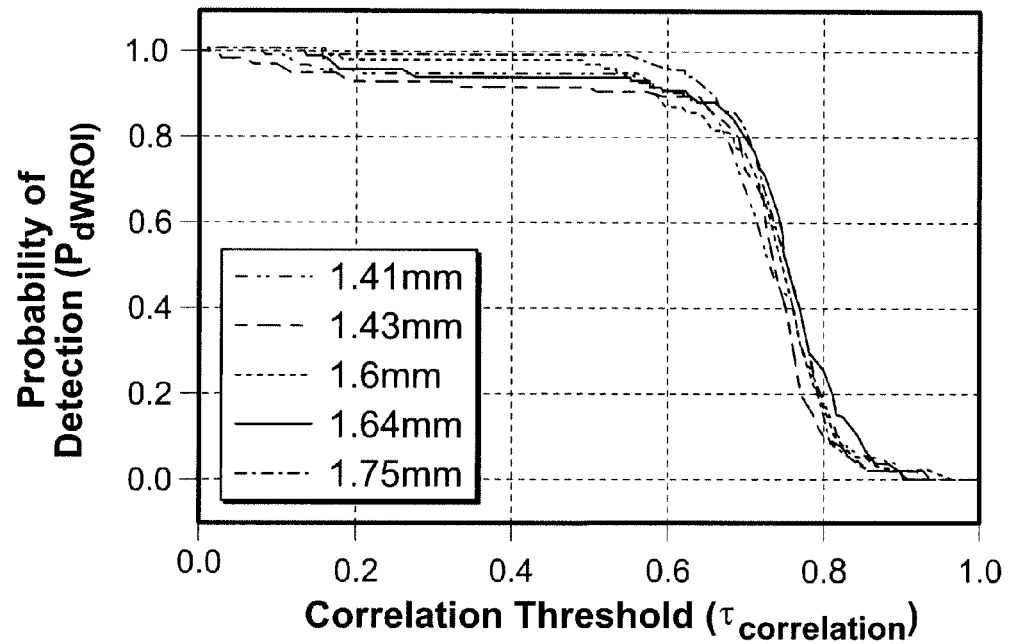
Figure 36D:
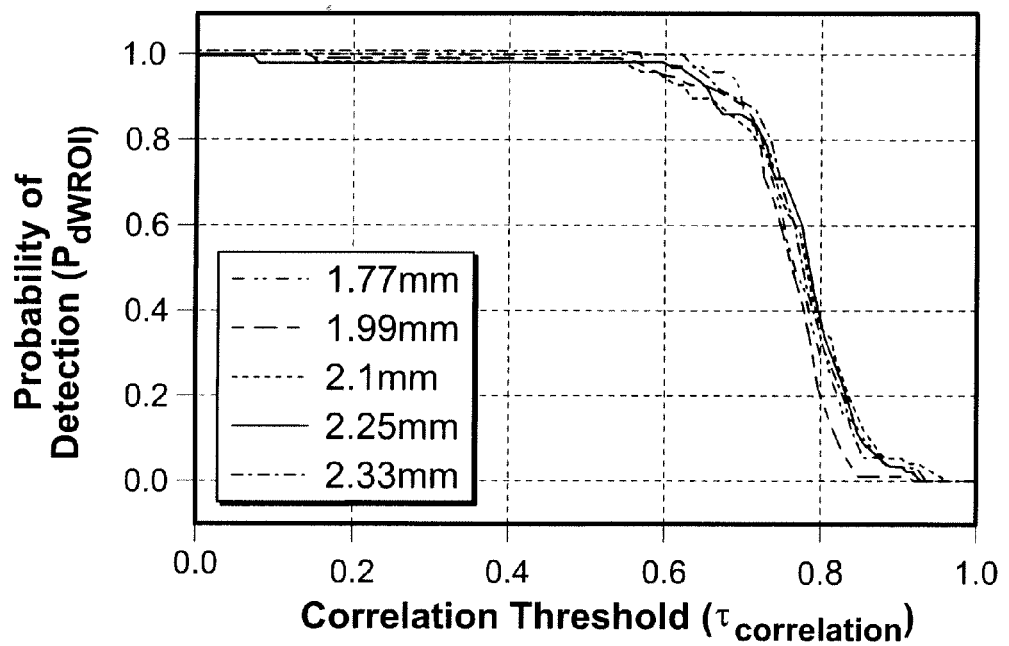
Figure 37A:
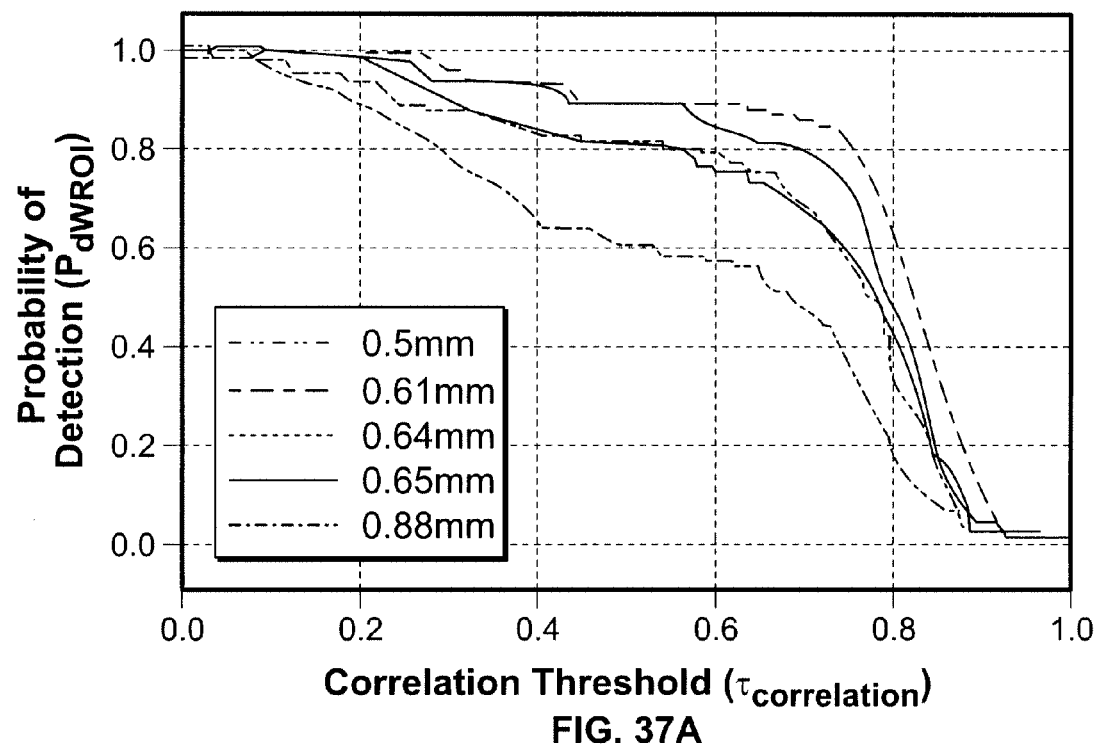
FIGS. 37A-C are plots of the FMA performance results for TMe-S-on-gravel data with N=1 in accord with at least some aspects of the present concepts.
Figure 37B:
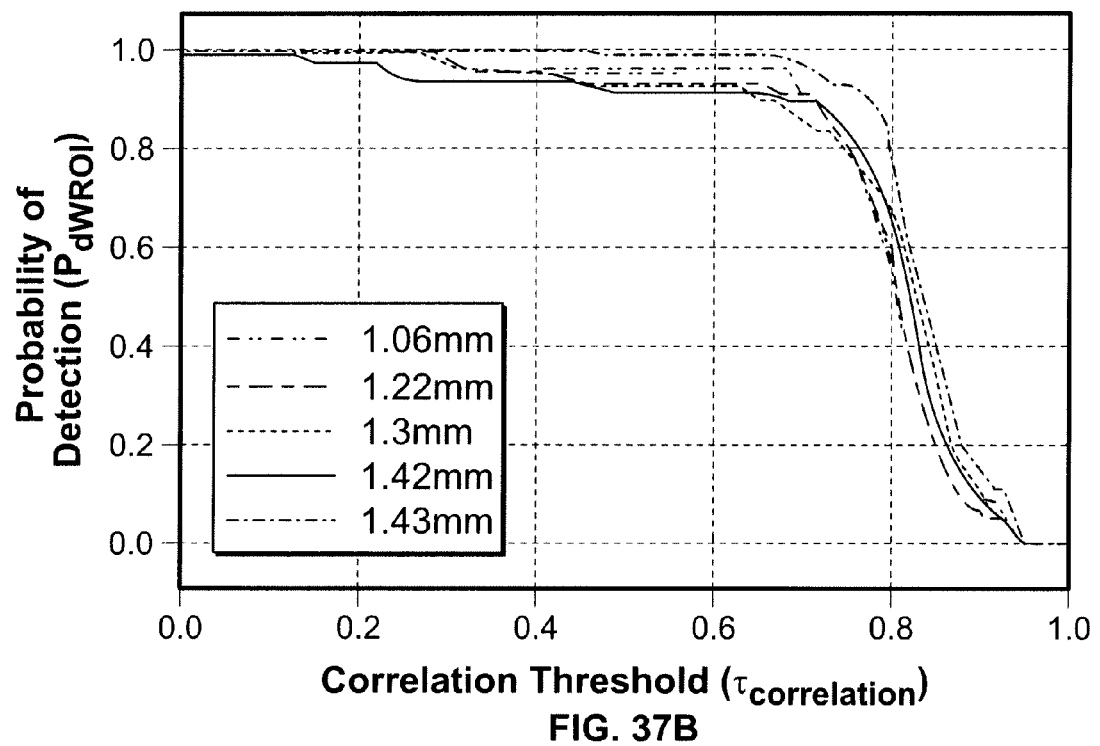
Figure 37C:
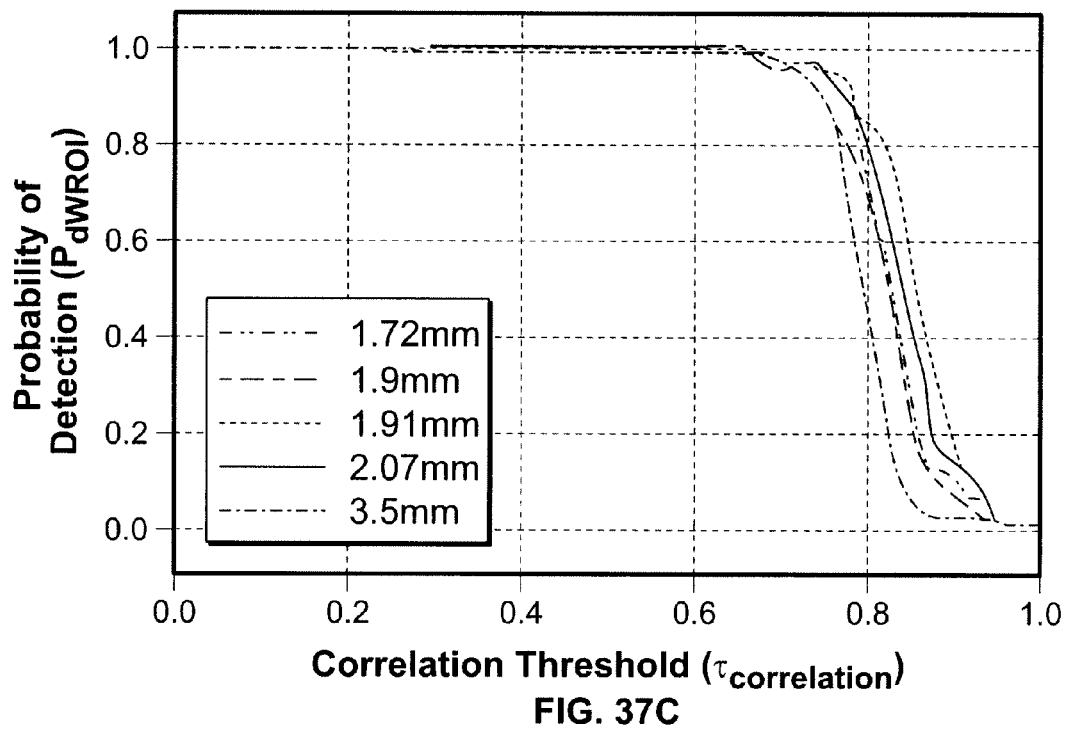
Figure 38A:
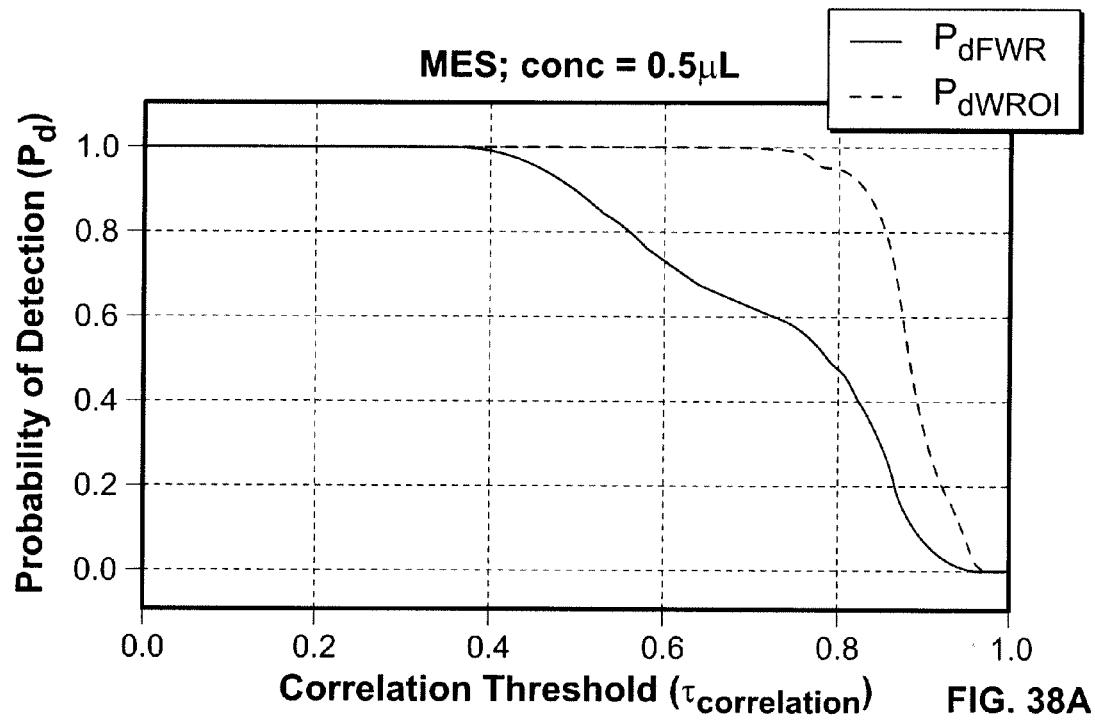
FIGS. 38A-D are plots of the FMA performance results for MES data with N=1 in accord with at least some aspects of the present concepts.
Figure 38B:
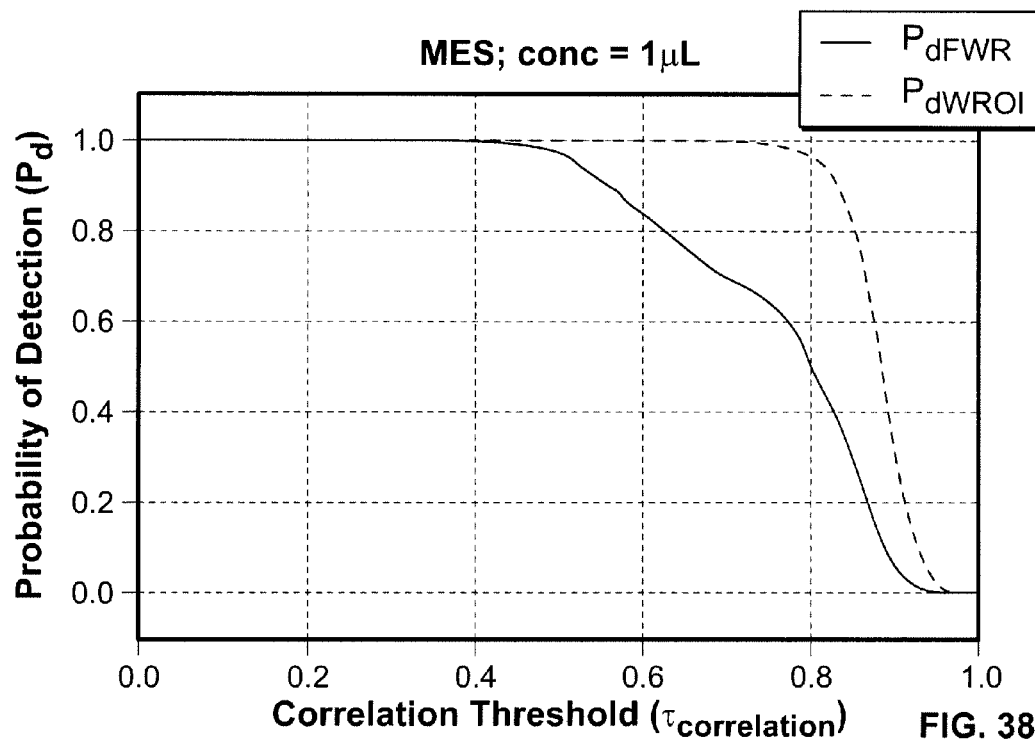
Figure 38C:
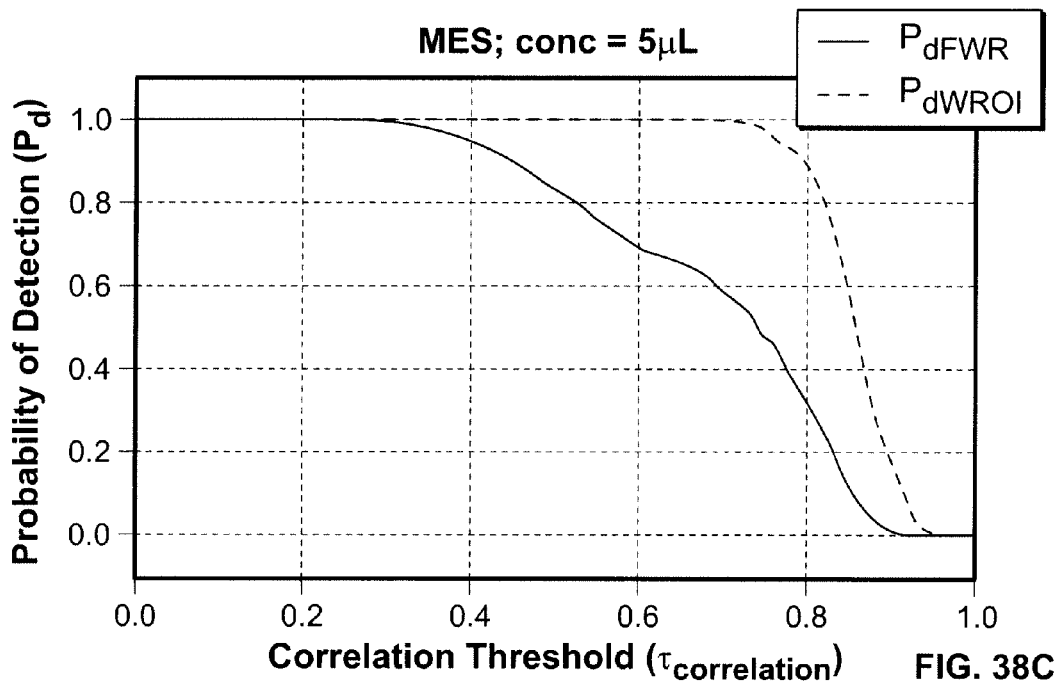
Figure 38D:
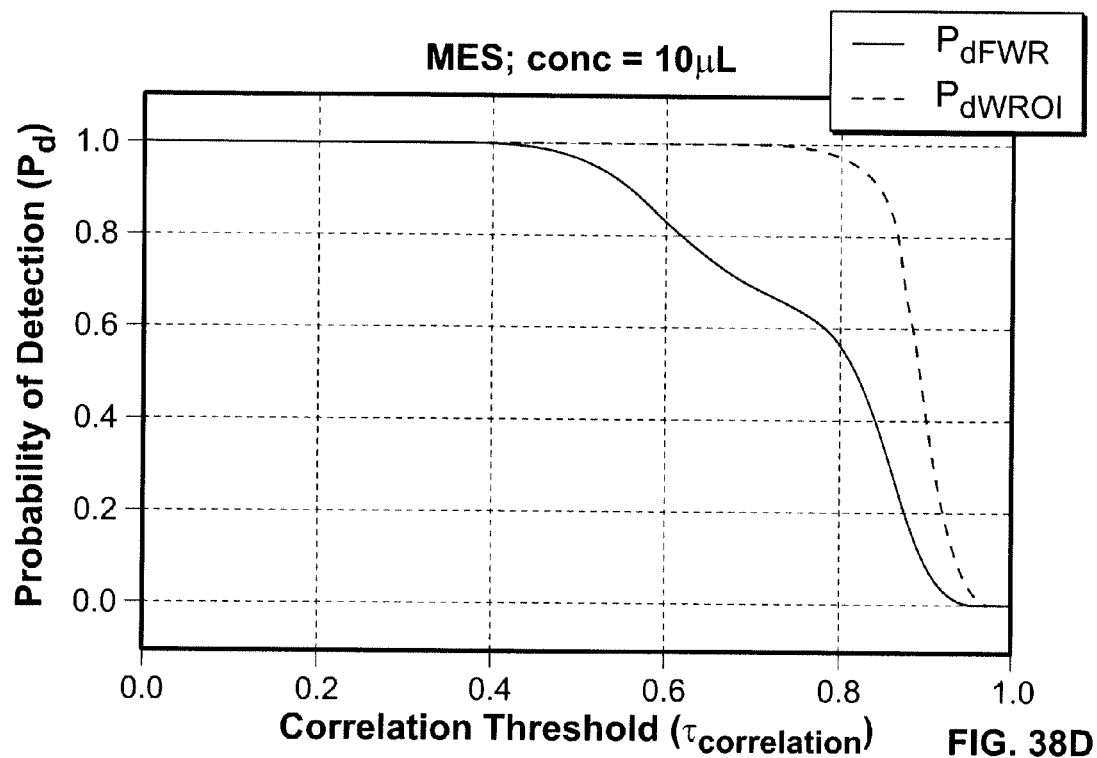
Figure 39A:
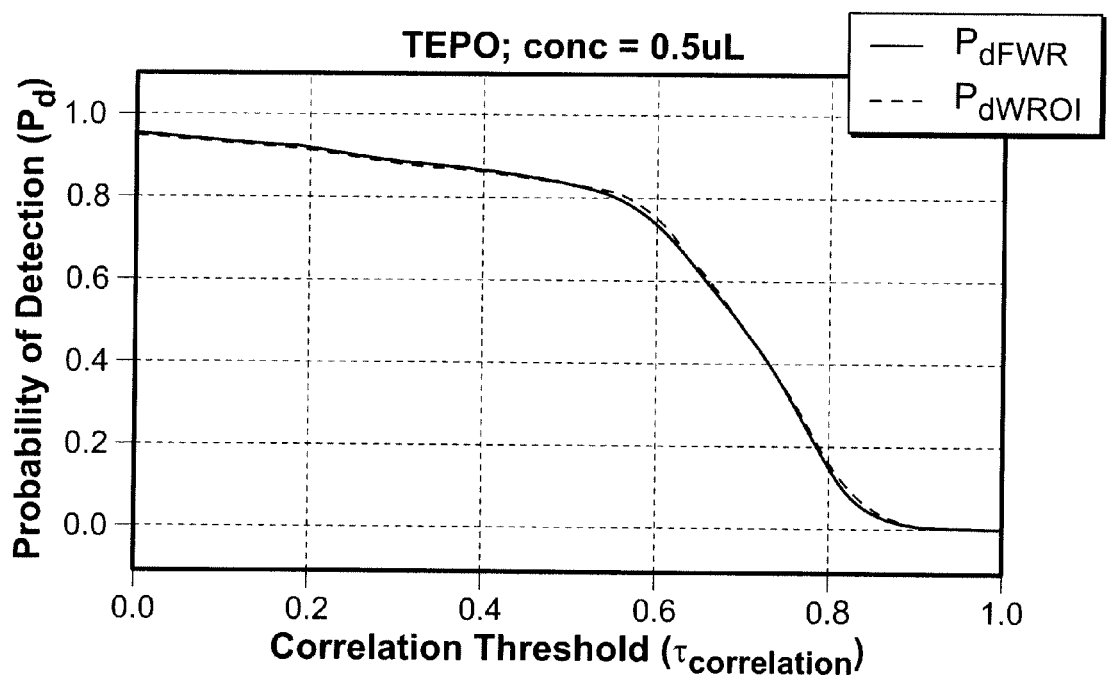
FIGS. 39A-D are plots of the FMA performance results for TEPO data with N=1 in accord with at least some aspects of the present concepts.
Figure 39B:
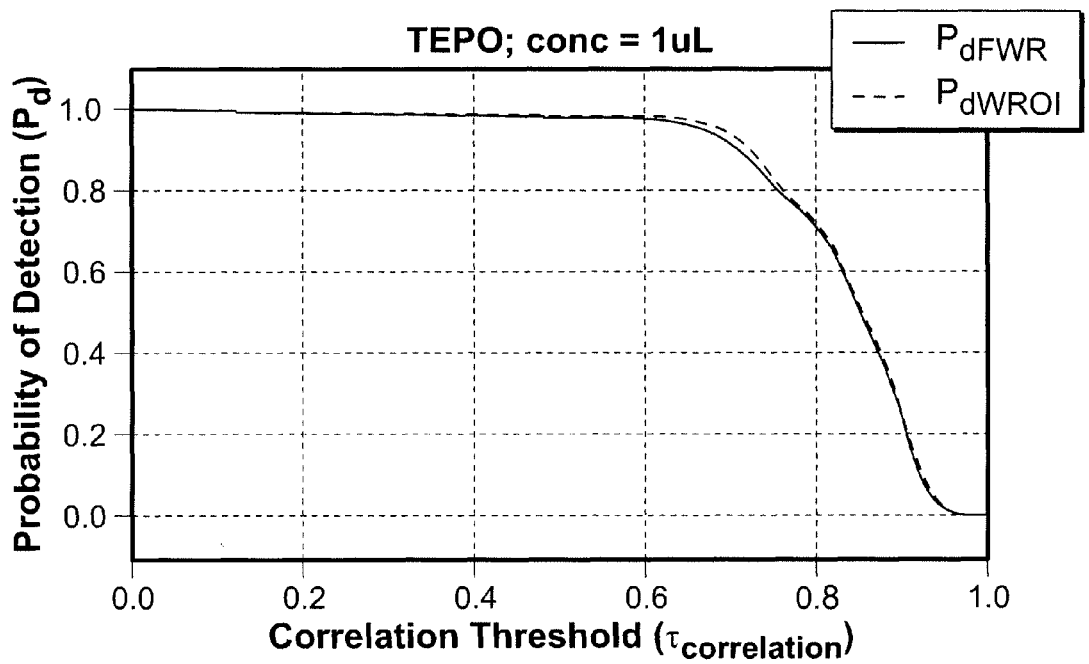
Figure 39C:
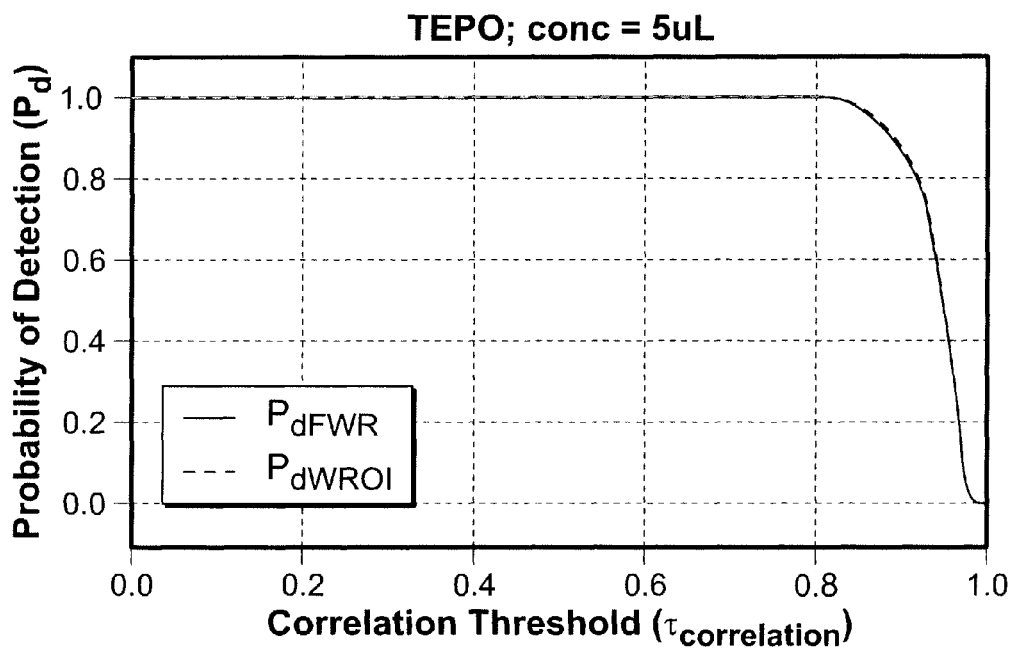
Figure 39D:
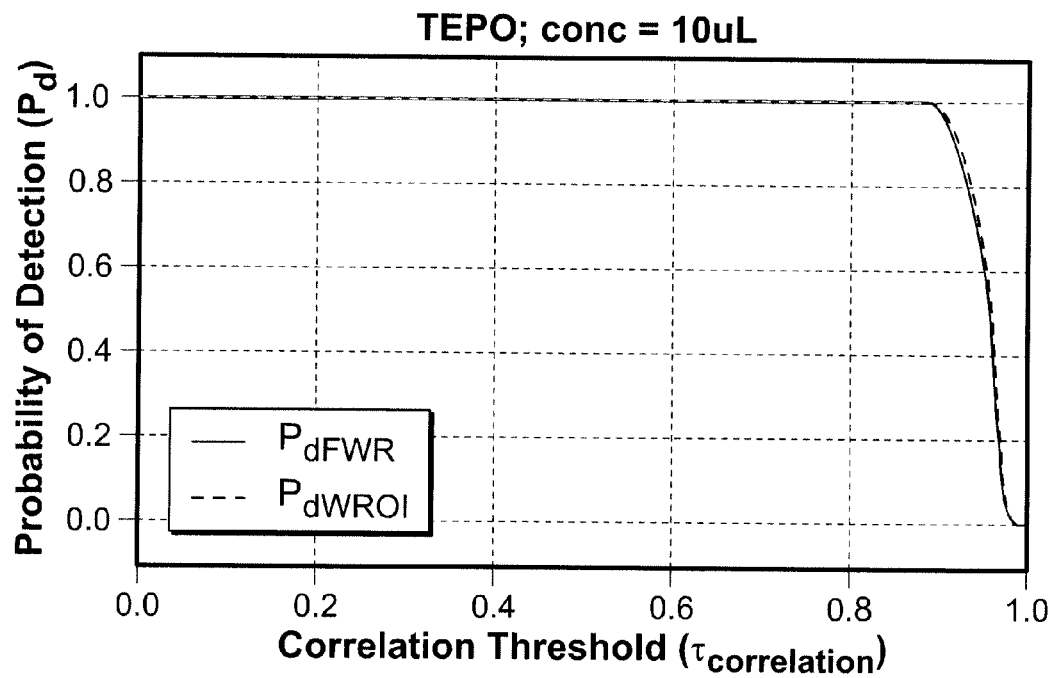
Figure 40A:
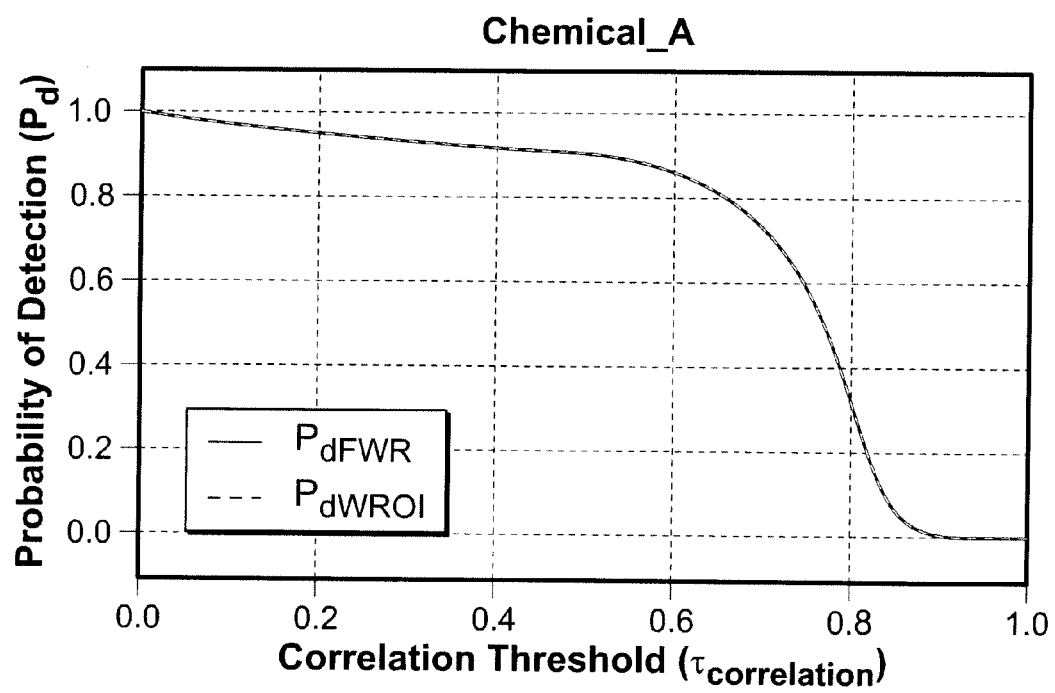
FIGS. 40A-D are plots of the FMA performance results for Dataset 4 with N=1 in accord with at least some aspects of the present concepts.
Figure 40B:
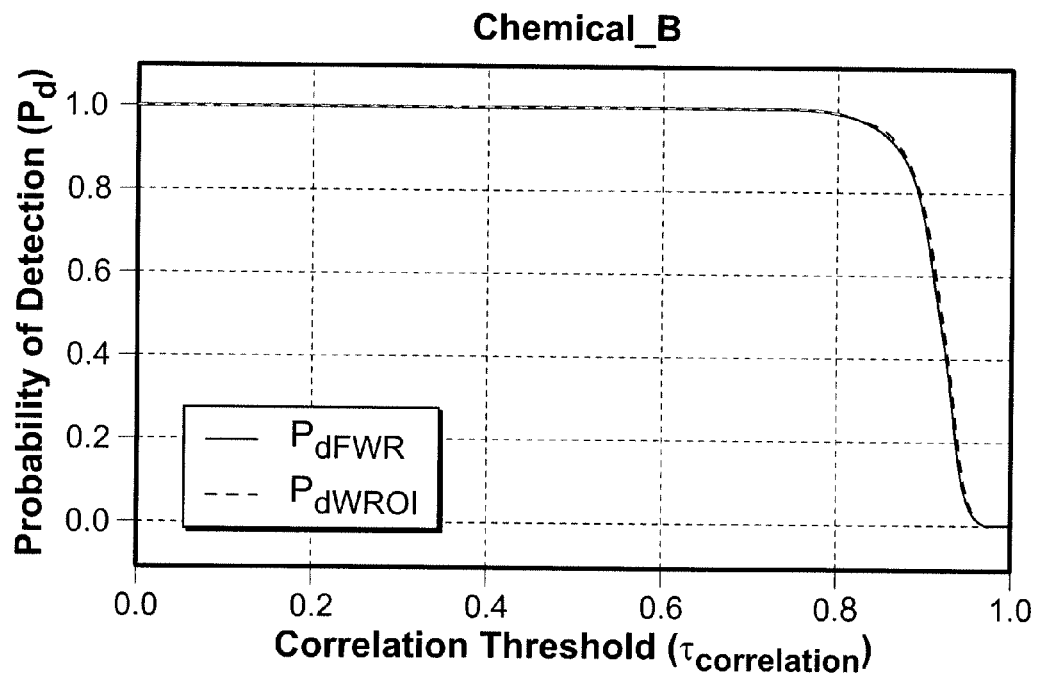
Figure 40C:
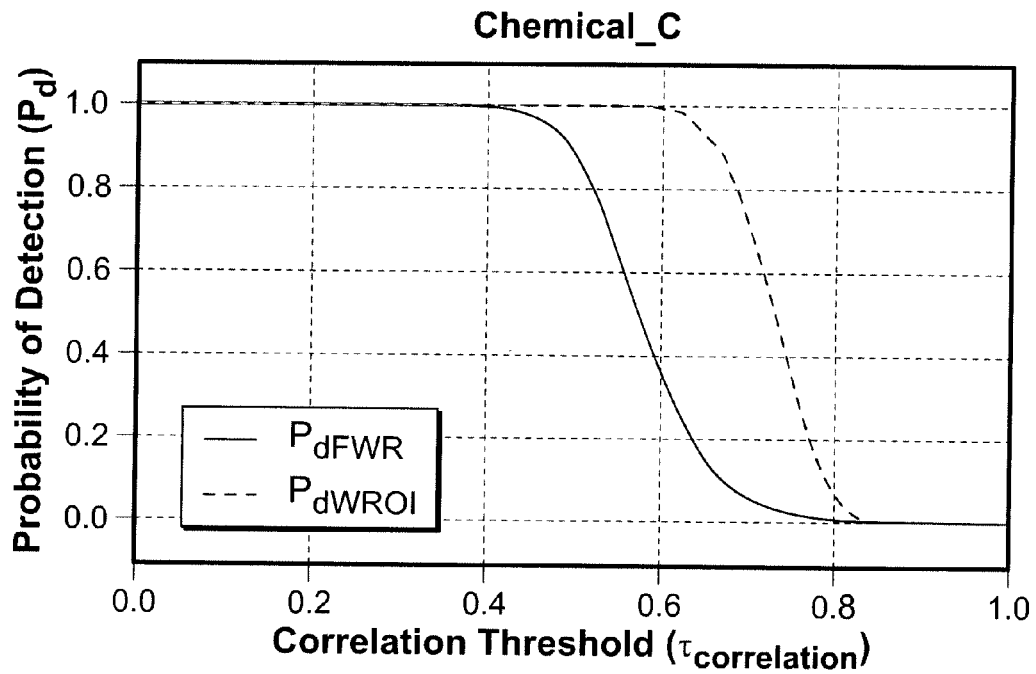
Figure 40D:
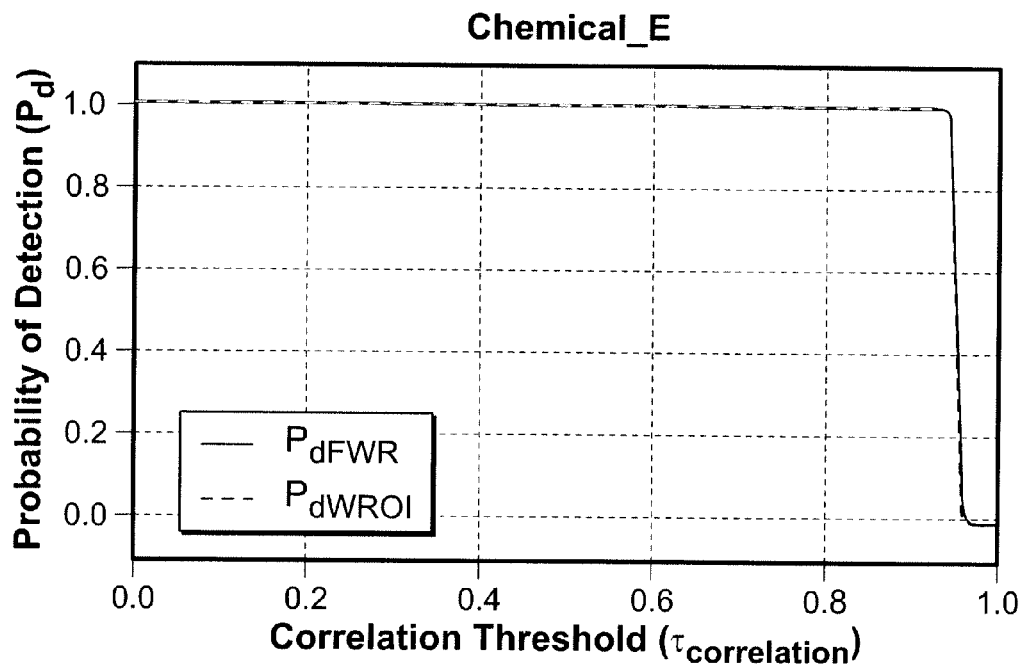
Figure 41A:
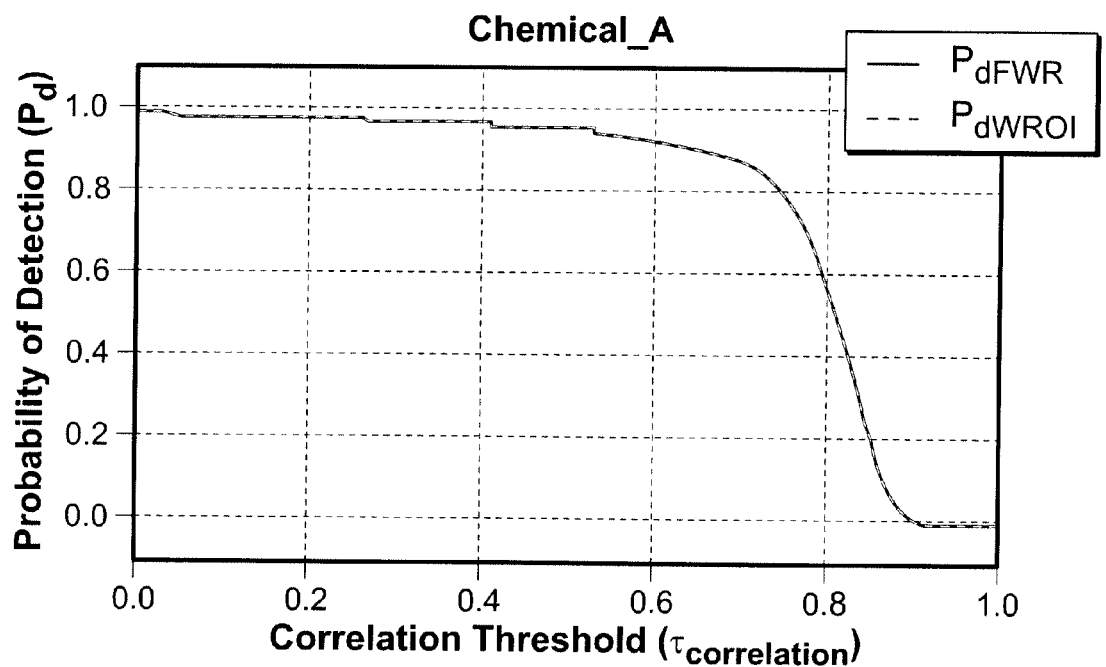
FIGS. 41A-D are plots of the FMA performance results for Dataset 5 with N=1 in accord with at least some aspects of the present concepts.
Figure 41B:
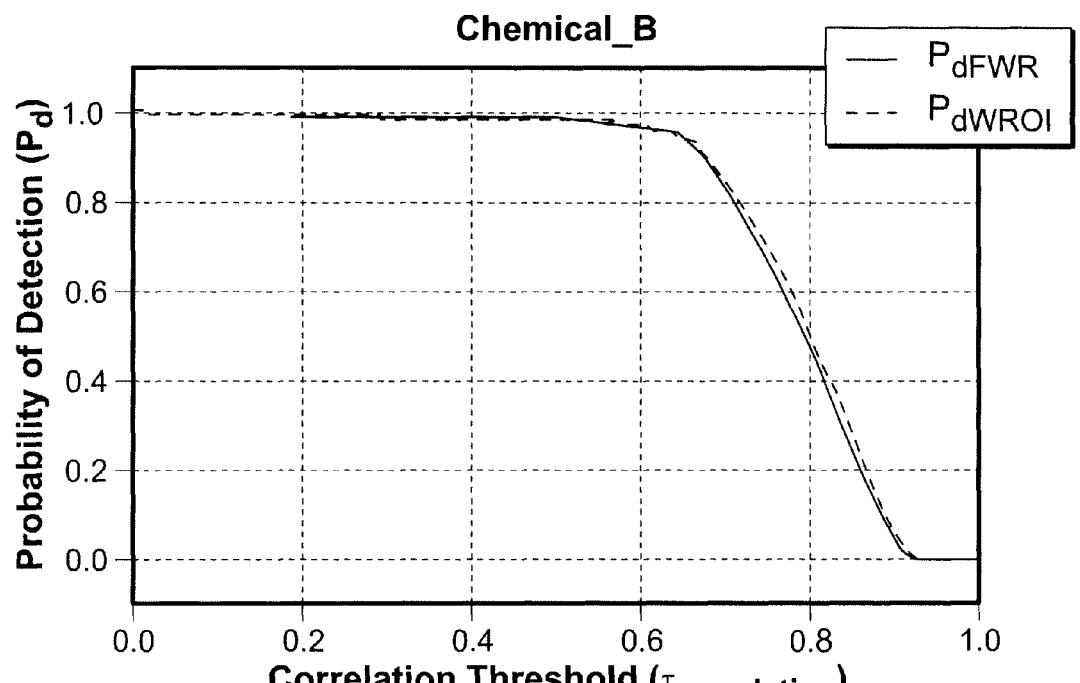
Figure 41C:
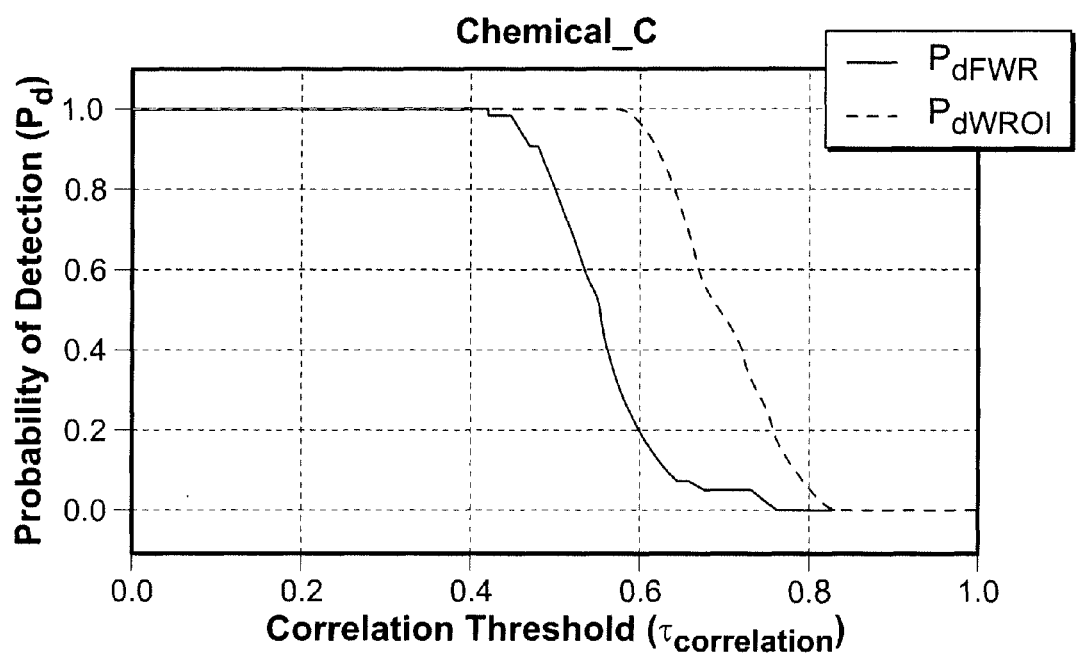
Figure 41D:
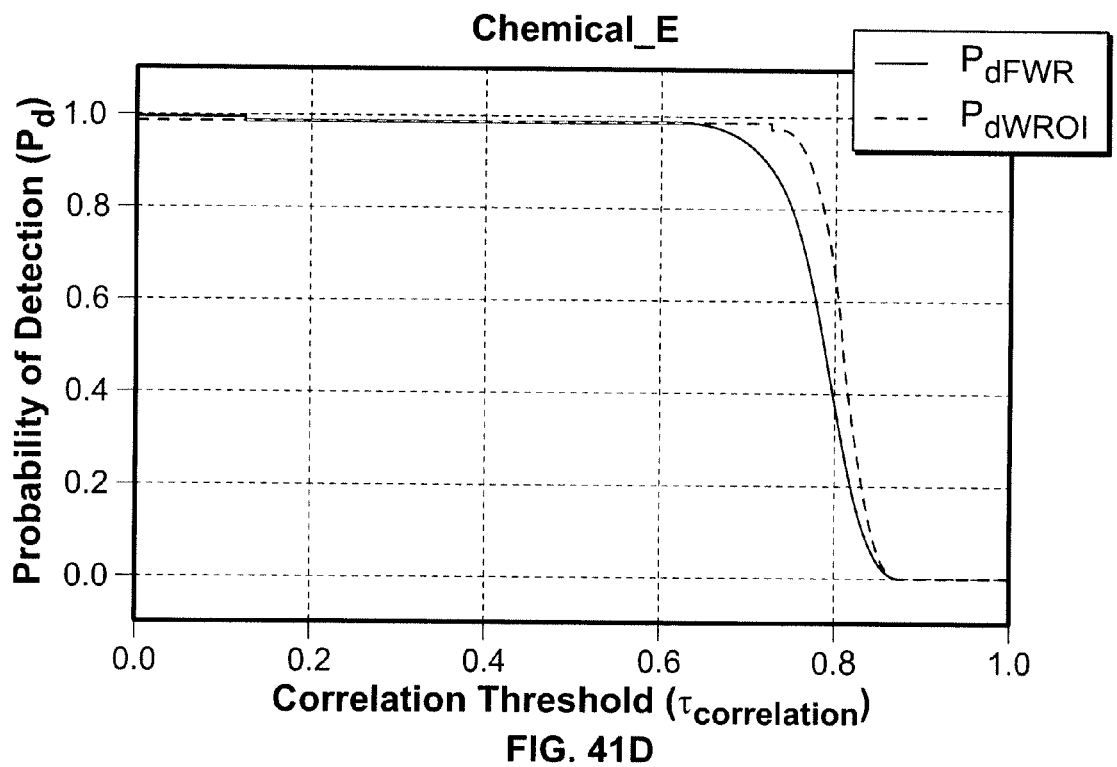
Figure 42A:
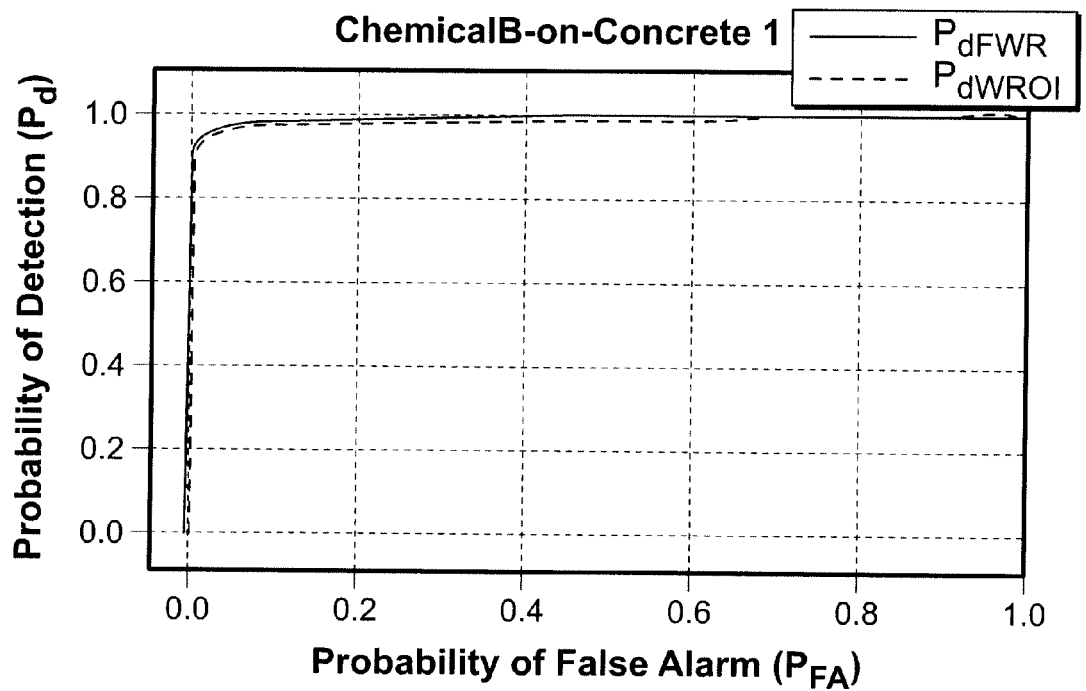
FIGS. 42A-D are plots of the FMA performance results for Dataset 6 with N=1 in accord with at least some aspects of the present concepts.
Figure 42B:
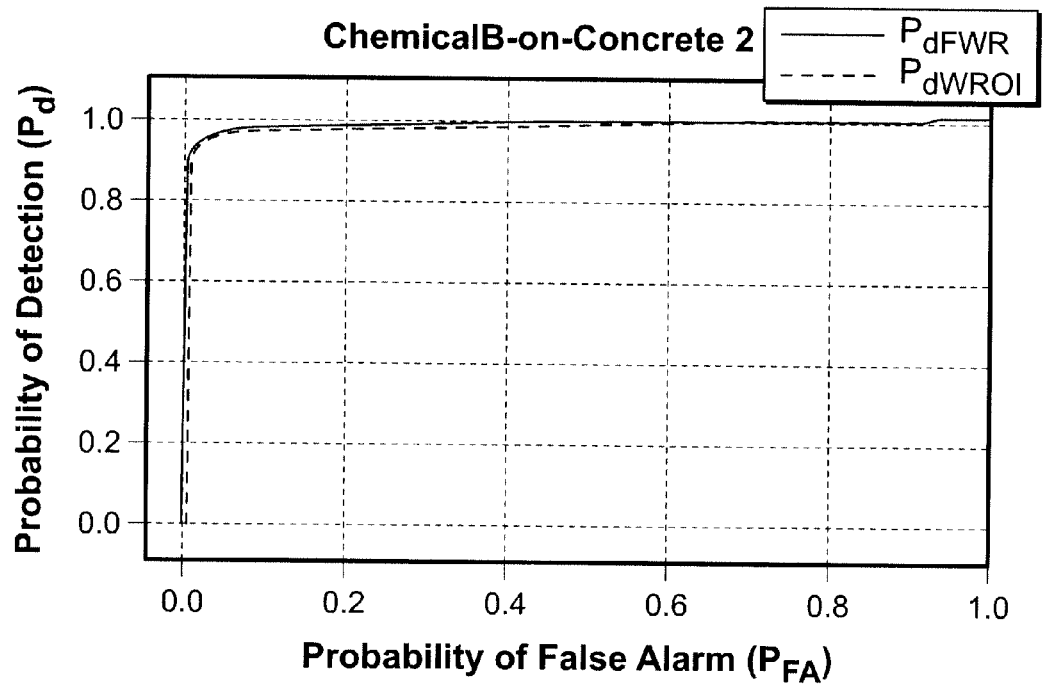
Figure 42C:
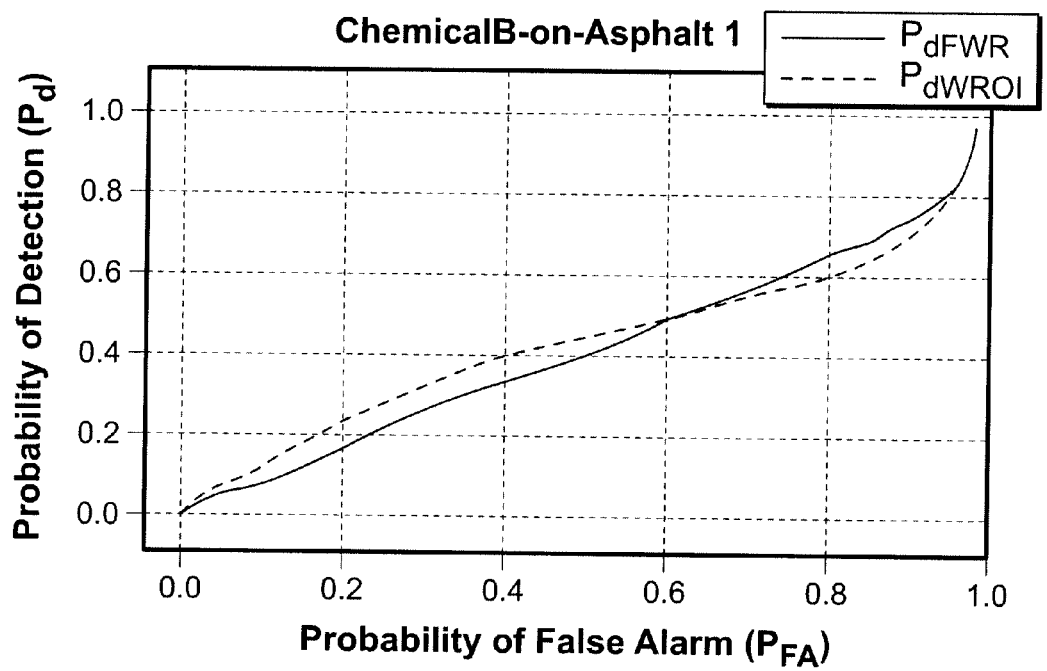
Figure 42D:
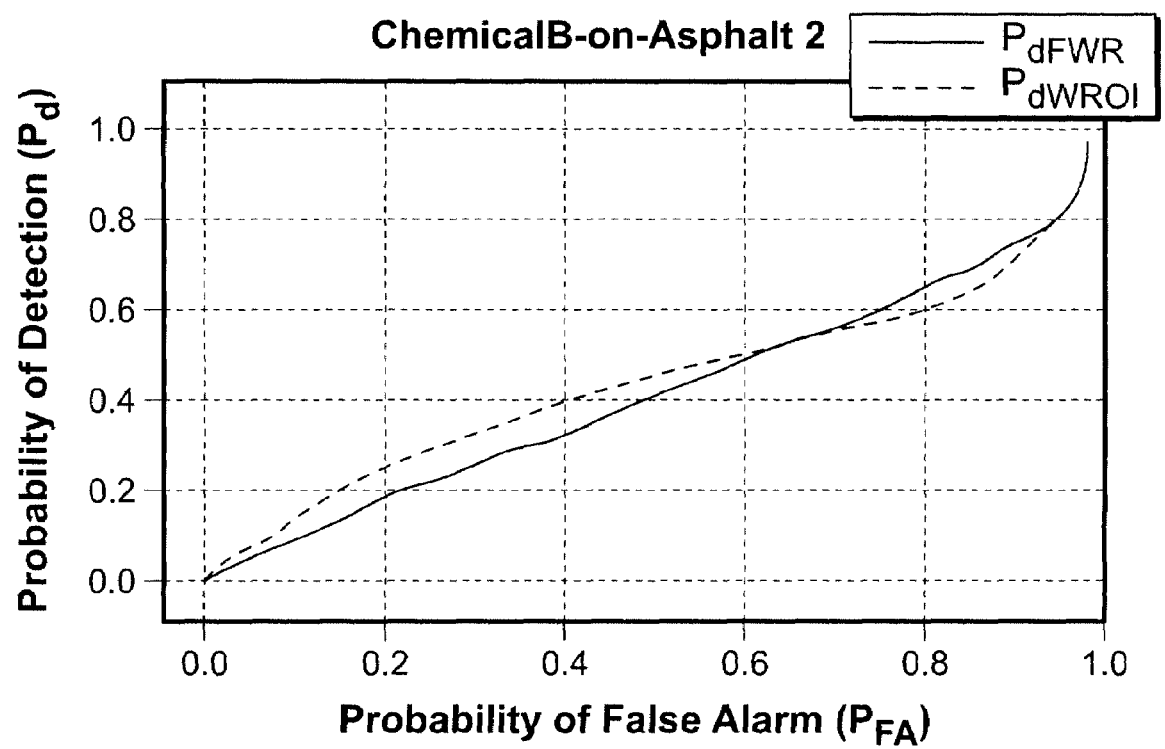

In general, however, a very low FM threshold will result in a feature-mask with only one feature-set. Thus, referring to FIG. 35A, all features will be selected because all FMs will exceed the threshold where the measured spectrum is shown as a solid line and the spectrum obtained by masking via the feature-mask is shown by a dashed line. Referring to FIG. 35B, increasing the FM threshold to a certain extent from this low value will result in a feature-mask with multiple feature-sets because chemical signature features that are generally distributed across the wavenumber axis will be supported due to their high FMs, while the features in between (noise) will be ignored due to their low FMs (assuming high SINR). Referring to FIG. 35C, increasing the FM threshold further will reduce the number of features-sets in the feature-mask because FMs of fewer signature features will exceed the FM threshold. Finally, referring to FIG. 35D, if the FM threshold is set too high, then the feature-mask will be a zero data vector as a result of no FMs exceeding the threshold.

An FM threshold, nonetheless, should be so chosen such that no chemical signature features are ignored even at the cost of supporting noise features. Using this as a guiding principle, an ad-hoc method of choosing the FM threshold has been developed. Broadly speaking, the number of feature-sets in a feature-mask of a given spectrum is a quantitative measure of whether all chemical signature features have been supported by the mask. The FM threshold can be increased, starting from a low value, till a feature-mask with a preset number of feature-sets is obtained. This preset number may be chosen by considering the number of feature-sets required to support the library spectrum. However, due to the availability of many library spectra, each supported by a different number of feature-sets, some trial and error had to be performed to optimize this parameter. The purpose of the trial and error was to obtain a value for the preset number of feature-sets such that it is independent of the chemical signature contained in the spectrum. Currently, the chosen preset number of feature-sets is 6.

Increasing the FM threshold does not always guarantee obtaining the preset number of feature-sets owing to several reasons—low SINR, and/or large FM threshold increment step-size, and/or fewer than the preset feature-sets supporting the chemical library, etc. In such scenarios, increasing the FM threshold decreases the number of feature-sets, indicating that some signature features have been ignored. In order to avoid ignoring valid signature features, the feature mask obtained at the previous run is chosen.

The pedestal is estimated and subtracted in each feature-set of the feature-mask. A simple comparison between two estimates is made and the minimum of the two is chosen as the pedestal estimate in that feature-set. The two pedestal estimates are obtained by: (a) LIPE (i.e., linearly connecting all the local minima in the feature set) and (b) linearly connecting the first and the last sample points in the feature-set. The pedestal estimate is chosen as the minimum of the two estimates in order to avoid the peak attenuation problem described above and in particular, with respect to FIG. 9.

The algorithm for processing spectral data via FM thresholding comprises, first, smoothing the spectral data via a LP filter such as, for example, the LP filter described above with respect to equation 7. The algorithm includes, secondly, interpolating the data at the wavenumbers corresponding to the library spectrum to match the spectral non-linearities. Third, correcting the IRC as described above. Fourth, replacing all negative values with zero. Fifth, normalizing the data with respect to energy. Sixth, identifying features via adapting the FM threshold and building the feature-mask. Seventh, estimating and subtracting pedestals in each feature-set. Eighth, truncating interfering peaks. Ninth, correlating with similarly processed library spectrum. One of ordinary skill in the art will appreciate that some of these steps may be performed in a different order than described above.

The feature-metric algorithm (FMA) processes Raman-shift data by treating it as a series of connected features. A feature-metric quantifies features for their chemical signature contribution. The feature-metrics are thresholded and a smaller set of features is identified. The pedestal is estimated and subtracted in only this smaller set. This achieves faster processing as compared to SWTPE.

The FM algorithm (FMA) satisfies a need for single spectrum processing. The FMA performance results for five datasets with N=1 are presented as plots of probabilities of detection, $P_d$, versus the correlation threshold, $\tau_{correlation}$, for Datasets 2-5, and $P_d$ versus probability of false alarm, $P_{fa}$, for Dataset 6. These probabilities are computed as described above with $\tau_{correlation}=0.7$. Further, the FWR and the WROI ranges of the seven chemicals mentioned above are used here.

The FM algorithm uses two parameters—the difference threshold and the minimum number of feature-sets in a feature-mask. These parameters are set to $1\times10^{-3}$ and 6, respectively, in the FMA for all datasets as mentioned in section V.E.

FIGS. 36A-D and 37A-D show the $P_{dWROI}$ versus $\tau_{correlation}$ for TMeS-on-glass and TMeS-on-gravel data, respectively. It is seen that the FMA yields $P_{dWROI}\approx0.8$ at $\tau_{correlation}=0.7$ for drop-diameters $\geq1.41$ mm in the case of glass background, and for drop-diameters $\geq0.88$ mm in the case of gravel background. In general, smaller drop-diameters are difficult to detect and more so on glass background. These plots demonstrate the dependence of the Raman scattered light's strength on chemical concentration: for a given $\tau_{correlation}$, the higher the concentration the higher the $P_{dWROI}$. The FMA corroborates the surprising result obtained via SWTPE that TMeS is easier to detect on gravel than on glass.

FIGS. 38A-D and 39A-D show the $P_d$ versus $\tau_{correlation}$ curves for the four concentrations (0.5, 1, 5, 10 μL) of MES and TEPO, respectively. It can be seen that $P_{dWROI}\approx1$ at $\tau_{correlation}=0.7$ for all concentrations of MES. On the other hand, only the two higher concentrations of TEPO (5 μL and 10 μL) yield $P_{dWROI}\approx1$ at $\tau_{correlation}=0.7$. For a concentration of 1 μL, $P_{dWROI}$ is sufficiently high ($\approx0.96$) at $\tau_{correlation}=0.7$. The lowest concentration of TEPO, however, yields $P_{dWROI}$ 0.5 at $\tau_{correlation}=0.7$. Using an increased $\tau_{correlation}$ of 0.8 does not significantly decrease $P_{dWROI}$, however, for higher concentrations of either chemical.

FIGS. 40A-D show the FMA performance result for the four chemicals of Dataset 4 (i.e., chemicals A, B, C, and E). It is seen that Chemical_B and Chemical_E yield $P_{dWROI}=1$ at $\tau_{correlation}=0.7$. Chemical_A and Chemical_C, however, are not as easily detected, i.e., $P_{dWROI}\approx0.7$ at $\tau_{correlation}=0.7$. Chemical_C, which is the same as TMeS or MES, surprisingly yields a lower $P_{dWROI}$ than for TMeS or MES at $\tau_{correlation}=0.7$. This surprising result is due to comparable magnitudes of noise and chemical signature features in the Chemical_C data.

FIGS. 41A-D show the FMA performance when the above four chemicals are placed on a concrete background. It is seen that all chemicals, except Chemical_C, yield $P_{dWROI}\geq0.8$ at $\tau_{correlation}=0.7$. In fact, Chemical_E yields a high detection probability: $P_{dWROI}\approx0.98$ at $\tau_{correlation}=0.7$. Chemical_A, whose neat data in Dataset 4 yields $P_{dWROI}\approx0.7$ at $\tau_{correlation}=0.7$, shows $P_{dWROI}>0.8$ at the same threshold. Chemical_C yields a low $P_{dWROI}\approx0.5$ at $\tau_{correlation}=0.7$, however, as compared to its neat data in Dataset 4 that yields $P_{dWROI}\approx0.7$ at the same threshold. Neat data refers to data that does not have any background interferences.

FIGS. 42A-D show the ROC curves of Chemical_B on concrete and asphalt. It is seen that $P_{dWROI}>0.95$ for $P_{fa}=0.02$ for both files of Chemical_B-on-concrete. The ROC curves corresponding to Chemical_B-on-asphalt, which does not contain Chemical_B spectra because of its reaction with asphalt, show that the FMA rejects these non-chemical spectra just as well. These ROC curves are much better than the ones obtained via SWTPE in that the FMA's $P_d$ is higher for lower $P_{fa}$ values than those obtained via SWTPE for Chemical_B-on-concrete data.

The motivation for FMA came from the practical need for a fast technique to process a single spectrum. It was important that in achieving higher processing speeds, however, the detection performance should not be compromised. Tables 2-4 show the detection rates obtained via SWTPE and FMA for $\tau_{correlation}$=0.7 for Dataset 2, Datasets 3-5, and Dataset 6, respectively. It can be seen from the tables that FMA's performance is largely comparable to SWTPE performance (nearly the same $P_{dWROI}$ obtained via both algorithms), sometimes even better. For instance, FMA yields better $P_d$ in the case of Chemical_A, Chemical_B, and Chemical_E of Dataset 5 and the two files of Chemical_B-on-concrete in Dataset 6.

TABLE 2

Performance comparison of SWTPE and FMA on Dataset 2

| TMeS-on-Glass | | | TMeS-on-Gravel | | |
| --- | --- | --- | --- | --- | --- |
| Drop diameters (mm) | $P_{dWROI}$ (SWTPE) | $P_{dWROI}$ (FMA) | Drop diameters (mm) | $P_{dWROI}$ (SWTPE) | $P_{dWROI}$ (FMA) |
| 0.49 | 0 | 0.01 | 0.5 | 0.2 | 0.47 |
| 0.56 | 0.01 | 0 | 0.61 | 0.5 | 0.86 |
| 0.68 | 0.09 | 0.04 | 0.64 | 0.61 | 0.69 |
| 0.7 | 0.11 | 0.4 | 0.65 | 0.6 | 0.67 |
| 0.85 | 0.26 | 0.1 | 0.88 | 0.68 | 0.8 |
| 0.92 | 0.42 | 0.1 | 1.06 | 0.84 | 0.92 |
| 0.94 | 0.42 | 0.16 | 1.22 | 0.9 | 0.92 |
| 0.98 | 0.59 | 0.31 | 1.3 | 0.84 | 0.86 |
| 1.07 | 0.71 | 0.52 | 1.42 | 0.91 | 0.9 |
| 1.17 | 0.77 | 0.5 | 1.43 | 0.97 | 0.97 |
| 1.41 | 0.89 | 0.69 | 1.72 | 1 | 1 |
| 1.43 | 0.89 | 0.74 | 1.9 | 0.96 | 0.96 |
| 1.6 | 0.87 | 0.77 | 1.91 | 0.84 | 0.98 |
| 1.64 | 0.89 | 0.81 | 2.07 | 0.98 | 0.98 |
| 1.75 | 0.92 | 0.82 | 3.5 | 0.98 | 0.98 |
| 1.77 | 0.96 | 0.89 | | | |
| 1.99 | 0.95 | 0.88 | | | |
| 2.1 | 0.91 | 0.83 | | | |
| 2.25 | 0.92 | 0.86 | | | |
| 2.33 | 0.96 | 0.89 | | | |

TABLE 3

Performance comparison of SWTPE and FMA on Datasets 3-5.

| | Chemical | $P_{dWROI}$ (SWTPE) | $P_{dWROI}$ (FMA) |
| --- | --- | --- | --- |
| Dataset 3 | MES (0.5 µL) | 0.998 | 0.998 |
| | MES (1 µL) | 0.991 | 0.998 |
| | MES (5 µL) | 0.984 | 0.992 |
| | MES (10 µL) | 0.999 | 1.000 |
| | TEPO (0.5 µL) | 0.716 | 0.551 |
| | TEPO (1 µL) | 0.995 | 0.937 |
| | TEPO (5 µL) | 1.000 | 1.000 |
| | TEPO (10 µL) | 1.000 | 1.000 |
| Dataset 4 | Chemical_A | 0.597 | 0.728 |
| | Chemical_B | 0.949 | 1.000 |
| | Chemical_C | 0.804 | 0.720 |
| | Chemical_E | 1.000 | 1.000 |
| Dataset 5 | Chemical_A-on-concrete | 0.613 | 0.882 |
| | Chemical_B-on-concrete | 0.715 | 0.849 |
| | Chemical_C-on-concrete | 0.910 | 0.490 |
| | Chemical_E-on-concrete | 0.961 | 0.979 |

TABLE 4

Performance comparison of SWTPE and FMA on Dataset 6.

| Chemical | $P_{fa}$ | $P_{dWROI}$ (SWTPE) | $P_{dWROI}$ (FMA) |
| --- | --- | --- | --- |
| Chemical_B-on-concrete 1 | 0.2 | 0.82 | 0.98 |
| Chemical_B-on-concrete 2 | 0.2 | 0.82 | 0.99 |
| Chemical_B-on-asphalt 1 | 0.5 | 0.56 | 0.44 |
| Chemical_B-on-asphalt 2 | 0.5 | 0.55 | 0.44 |

FMA markedly reduces the processing time. As one example, table 5 shows that SWTPE takes 0.227 seconds of processing time to estimate the pedestal, whereas FMA takes only 0.032 seconds, nearly an order of magnitude faster.

These computation times were obtained by averaging the times taken to estimate the pedestal in 988 Chemical_B spectra of Dataset 4 on a Pentium M 1.5 GHz Windows based PC via a MATLAB program. Given the throughput operational requirements of LISA, assumed as 25 decisions per second, SWTPE was found to make about 4 decisions per second, whereas FMA was found to make about 25 decisions per second. On the other hand, if computation time is not a constraint, then FMA has the time to average 5 spectra to boost the SNR and obtain performance gain over SWTPE in the same time period.

TABLE 5

Processing time for each component of SWTPE and FMA

| Operation | SWTPE (seconds/spectrum) | FMA (seconds/spectrum) |
| --- | --- | --- |
| Filtering Normalization IRC correction | $8.51 \times 10^{-4}$ | $1.13 \times 10^{-3}$ |
| Pedestal removal | $2.27 \times 10^{-1}$ | $3.2 \times 10^{-2}$ |
| Interference truncation | $1.2 \times 10^{-2}$ | $1.13 \times 10^{-2}$ |
| FWR Correlation | $5.89 \times 10^{-4}$ | $5.78 \times 10^{-4}$ |
| WROI Correlation | $2.22 \times 10^{-4}$ | $3.14 \times 10^{-4}$ |
| Total Time | $2.4 \times 10^{-1}$ | $4 \times 10^{-2}$ |

Because SWTPE does not ignore chemical spectral features even when they have magnitudes comparable to noise features, SWTPE is robust to noise. It processes them without regard to what the features represent. In doing so, SWTPE recovers parts of the Raman signature yielding higher correlation coefficients than FMA. The disadvantage of processing the entire spectral region, however, is that it is computationally intensive in comparison with FMA.

Assuming that a high SNR spectrum is present, the advantages of FMA are that it correctly identifies the region where chemical features are present and processes only those regions. This eliminates processing redundancies as reflected in the processing times mentioned earlier. Further, working with features allows feature-oriented processing, which offers greater flexibility. For instance, if a given chemical library spectrum does not have any signature feature in a certain spectral band, then we can ignore features in the measured spectra occupying that spectral band and use only the feature boundary points already located. Ignoring spectral features in the measured spectra via SWTPE, on the other hand, warrants additional processing steps to avoid abrupt feature truncations.

The results above show that the feature metric algorithm (FMA) is a faster chemical signature detection algorithm that yields $P_d$ versus $\tau_{correlation}$ performance results comparable to SWTPE. FMA may be advantageously utilized when high SNR data is present, and/or when spectra averaging is beneficial. If the amount of time taken for SWTPE to process one high SNR spectrum satisfies the operational requirements, then FMA may be used instead with up to 5 spectra averaged in the same time, thereby exploiting the advantages of averaging. Nonetheless, if averaging is not beneficial, then SWTPE, which is more robust to noise, could be used instead of FMA at the cost of slower single spectrum processing.

Disclosed herein are three examples of detection algorithms to detect and identify chemical Raman signatures in Raman-shift data. The Raman-shift data suffer largely from three kinds of signal degradations: the pedestal resulting from fluorescence and instrument-effects, additive noise, and interference from non-target-chemicals. The pedestal, which is the most dominant source of signal degradation, was subtracted using its estimate. Three techniques of estimating the pedestal were developed for the three algorithms: linear interpolation pedestal estimation (LIPE), sliding-window technique for pedestal estimation (SWTPE), and feature-metric algorithm (FMA).

The additive noise effects were reduced by employing a lowpass (LP) filter. The LP filter was first designed with regards to the needs of the pedestal estimation technique when N>1 spectra were averaged. The interference from non-target sources was addressed by truncating certain interfering peaks. Since the algorithm has no advance knowledge of the interferrants, a set of most commonly occurring interfering peaks were identified and truncated in both measured and library spectra. Some interfering peaks, however, overlap with chemical signature features. Truncating such interfering peaks, therefore, also truncated valid chemical signatures. It was demonstrated to a certain extent that the detection performance did not deteriorate as long as truncation was performed in both the measured and library spectra; however, truncating too many interfering peaks compromises detection performance.

The LIPE involves pedestal estimation based on linear interpolation on the entire set of local minima in the data. It was shown that LIPE yields good detection results for higher concentrations (measured in terms of drop-diameter size) of the chemical (TMeS). The LIPE splits multiplets into individual peaks, however, due to linear interpolation on the entire set of local minima. Multiplets, although inconsequential from a detection perspective, provide important chemical characteristic information to spectroscopists. The SWTPE technique of pedestal estimation was designed to retain multiplets without compromising detection performance and, thereby, cater to the needs of spectroscopists. It was shown that SWTPE indeed performs well in retaining multiplets and performs comparably to LIPE in the case of TMeS drop data (Dataset 2).

Both LIPE and SWTPE exploit averaging as a means to improve the SNR of the input data and, therefore, need many input spectra before a decision is made. The operational requirements, however, encourage single spectrum decisions. Further, averaging does not always yield a higher SNR data. On the contrary, it averages-out chemical signatures if fewer chemical spectra are present among many background spectra in the set of input spectra. To adapt the SWTPE to single spectrum processing (SSP), an averaging filter equivalent was designed called the SSP-filter. The SSP-filter yields nearly the same smooth spectrum as does a combination of averaging and LP filtering. All datasets were subsequently processed via the SWTPE and the SSP-filter. The results obtained were acceptable in that the correlation coefficients obtained by correlating the measured and library spectra were sufficiently higher than the correlation between the library and background spectra.

Although the SSP-filter aided the SWTPE in yielding good detection performance, the SWTPE algorithm is computationally intensive. The FMA feature-oriented processing technique itself provides an alternative that is less computationally intense, processing only those spectral regions where chemical signature features are likely to be present. The FMA builds a feature-mask that supports a set of features that are most likely representative of a given chemical's Raman signature. This approach is sensitive to noise, however, because it searches for certain kinds of features in the data. If the chemical signature is buried in background and noise, then FMA is challenged to discriminate chemical signature features from noise features. For reasonably high SNR, however, the FMA yields comparable results to SWTPE, sometimes even better by almost an order of magnitude lesser time.

Finally, the good performance of both the algorithms, on a dataset containing Chemical_B-on-background spectra randomly inserted among many background spectra, proved their detection capabilities. The Chemical_B when on concrete is readily identified, but when on asphalt is not detected. This result was corroborated by ECBC: Chemical_B-on-asphalt files indeed do not have Chemical_B-on-asphalt spectra because a chemical reaction occurs between Chemical_B and asphalt that replaces Chemical_B with a new chemical product.

The LIPE's detection performance demonstrates the effectiveness of reducing, if not eliminating, the pedestal. It also demonstrates that: (a) as long as the measured and library spectra are processed in the same way, a correlation comparison is justified and (b) spectra averaging drastically improves detection performance and should be used where ever possible within the operational time constraints. The SWTPE, developed with the aim of retaining multiplets, yields reasonably high detection rates $\geq 0.8$ for a correlation threshold $\tau_{correlation}=0.7$ for six chemicals—TMeS, MES, TEPO, Chemical_B, Chemical_C, and Chemical_E. It yields relatively less detection rate ($\approx 0.7$) for the same correlation threshold in the case of Chemical_A. The SWTPE, however, demonstrates the usefulness of wavenumber region of interest (WROI) correlation and interfering-peak truncation. Carrying forward the idea that similar processing of the library and measured spectra admits a fair comparison, a set of interfering peaks were identified and truncated in all data irrespective of the chemicals and backgrounds. It was shown that the detection results did not change significantly and were favorably high ($P_{dWROI}>0.8$ at $\tau_{correlation}=0.7$) for Chemical_B, Chemical_C, and Chemical_E of Dataset 4. SWTPE is, however, computationally intensive. The FMA, developed to reduce this computational load, performs nearly an order of magnitude faster than SWTPE and yields detection rates close to those of SWTPE. SWTPE has the advantage of being more robust to noise and can process 4 spectra per second, whereas FMA can process 25 spectra per second. These processing rates were computed based on processing on a Pentium M 1.5 GHz Windows PC via a MATLAB program and are not limitations on the algorithms themselves. If averaging is beneficial, then FMA may be used with up to 5 spectra averaged to yield a decision in the same time as SWTPE takes to yield a decision on a single spectrum.

To minimize the dependence of the SWTPE and FMA algorithms on the data, exhaustive tests may be performed to see if one set of parameters suits all. If not, then chemicals may be grouped into classes with each class requiring a certain set of parameter values.

The SWTPE may be optimized to make it more computationally efficient by way of mapping the window domains in each run and stopping a run if the current window domain is identical to a domain of a previous run. The basis for this optimization approach is that when a window domain is identical to a domain from a previous run, the subsequent domains will be the same and, therefore, the pedestal estimates will be the same from that domain onwards.

It is seen that several small magnitude peaks, a consequence of additive noise, are either falsely detected as spectral peaks or appear to reduce the range of a broader chemical signature feature. These small-magnitude peaks may be ignored by either thresholding their magnitudes or identifying local extrema differently, i.e., via ±threshold-crossing/touching rather than zero-crossing/touching. The smaller-magnitude peaks will have smaller derivatives and, therefore, their derivatives can be expected not to exceed a certain threshold on either side of zero. By setting two thresholds, of the same magnitude but opposite signs, we can identify only those local extrema that are a result of a high-magnitude peak's derivative.

The chemical signature strength greatly affects the detection performance; therefore, knowing the SINR in advance would be beneficial. The signal strength may be estimated using knowledge of the distance of the target from the laser and the laser power. Using this measurement information, the algorithm's parameters may be chosen more intelligently.

The current measure of closeness, the correlation threshold, has proved to be counter intuitive sometimes. For instance, certain spectral features that have large magnitudes boost the correlation coefficient even when the Raman signature in the rest of the spectral range does not match the library spectrum. This could increase the probability of mismatch (i.e., the probability of choosing chemical X when the chemical is actually Y). In FMA, alternatively, each feature may be correlated with the spectral data in the corresponding spectral range and then all correlation coefficients combined in a manner reflective of the overall closeness.

The FMA combines the feature magnitudes and feature widths in computing the feature metric. Although such a combination relies on the usefulness of both feature properties, it also is sensitive to their shortcomings. For instance, the feature width may be reduced significantly by additive noise. The use of the modified local extrema identification discussed above may eliminate the problem; however, it will be useful to consider a weighted combination of three correlation coefficients as the closeness measure, each obtained by feature-width-oriented, feature-magnitude-oriented, and feature-location-oriented processing of the spectrum, respectively. Thus each of the feature's attributes would be considered and, therefore, the resulting algorithm will be more accurate in describing the closeness of the two spectra. However, this will increase the computational load.

Another approach to the detection problem is to process the chemicals based on the library spectra (i.e., develop processing techniques that use only certain spectral ranges identified based on the chemical signature in the library spectrum, seeking certain chemical signatures in certain locations, etc). In other words, the given measured data may be processed as many times as there are chemical spectra in the library set. This will drastically improve detection results because each time the data is processed, it is assumed that a certain chemical is present until a closeness measure disproves it. This approach, however, is highly computation intensive. Some steps for reducing the computational load may be performed, for example, by grouping similar chemical signatures and choosing one particular processing technique for a given group.

Finally, the SWTPE and the FMA algorithms may be implemented on a DSP board. Use of dedicated digital signal processing circuitry drastically reduces the computation times allowing more involved processing techniques: for instance, the chemical library oriented processing described above. Further, the two algorithms may be implemented in a parallel architecture and the corresponding results may be combined to make a better decision. This parallel processing is motivated by the fact that the two algorithms detect certain chemicals better than the other.

In accord with the above described aspects of the present concepts, there is therefore provided a signal processing system comprising a processor, at least one I/O device operatively associated with the processor, and a memory device bearing instructions configured for execution by the processor, the instructions being configured, upon execution by the processor, to cause the processor to acts consistent with the present disclosure. In one example, the instructions, may cause the processor to obtain a representation of signal data over a data domain, position a sliding-window over a portion of the signal data, the portion of the data domain within the sliding-window corresponding to a sliding-window domain, and analyze the signal data within the sliding-window domain to detect the presence of a signature multiplet. The instructions in this example further cause the processor to, based on this analysis of the data, estimate the pedestal of the signal data within the sliding-window domain, iteratively shift the sliding-window over at least a portion of the data domain to correspondingly shift the sliding-window domain, estimate the pedestal of the signal data within each sliding-window domain to determine an estimated pedestal over the at least a portion of the data domain, subtract the estimated pedestal from the signal data to yield a pedestal-free representation of the signal data for the at least a portion of the data domain, and output the pedestal-free representation of the signal data for the at least a portion of the data domain to at least one of a communication device, a display, a printing device, or a data storage device.

The aforementioned processor may comprise a part of a computer system upon which one embodiment of the invention may be implemented. A typical computer system would comprise one or more such processors and a bus or other communication mechanism for communicating information. Such computer system would also typically comprise a main memory, such as a random access memory (RAM) or other dynamic storage device, coupled to the bus for storing information and instructions to be executed by the processor(s). The main memory also may be used for storing temporary variables or other intermediate information during execution of instructions to be executed by the processor(s). The computer system further includes a read only memory (ROM) or other static storage device coupled to the bus for storing static information and instructions for the processor(s). A storage device, such as a magnetic disk, optical disk, or solid state storage device, may also be provided and coupled to bus to permit storing of and retrieval of information and instructions.

Computer system may be coupled via bus to a display, such as a flat screen display or touch screen display, for displaying information to a computer user. One or more input device, including alphanumeric and other keys, cursor controller (e.g., a mouse, a trackball, cursor direction keys, etc.) are also coupled to bus for communicating information and command selections to the processor(s) for communicating direction information and command selections to the processor(s) and for controlling cursor movement on display.

As noted above, according to one aspects of the invention, the aforementioned signal processing techniques are provided by a computer system in response to processor(s) executing one or more sequences of one or more instructions contained in main memory. Such instructions may be read into the main memory from another computer-readable medium, such as a storage device (e.g., hard disk, solid state media, etc.). Execution of the sequences of instructions contained in main memory causes the processor(s) to perform the process steps described herein. One or more processors in a multi-processing arrangement may also be employed to execute the sequences of instructions contained in main memory. In alternative embodiments, hard-wired circuitry may be used in place of or in combination with software instructions (e.g., firmware) to implement the invention. Thus, embodiments of the invention are not limited to any specific combination of hardware circuitry and software.

The term "computer-readable medium" as used herein refers to any medium that participates in providing instructions to a processor for execution. Such a medium may take many forms, including but not limited to, non-volatile media, volatile media, and transmission media. Non-volatile media include, for example, optical or magnetic disks, such as storage device. Volatile media include dynamic memory, such as main memory. Transmission media include coaxial cables, copper wire and fiber optics, including the wires that comprise bus. Transmission media can also take the form of acoustic or light waves, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, and EPROM, a FLASH-EPROM, any other memory chip or cartridge, a carrier wave, or any other medium from which a computer can read.

Various forms of computer readable media may be involved in carrying one or more sequences of one or more instructions to the processor(s) for execution. For example, the instructions may initially be borne on a magnetic disk of a remote computer. The remote computer can load the instructions into its dynamic memory and send the instructions over a telephone line using a modem. A modem local to computer system can receive the data on the telephone line and use an infrared transmitter to convert the data to an infrared signal. An infrared detector coupled to bus can receive the data carried in the infrared signal and place the data on bus. Bus carries the data to main memory, from which processor(s) retrieve(s) and execute(s) the instructions. The instructions received by main memory may optionally be stored on storage device either before or after execution by processor. Such a computer system may also include a communication interface coupled to the bus. A communication interface provides a two-way data communication coupling (or possibly a one-way communication coupling) to a network link that is connected to a local network. For example, the communication interface may be an integrated services digital network (ISDN) card or a modem to provide a data communication connection to a corresponding type of telephone line. As another example, the communication interface may be a local area network (LAN) card to provide a data communication connection to a compatible LAN. Wireless links utilizing wireless communication interfaces may also be implemented. In any such implementation, the communication interface sends and receives electrical, electromagnetic or optical signals that carry digital data streams representing various types of information (carrier waves).

A network link typically provides data communication through one or more networks to other data devices. For example, a network link may provide a connection through a local network to a host computer or to data equipment operated by an Internet Service Provider (ISP). The computer system can send and receive data (e.g., spectral data, libraries, etc.) and/or program code, through the network(s), network link, and communication interface. In the Internet example, a server might transmit a requested code for an application program through the Internet, ISP, local network and communication interface. In accord with the invention, one such downloaded application provides for practicing the signal processing concepts described herein. The received code may be executed by processor as it is received, and/or stored in storage device, or other non-volatile storage for later execution. In this manner, the computer system may obtain application code in the form of a carrier wave.

In at least some aspects of the present concepts, the computer system is configured to receive data obtained from an instrument, such as a Raman spectroscopy instrument optical array detector, through intermediary devices. For example, an instrument (e.g., any variety of Raman spectroscopy instrument) may communicate wirelessly with a local or remote computer, such as through a wireless local area network (WLAN), wireless personal area network (WPAN), wireless metropolitan area network (WMAN), wireless wide area network (WWAN), or other wireless network implemented in accord with related standards or protocols (e.g., the Institute of Electrical and Electronics Engineers (IEEE) 802.11 family of WLAN standards, IEEE 802.15.1 (Bluetooth), IEEE 802.12.3, etc.). Such instrument may also communicate with a local computer via a hard-wired connector connecting the instrument to the computer. Alternatively, the computer system may itself be integrated into a portable or field instrument such that the processing functions are performed "on board" the instrument. Although one exemplary type of instrument (e.g., a Raman spectroscopy instrument) has been described herein, the techniques disclosed herein are not necessarily limited thereto. As noted above, the signal processing techniques disclosed herein may be advantageously used to isolate and enhance signals within data, such as data having an arbitrarily-varying noisy background that is characterized by an unknown slow-varying mean and variance. Signals with spectral density signatures obtained from a Raman scattering process are an example of a class of signals to which the present concepts may be advantageously applied, but are not limiting on the techniques disclosed herein. For example, the techniques disclosed herein may apply to any signals subject to arbitrary additive noisy backgrounds, where there is limited knowledge about background statistics.

While the present invention has been described with reference to one or more particular implementations, those skilled in the art will recognize that many changes may be made thereto without departing from the spirit and scope of the present invention. Each of these implementations and obvious variations thereof is contemplated as falling within the spirit and scope of the invention, which is set forth in the following alternative implementations.

What is claimed:
1. A signal processing system comprising:
a processor;
at least one I/O device operatively associated with the processor; and
a non-transitory memory device, the non-transitory memory device bearing instructions configured for execution by a processor, the instructions being config- ured, upon execution by said processor, to cause the processor to perform the acts of:

obtaining a representation of signal data over a data domain;

positioning a sliding-window over a portion of the signal data, the portion of the data domain within the sliding-window corresponding to a sliding-window domain;

analyzing the signal data within the sliding-window domain to detect the presence of a signature multiplet;

estimating a pedestal of the signal data within the sliding-window domain for any detected signature multiplet;

shifting the sliding-window to encompass another portion of the data domain to correspondingly shift the sliding-window domain;

repeating the steps of analyzing the signal data, estimating the pedestal of the signal data, and shifting the sliding-window;

subtracting any estimated pedestal or pedestals from the signal data to yield a pedestal-free representation of the signal data for at least a portion of the data domain; and outputting the pedestal-free representation of the signal data for the at least a portion of the data domain to at least one of a communication device, a display, a printing device, or a physical data storage device.

2. The signal processing system of claim 1, wherein the instructions are further configured, upon execution by said processor, to cause the processor to perform the act identifying a plurality of local minima of the signal data.

3. The signal processing system of claim 2, wherein the instructions are further configured, upon execution by said processor, to cause the processor to perform, for the act of identifying a plurality of local minima of the data, the acts of:

computing the difference of the signal data; and identifying the local minima by identifying the data domain values at which the difference of the signal data changes sign from negative to non-negative.

4. The signal processing system of claim 3, wherein the instructions are further configured, upon execution by said processor, to cause the processor to perform, for the act of computing of the difference of the signal data, the act of representing d(n) by the expression datafunction(n+1)-datafunction(n), for 1<n<N, where N is an integer, and where datafunction is an N-point representation of the signal data over the data domain, d is an N-point difference of the signal data, and n is the sample number.

5. The signal processing system of claim 2, wherein the instructions are further configured, upon execution by said processor, to cause the processor to perform, for the analyzing of the signal data within the sliding-window domain to detect the presence of a signature multiplet, the acts of:

identifying the local minima having the smallest domain value within the sliding-window domain as a first boundary point and the local minima within the sliding-window domain having the greatest domain value as a second boundary point;

computing a boundary value as the difference between the first boundary point and the second boundary point; and comparing the boundary value with a threshold value to detect the presence of a signature multiplet.

6. The signal processing system of claim 5, wherein the instructions are further configured, upon execution by said processor, to cause the processor to perform, for the act of estimating the pedestal of the signal data within the sliding-window domain, the acts of:

estimating the pedestal of the signal data within the sliding-window domain by linear interpolation between the first boundary point and the second boundary point if a multiplet is detected; and estimating the pedestal of the signal data within the sliding-window domain by linear interpolation between all local minima within the sliding-window domain if a multiplet is not detected.

7. The signal processing system of claim 2, wherein the instructions are further configured, upon execution by said processor, to cause the processor to perform, for the act of shifting the sliding-window, the acts of:

shifting the sliding-window along the data domain such that the second boundary point becomes the first boundary point if a multiplet is detected within the sliding-window; and shifting the sliding-window along the data domain such that the first boundary point becomes the adjacent local minimum of a greater data domain value if a multiplet is not detected within the sliding-window.

8. The signal processing system of claim 1, wherein the instructions are further configured, upon execution by said processor, to cause the processor to perform the act of selecting a sliding-window length corresponding to the span of the sliding-window domain, said act of selecting a sliding-window length further comprising the acts of:

normalizing the signal data with respect to magnitude;

sampling the signal data to obtain data sample points;

computing the difference of the signal data over at least a portion of the data domain;

identifying local minima points across the at least a portion of the data domain via identification of data domain values at which the difference of the signal data changes sign from negative to non-negative;

identifying all data domain values at which the magnitude of the difference is greater than a difference threshold as center points;

identifying the two local minima adjacent every center point, the span between every pair of local minima being the span of a respective signature peak;

grouping all adjacent signature peaks to obtain a peak-set, the span of each peak-set being the difference between an end point and a start point of the peak-set; and selecting the widest peak-set span as the sliding-window length.

9. The signal processing system of claim 8, wherein the difference threshold is one-third.

10. The signal processing system of claim 1, wherein the instructions are further configured, upon execution by said processor, to cause the processor to perform the acts of:

iteratively shifting the sliding-window over the entire data domain at least two times;

for each iteration over the entire data domain, initially positioning the sliding-window over a different portion of the data domain;

for each iteration over the entire data domain, determining a pedestal estimate value for each domain value; and selecting the best pedestal estimate value for each domain value from all the pedestal values determined over all the iterations over the entire data domain.

11. The signal processing system of claim 1, wherein the signal data is characterized by signature peaks within the signal data having an arbitrarily-varying noisy background characterized by an unknown slow-varying mean and variance.

12. A computer readable non-transitory memory bearing instructions configured for execution by a processor, the instructions being configured, upon execution by a processor, to cause the performance of the following acts:

obtaining a representation of signal data over a data domain;

positioning a sliding-window over a portion of the signal data, the portion of the data domain within the sliding-window corresponding to a sliding-window domain;

analyzing the signal data within the sliding-window domain to detect the presence of a signature multiplet;

estimating a pedestal of the signal data within the sliding-window domain for any detected signature multiplet;

shifting the sliding-window to encompass another portion of the data domain to correspondingly shift the sliding-window domain;

repeating the steps of analyzing the signal data, estimating the pedestal of the signal data, and shifting the sliding-window;

subtracting any estimated pedestal or pedestals from the signal data to yield a pedestal-free representation of the signal data for at least a portion of the data domain; and outputting the pedestal-free representation of the signal data for the at least a portion of the data domain to at least one of a communication device, a display, a printing device, or a data storage device.

13. A signal processing system comprising:

a processor;

at least one I/O device operatively associated with the processor; and a non-transitory memory device, the non-transitory memory device bearing instructions configured for execution by a processor, the instructions being configured, upon execution by said processor, to cause the processor to perform the acts of:

identifying a plurality of features from signal data by identifying a plurality of local maxima and local minima of the signal data and defining each feature by a local maximum bounded between two local minima, the two local minima being a left-hand local minimum and a right-hand local minimum;

computing a metric for each of the plurality of features;

comparing each metric with a metric threshold to determine whether a corresponding feature is a signature feature;

identifying one or more feature-sets by grouping adjacent signature features;

estimating the pedestal for each feature-set;

subtracting the pedestal for each feature-set from the signal data to yield a pedestal-free representation of the signal data; and outputting the pedestal-free representation of the signal data for the at least a portion of the data domain to at least one of a communication device, a display, a printing device, or a data storage device.

14. The signal processing system of claim 13, wherein each feature includes a left-hand feature and a right-hand feature, each metric includes a left-half feature metric and a right-half feature metric, and wherein the instructions are further configured, upon execution by said processor, to cause the processor to perform, for the computing of the metric for each of the plurality of features, the acts of:

computing the left-hand feature metric according to a function related to at least a portion of the area enclosed within the left-hand feature;

computing the right-hand feature metric according to a function related to at least a portion of the area enclosed within the right-hand feature; and synthesizing the metric as a function that includes the left-hand feature metric and the right-hand feature metric.

15. The signal processing system of claim 14, wherein the left-hand feature metric is the product of a left-half-height and the width of the left-hand feature, the left-half-height being the magnitude between the local maximum and a left-half midpoint, the left-half midpoint being the average of the magnitude of the local maximum and the left-hand local minimum, and the right-hand feature metric is the product of a right-half-height and a width of the right-hand feature metric, the right-half-height being the magnitude difference between the local maxima and a right-half midpoint, the right-half midpoint being the average of the local maximum and the right-hand local minimum.

16. The signal processing system of claim 14, wherein the metric threshold is independent of the signal data.

17. The signal processing system of claim 14, further comprising selecting the metric threshold such that a predefined number of feature-sets are identified.

18. The signal processing system of claim 17, wherein the instructions are further configured, upon execution by said processor, to cause the processor to perform, for the act selecting the metric threshold, the acts of:

selecting an initial value as the metric threshold;

comparing each metric with the metric threshold to determine whether the predetermined number of feature-sets are identified;

increasing the feature metric by an increment amount until the predetermined number of feature-sets are identified if the predetermined number of feature-sets are not identified; and selecting the metric threshold that identified the maximum number of feature-sets if the predefined number of feature-sets cannot be defined.

19. The signal processing system of claim 18, wherein a first metric threshold is incremented by the increment amount to yield a second metric threshold, and the first metric threshold identifies the maximum number of feature-sets when the second metric threshold identifies fewer feature-sets than the first metric threshold.

20. The signal processing system of claim 13, wherein the instructions are further configured, upon execution by said processor, to cause the processor to perform, for the act of estimating the pedestal of a particular feature-set, the acts of:

obtaining a first pedestal estimate by linearly connecting all the local minima in the feature-set;

obtaining a second pedestal estimate by linearly connecting the first and last sample points in the feature-set;

comparing the first pedestal estimate with the second pedestal estimate; and selecting the lesser of the first pedestal estimate and the second pedestal estimate as the pedestal estimate for the particular feature-set.

* * * * *